US010995341B2

(12) United States Patent
Ronen et al.

(10) Patent No.: US 10,995,341 B2
(45) Date of Patent: *May 4, 2021

(54) POLYNUCLEOTIDES, POLYPEPTIDES ENCODED THEREBY, AND METHODS OF USING SAME FOR INCREASING ABIOTIC STRESS TOLERANCE AND/OR BIOMASS AND/OR YIELD IN PLANTS EXPRESSING SAME

(71) Applicant: Evogene Ltd., Rehovot (IL)

(72) Inventors: Gil Ronen, Emek Hefer (IL); Hagai Karchi, Moshav Sitriya (IL); Alex Diber, Rishon-LeZion (IL); Basia Judith Vinocur, Rechovot (IL); Sharon Ayal, Kibbutz Bet Nir (IL); Eyal Emmanuel, Rehovot (IL); Michael Gang, Jerusalem (IL); Dotan Dimet, Kibbutz Beir Nir (IL)

(73) Assignee: Evogene Ltd., Rehovot (IL)

(*) Notice: Subject to any disclaimer, the term of this patent is extended or adjusted under 35 U.S.C. 154(b) by 0 days.

This patent is subject to a terminal disclaimer.

(21) Appl. No.: 16/218,559

(22) Filed: Dec. 13, 2018

(65) Prior Publication Data

US 2019/0100767 A1 Apr. 4, 2019

Related U.S. Application Data

(60) Continuation of application No. 15/278,086, filed on Sep. 28, 2016, now Pat. No. 10,155,957, which is a division of application No. 14/071,715, filed on Nov. 5, 2013, now Pat. No. 9,518,267, which is a continuation of application No. 12/669,975, filed as application No. PCT/IL2008/001024 on Jul. 24, 2008, now Pat. No. 8,686,227.

(60) Provisional application No. 60/935,046, filed on Jul. 24, 2007.

(51) Int. Cl.
*C12N 15/82* (2006.01)
*C07K 14/415* (2006.01)
*A01H 1/00* (2006.01)
*A01H 5/00* (2018.01)
*C12N 15/00* (2006.01)

(52) U.S. Cl.
CPC .......... *C12N 15/8273* (2013.01); *A01H 1/00* (2013.01); *A01H 5/00* (2013.01); *C07K 14/415* (2013.01); *C12N 15/00* (2013.01); *C12N 15/8247* (2013.01); *C12N 15/8261* (2013.01); *C12N 15/8271* (2013.01); *Y02A 40/146* (2018.01)

(58) Field of Classification Search
CPC .......... C12N 15/8271; C12N 15/8261; C12N 15/8273; C07K 14/415
See application file for complete search history.

(56) References Cited

U.S. PATENT DOCUMENTS

| | | | |
|---|---|---|---|
| 6,084,153 A | 7/2000 | Good et al. | |
| 7,847,156 B2 * | 12/2010 | Inze | C07K 14/415 800/290 |
| 8,686,227 B2 | 4/2014 | Ronen et al. | |
| 10,155,957 B2 * | 12/2018 | Ronen | C12N 15/8273 |
| 2002/0046419 A1 | 4/2002 | Choo et al. | |
| 2004/0031072 A1 | 2/2004 | La Rosa et al. | |
| 2004/0123343 A1 | 6/2004 | La Rosa et al. | |
| 2005/0054831 A1 | 3/2005 | Hwang et al. | |
| 2005/0054931 A1 | 3/2005 | Clark | |
| 2005/0108791 A1 | 5/2005 | Edgerton | |
| 2006/0021088 A1 | 1/2006 | Inze et al. | |
| 2006/0123505 A1 | 6/2006 | Kikuchi et al. | |
| 2006/0179511 A1 | 8/2006 | Chomet et al. | |
| 2007/0039067 A1 | 2/2007 | Feldmann et al. | |
| 2008/0301839 A1 | 12/2008 | Ravanello | |
| 2010/0319088 A1 | 12/2010 | Ronen et al. | |
| 2014/0068819 A1 | 3/2014 | Ronen et al. | |
| 2017/0009251 A1 | 1/2017 | Ronen et al. | |
| 2019/0032075 A1 | 1/2019 | Ronen et al. | |

FOREIGN PATENT DOCUMENTS

| | | |
|---|---|---|
| CA | 2420555 | 2/2002 |
| EP | 1551983 | 7/2005 |
| EP | 1601758 | 12/2005 |
| WO | WO 2004/081173 | 9/2004 |
| WO | WO 2004/104162 | 12/2004 |

(Continued)

OTHER PUBLICATIONS

Report Prior to Final Decision dated Nov. 19, 2019 From the Instituto Nacional de la Propiedad Industrial, Administracion Nacional de Patentes, INPI Argentina Re. Application No. P080105264 and Its English Summary. (6 Pages).
Restriction Official Action dated Jan. 30, 2020 From the US Patent and Trademark Office Re. U.S. Appl. No. 16/154,833. (6 pages).
Requisition by the Examiner dated Aug. 27, 2019 From the Canadian Intellectual Property Office Re. Application No. 3,019,282. (3 pages).
Applicant-Initiated Interview Summary dated Aug. 6, 2012 From the US Patent and Trademark Office Re. U.S. Appl. No. 12/669,975.
Communication Pursuant to Article 94(3) EPC dated May 8, 2013 From the European Patent Office Re. Application No. 08776651.5.

(Continued)

*Primary Examiner* — Lee A Visone

(57) ABSTRACT

Provided are methods of increasing tolerance of a plant to abiotic stress, and/or increasing biomass, growth rate, vigor and/or yield of a plant. The methods are effected by expressing within the plant an exogenous polynucleotide encoding a polypeptide comprising an amino acid sequence at least 90% homologous to the amino acid sequence selected from the group consisting of SEQ ID NOs:201, 207, 212, 202-206, 208-211, 213-391, 1655, 961-1529, and 1660-1663. Also provided are polynucleotides, nucleic acid constructs, polypeptides and transgenic plants expressing same which can be used to increase tolerance of a plant to abiotic stress, and/or increase biomass, growth rate, vigor and/or yield of a plant.

7 Claims, 2 Drawing Sheets
Specification includes a Sequence Listing.

(56) References Cited

FOREIGN PATENT DOCUMENTS

| WO | WO 2004/111183 | 12/2004 |
|---|---|---|
| WO | WO 2005/060664 | 7/2005 |
| WO | WO 2005/121364 | 12/2005 |
| WO | WO 2007/020638 | 2/2007 |
| WO | WO 2007/049275 | 5/2007 |
| WO | WO 2008/075364 | 6/2008 |
| WO | WO 2008/122980 | 10/2008 |
| WO | WO 2009/013750 | 1/2009 |
| WO | WO 2009/083958 | 7/2009 |
| WO | WO 2009/141824 | 11/2009 |
| WO | WO 2010/020941 | 2/2010 |
| WO | WO 2010/049897 | 5/2010 |
| WO | WO 2010/076756 | 7/2010 |
| WO | WO 2010/100595 | 9/2010 |
| WO | WO 2010/143138 | 12/2010 |
| WO | WO 2011/015985 | 2/2011 |
| WO | WO 2011/080674 | 7/2011 |
| WO | WO 2011/135527 | 11/2011 |
| WO | WO 2012/028993 | 3/2012 |
| WO | WO 2012/085862 | 6/2012 |
| WO | WO 2012/150598 | 11/2012 |
| WO | WO 2013/027223 | 2/2013 |
| WO | WO 2013/078153 | 5/2013 |
| WO | WO 2013/080203 | 6/2013 |
| WO | WO 2013/098819 | 7/2013 |
| WO | WO 2013/128448 | 9/2013 |
| WO | WO 2013/179211 | 12/2013 |
| WO | WO 2014/033714 | 3/2014 |
| WO | WO 2014/102773 | 7/2014 |
| WO | WO 2014/102774 | 7/2014 |
| WO | WO 2014/188428 | 11/2014 |
| WO | WO 2015/029031 | 3/2015 |
| WO | WO 2015/181823 | 12/2015 |
| WO | WO 2016/030885 | 3/2016 |
| WO | WO 2017/115353 | 7/2017 |

OTHER PUBLICATIONS

Communication Pursuant to Article 94(3) EPC dated May 8, 2017 From the European Patent Office Re. Application No. 15151271.2. (6 Pages).
Communication Pursuant to Article 94(3) EPC dated Aug. 24, 2017 From the European Patent Office Re. Application No. 15151271.2. (4 Pages).
Decision on Rejection dated May 12, 2014 From the State intellectual Property Office of the People's Republic of China Re. Application No. 200880109464.9 and Its Translation Into English.
European Search Report and the European Search Opinion dated Sep. 16, 2015 From the European Patent Office Re. Application No. 15151271.2.
Examination Report dated Oct. 1, 2013 From the Instituto Mexican de la Propiedad Industrial Re. Application No. Mx/a/2010/000975 and Its Translation Into English.
Examination Report dated Nov. 6, 2018 From the Australian Government, IP Australia Re. Application No. 2017228711. (3 Pages).
Examination Report dated Jun. 12, 2015 From the Government of India, Patent Office, Intellectual Property Building Re. Application No. 1301/DELNP/2010.
Examination Report dated May 18, 2018 From the Australian Government, IP Australia Re. Application No. 2017228711. (6 Pages).
Examination Report dated May 25, 2015 From the Instituto Mexicano de la Propiedad Industrial, IMPI Re. Application No. MX/a/2013/010577 and Its Translatioin Into English.
Examination Report dated Jun. 26, 2013 From the Instituto Mexicano de la Propiedad Industrial Re. Application No. MX/a/2010/000975 and Its Translation Into English.
Examination Report dated Sep. 27, 2017 From the Instituto Nacional de la Propiedad Industrial, Administracion Nacional de Patentes, INPI Argentina Re. Application No. P080105264 and Its Translation Into English. (8 Pages).
Examination Report dated Sep. 27, 2018 From the Instituto Nacional de la Propiedad Industrial, Administracion Nacional de Patentes, INPI Argentina Re. Application No. P080105264 and Its Translation Into English. (7 Pages).
Examination Report dated Mar. 31, 2017 From the Australian Government, IP Australia Re. Application No. 2015230753. (10 Pages).
Hearing Notice dated Jan. 10, 2017 From the Government of India, Patent Office, Intellectual Property Building Re. Application No. 1301/DELNP/2010. (2 Pages).
International Preliminary Report on Patentability dated Feb. 4, 2010 From the International Bureau of WIPO Re. Application No. PCT/IL2008/001024.
International Search Report dated Mar. 4, 2009 From the International Searching Authority Re.: Application No. PCT/IL08/01024.
Invitation to Pay Additional Fees dated Dec. 18, 2008 From the International Searching Authority Re. Application No. PCT/IL08/01024.
Notice of Allowance dated Aug. 10, 2018 From the US Patent and Trademark Office Re. U.S. Appl. No. 15/278,086. (11 pages).
Office Action dated Jun. 25, 2012 From the State Intellectual Property Office of the People's Republic of China Re. Application No. 200880109464.9 and Its Translation Into English.
Official Action dated Apr. 10, 2012 From the US Patent and Trademark Office Re. U.S. Appl. No. 12/669,975.
Official Action dated Mar. 14, 2016 From the US Patent and Trademark Office Re. U.S. Appl. No. 14/071,715.
Official Action dated Apr. 16, 2018 From the US Patent and Trademark Office Re. U.S. Appl. No. 15/278,086. (29 pages).
Official Action dated Jan. 18, 2013 From the US Patent and Trademark Office Re. U.S. Appl. No. 12/669,975.
Official Action dated Sep. 20, 2013 From the US Patent and Trademark Office Re. U.S. Appl. No. 12/669,975.
Partial European Search Report (Rule 64(1) EPC) dated Jun. 1, 2015 From the European Patent Office Re. Application No. 15151271.2.
Patent Examination Report dated Jan. 3, 2014 From the Australian Government, IP Australia Re. Application No. 2008278654.
Patent Examination Report dated Feb. 1, 2018 From the Australian Government, IP Australia Re. Application No. 2017228711. (3 Pages).
Patent Examination Report dated Nov. 11, 2016 From the Australian Government, IP Australia Re. Application No. 2015230753.
Patent Examination Report dated May 31, 2013 From the Australian Government, IP Australia Re. Application No. 2008278654.
Requisition by the Examiner dated Jun. 3, 2015 From the Canadian Intellectual Property Office Re. Application No. 2,694,481.
Requisition by the Examiner dated Sep. 11, 2014 From the Canadian Intellectual Property Office Re. Application No. 2,694,481.
Requisition by the Examiner dated Mar. 31, 2016 From the Canadian Intellectual Property Office Re. Application No. 2,694,481.
Response dated Feb. 14, 2011 to Supplementary European Search Report and the European Search Opinion dated Jul. 29, 2010 From the European Patent Office Re. Application No. 08776651.5.
Restriction Official Action dated Feb. 1, 2012 From the US Patent and Trademark Office Re. U.S. Appl. No. 12/669,975.
Restriction Official Action dated Jan. 19, 2018 From the US Patent and Trademark Office Re. U.S. Appl. No. 15/278,086. (8 pages).
Restriction Official Action dated Oct. 28, 2015 From the US Patent and Trademark Office Re. U.S. Appl. No. 14/071,715.
Substantive Examination Report dated May 20, 2014 From the Intellectual Property Office of the Philippines, Bureau of Patents Re. Application No. 1/2010/500186.
Summons to Attend Oral Proceedings Pursuant to Rule 115(1) EPC dated Sep. 1, 2014 From the European Patent Office Re. Application No. 08776651.5.
Supplementary European Search Report and the European Search Opinion dated Jul. 29, 2010 From the European Patent Office Re. Application No. 08776651.5.
Translation of Examination Report dated Mar. 17, 2014 From the Ministry of Science and Technology, National Office of Intellectual Property (NOIP) of the Socialist Republic of Vietnam Re. Application No. 1-2010-00425.

(56) References Cited

OTHER PUBLICATIONS

Translation of Notice to Amendment dated Aug. 31, 2012 From the Thai Patent Office, Department of Intellectual Property Office Re. Application No. 0901000235.
Translation of Office Action dated Jan. 4, 2012 From the State Intellectual Property Office of the People's Republic of China Re. Application No. 200880109464.9.
Translation of Office Action dated Mar. 22, 2013 From the State Intellectual Property Office of the People's Republic of China Re. Application No. 200880109464.9.
Translation of Office Action dated Aug. 28, 2013 From the State Intellectual Property Office of the People's Republic of China Re. Application No. 200880109464.9.
Written Opinion dated Mar. 4, 2009 From the International Searching Authority Re.: Application No. PCT/IL08/01024.
Bhatnagar-Mathur et al. "Transgenic Approaches for Abiotic Stress Tolerance in Plants: Retrospect and Prospects", Plant Cell Reports, 27(3): 411-424, Mar. 2008.
Karaba et al. "Improvement of Water Use Efficiency in Rice by Expression of Hardy, An *Arabidopsis* drought and Salt Tolerance Gene", Proc. Natl. Acad. Sci. USA, PNAS, 104(39): 15270-15275, Sep. 25, 2007.
Kikuchi et al. "Rice cDNA Clone SEQ ID No. 16237", Database Geneseq [Online], Retrieved From EBI Accession No. GSN:AQD22378, Database Accession No. AQD22378, Jun. 12, 2008. Sequence.
Kikuchi et al. "Rice cDNA-Encoded Protein SEQ ID No. 29596", Database Geneseq [Online], Retrieved From EBI Accession No. GSP:AQD35737, Database Accession No. AQD35737, Jun. 12, 2008. Sequence.
Koonin et al. "Evolutionary Concept in Genetics and Genomics. 2.1 Similarity, Homology, Divergence and Convergence", Sequence-Evolution-Function, Chap.2: 25-49, 2003.
La Rosa et al. "Oryza Sativa Amino Acid Sequence SEQ ID No. 204749", Database Geneseq [Online], Retrieved From EBI Accession No. GSP:ANM90748, Database Accession No. ANM90748, Dec. 28, 2007. Sequence.
La Rosa et al. "Oryza Sativa Nucleotide Sequence SEQ ID No. 102266", Database Geneseq [Online], Retrieved From EBI Accession No. GSN:ANL88264, Database Accession No. ANL88264, Dec. 28, 2007. Sequence.
Li et al. "Glycine Max Cold-Regulated Protein (Cor1) mRNA, Complete Cds", NCBI Database [Online], GenBank Accession No. FJ393230.1, Database Accession No. FJ393230, Nov. 22, 2008.
Ma et al. "KGBassembler: A Karyotype-Based Genome Assembler for *Brassicaceae* Species", Bioinformatics, 28(23): 3141-3143, Dec. 1, 2012. Abstract.
Oxford Dictionay "Orotidine-5'-Phosphate Pyrophosphorylase", Oxford Dictionary of Biochemistry and Molecular Biology, Revised Edition, p. 473, 1997.
Papdi et al. "Genetic Screens to Identify Plant Stress Genes", Methods in Molecular Biology, 639: 121-139, 2010. Abstract.
Vanholme et al. "The Tify Family Previously Known As ZIM", Trends in Plant Science, 12(6): 239-244, Jun. 2007.
Yanagisawa et al. "Metabolic Engineering With Dof1 Transcription Factor in Plants: Improved Nitrogen Assimilation and Growth Under Low-Nitrogen Conditions", Proc. Natl. Acad. Sci USA, PNAS, 101(20): 7833-7838, May 18, 2004.
Official Action dated May 14, 2020 From the US Patent and Trademark Office Re. U.S. Appl. No. 16/154,833. (27 pages).
Buell et al. "Sequence, Annotation, and Analysis of Synteny between Rice Chromosome 3 and Diverged Grass Species," Genome Research, 15(9):1284-1291, 2005.
Examination Report dated Jul. 16, 2020 From the National Institute of Property of Brazil Re. Application No. PI0812742-5 with an English summary. (6 pages).
Requisition by the Examiner dated Sep. 3, 2020 From the Canadian Intellectual Property Office Re. Application No. 3,019,282. (7 pages).
Final Official Action dated Aug. 17, 2020 From the US Patent and Trademark Office Re. U.S. Appl. No. 16/154,833. (11 pages).
Buell et al. "Probable Nucleoredoxin 1-2. NRX12_ORYSJ" Primary UniProt Database Accession No. Q7Y0F2, Secondary Accession Nos. A0A0P0VZE5, Q0DR93, Q60EC7, Dec. 11, 2019, 13 Pages.

* cited by examiner

POLYNUCLEOTIDES, POLYPEPTIDES ENCODED THEREBY, AND METHODS OF USING SAME FOR INCREASING ABIOTIC STRESS TOLERANCE AND/OR BIOMASS AND/OR YIELD IN PLANTS EXPRESSING SAME

RELATED APPLICATIONS

This application is a continuation of U.S. patent application Ser. No. 15/278,086 filed on Sep. 28, 2016 which is a division of U.S. patent application Ser. No. 14/071,715 filed on Nov. 5, 2013, now U.S. Pat. No. 9,518,267, which is a continuation of U.S. patent application Ser. No. 12/669,975 filed on Jul. 21, 2010, now U.S. Pat. No. 8,686,227, which is a National Phase of PCT Patent Application No. PCT/IL2008/001024 having International Filing Date of Jul. 24, 2008, which claims the benefit of priority under 35 USC § 119(e) of U.S. Provisional Patent Application No. 60/935,046 filed on Jul. 24, 2007. The contents of the above applications are all incorporated by reference as if fully set forth herein in their entirety.

SEQUENCE LISTING STATEMENT

The ASCII file, entitled 76245SequenceListing.txt, created on Dec. 13, 2018, comprising 3,948,312 bytes, submitted concurrently with the filing of this application is incorporated herein by reference.

FIELD AND BACKGROUND OF THE INVENTION

The present invention, in some embodiments thereof, relates to isolated polypeptides and polynucleotides and more particularly, but not exclusively, to methods of using same for increasing tolerance of a plant to abiotic stress, growth, biomass, vigor and/or yield of a plant.

Abiotic stress (ABS; also referred to as "environmental stress") conditions such as salinity, drought, flood, suboptimal temperature and toxic chemical pollution, cause substantial damage to agricultural plants. Most plants have evolved strategies to protect themselves against these conditions. However, if the severity and duration of the stress conditions are too great, the effects on plant development, growth and yield are profound. Furthermore, most of the crop plants are highly susceptible to ABS and thus necessitate optimal growth conditions for commercial crop yields. Continuous exposure to stress causes major alterations in plant's metabolism which ultimately leads to cell death and consequently yield loss. Thus, despite extensive research and intensive crop-protection measures, losses due to abiotic stress conditions remain in the billions of dollars annually.

Drought is a gradual phenomenon, which involves periods of abnormally dry weather that persists long enough to produce serious hydrologic imbalances such as crop damage and water supply shortage. In severe cases, drought can last many years and result in devastating effects on agriculture and water supplies. With burgeoning population and chronic shortage of available fresh water, drought is not only the number one weather-related problem in agriculture, but it also ranks as one of the major natural disasters of all time, causing not only economic damage (e.g., losses from the US drought of 1988 exceeded $40 billion), but also loss of human lives, as in the 1984-1985 drought in the Horn of Africa which led to a famine that killed 750,000 people. Furthermore, drought is associated with increase susceptibility to various diseases.

For most crop plants, the land regions of the world are too arid. In addition, overuse of available water results in increased loss of agriculturally-usable land (desertification), and increase of salt accumulation in soils adds to the loss of available water in soils.

Salinity, high salt levels, affects one in five hectares of irrigated land. This condition is only expected to worsen, further reducing the availability of arable land and crop production, since none of the top five food crops, i.e., wheat, corn, rice, potatoes, and soybean, can tolerate excessive salt. Detrimental effects of salt on plants result from both water deficit which leads to osmotic stress (similar to drought stress) and the effect of excess sodium ions on critical biochemical processes. As with freezing and drought, high salt causes water deficit; and the presence of high salt makes it difficult for plant roots to extract water from their environment. Soil salinity is thus one of the more important variables that determine whether a plant may thrive. In many parts of the world, sizable land areas are uncultivable due to naturally high soil salinity. Thus, salination of soils that are used for agricultural production is a significant and increasing problem in regions that rely heavily on agriculture, and is worsen by over-utilization, over-fertilization and water shortage, typically caused by climatic change and the demands of increasing population. Salt tolerance is of particular importance early in a plant's lifecycle, since evaporation from the soil surface causes upward water movement, and salt accumulates in the upper soil layer where the seeds are placed. On the other hand, germination normally takes place at a salt concentration which is higher than the mean salt level in the whole soil profile.

Germination of many crops is sensitive to temperature. A gene that would enhance germination in hot conditions would be useful for crops that are planted late in the season or in hot climates. In addition, seedlings and mature plants that are exposed to excess heat may experience heat shock, which may arise in various organs, including leaves and particularly fruit, when transpiration is insufficient to overcome heat stress. Heat also damages cellular structures, including organelles and cytoskeleton, and impairs membrane function. Heat shock may produce a decrease in overall protein synthesis, accompanied by expression of heat shock proteins, e.g., chaperones, which are involved in refolding proteins denatured by heat.

Heat stress often accompanies conditions of low water availability. Heat itself is seen as an interacting stress and adds to the detrimental effects caused by water deficit conditions. Water Evaporative demand exhibits near exponential increases with increases in daytime temperatures and can result in high transpiration rates and low plant water potentials. High-temperature damage to pollen almost always occurs in conjunction with drought stress, and rarely occurs under well-watered conditions. Combined stress can alter plant metabolism in novel ways; therefore understanding the interaction between different stresses may be important for the development of strategies to enhance stress tolerance by genetic manipulation.

Excessive chilling conditions, e.g., low, but above freezing, temperatures affect crops of tropical origins, such as soybean, rice, maize, and cotton. Typical chilling damage includes wilting, necrosis, chlorosis or leakage of ions from cell membranes. The underlying mechanisms of chilling sensitivity are not completely understood yet, but probably involve the level of membrane saturation and other physiological deficiencies. For example, photoinhibition of photosynthesis (disruption of photosynthesis due to high light intensities) often occurs under clear atmospheric conditions subsequent to cold late summer/autumn nights. In addition, chilling may lead to yield losses and lower product quality through the delayed ripening of maize.

Water deficit is a common component of many plant stresses. Water deficit occurs in plant cells when the whole plant transpiration rate exceeds the water uptake. In addition to drought, other stresses, such as salinity and low temperature, produce cellular dehydration.

Salt and drought stress signal transduction consist of ionic and osmotic homeostasis signaling pathways. The ionic aspect of salt stress is signaled via the SOS pathway where a calcium-responsive SOS3-SOS2 protein kinase complex controls the expression and activity of ion transporters such as SOS1. The osmotic component of salt stress involves complex plant reactions that overlap with drought and/or cold stress responses.

Common aspects of drought, cold and salt stress response [Reviewed in Xiong and Zhu (2002) Plant Cell Environ. 25: 131-139] include: (a) transient changes in the cytoplasmic calcium levels early in the signaling event [Knight, (2000) Int. Rev. Cytol. 195: 269-324; Sanders et al. (1999) Plant Cell 11: 691-706]; (b) signal transduction via mitogen-activated and/or calcium dependent protein kinases (CDPKs) and protein phosphatases [Merlot et al. (2001) Plant J. 25: 295-303; Tahtiharju and Palva (2001) Plant J. 26: 461-470]; (c) increases in abscisic acid levels in response to stress triggering a subset of responses; (d) inositol phosphates as signal molecules (at least for a subset of the stress responsive transcriptional changes [Xiong et al. (2001) Genes Dev. 15: 1971-1984]; (e) activation of phospholipases which in turn generates a diverse array of second messenger molecules, some of which might regulate the activity of stress responsive kinases [e.g., phospholipase D; Frank et al. (2000) Plant Cell 12: 111-124]; (f) induction of late embryogenesis abundant (LEA) type genes including the CRT/DRE responsive COR/RD genes; (g) increased levels of antioxidants and compatible osmolytes such as proline and soluble sugars [Hasegawa et al. (2000) Annu. Rev. Plant Mol. Plant Physiol. 51: 463-499)]; and (h) accumulation of reactive oxygen species such as superoxide, hydrogen peroxide, and hydroxyl radicals.

Abscisic acid biosynthesis is regulated by osmotic stress at multiple steps. Both ABA-dependent and -independent osmotic stress signaling first modify constitutively expressed transcription factors, leading to the expression of early response transcriptional activators, which then activate downstream stress tolerance effector genes.

Several genes which increase tolerance to cold or salt stress can also improve drought stress protection, these include for example, the transcription factor AtCBF/DREB1, OsCDPK7 (Saijo et al. 2000, Plant J. 23: 319-327) or AVP1 (a vacuolar pyrophosphatase-proton pump, Gaxiola et al. 2001, Proc. Natl. Acad. Sci. USA 98: 11444-11449).

Developing stress-tolerant plants is a strategy that has the potential to solve or mediate at least some of these problems. However, traditional plant breeding strategies used to develop new lines of plants that exhibit tolerance to ABS are relatively inefficient since they are tedious, time consuming and of unpredictable outcome. Furthermore, limited germplasm resources for stress tolerance and incompatibility in crosses between distantly related plant species represent significant problems encountered in conventional breeding. Additionally, the cellular processes leading to ABS tolerance are complex in nature and involve multiple mechanisms of cellular adaptation and numerous metabolic pathways.

Genetic engineering efforts, aimed at conferring abiotic stress tolerance to transgenic crops, have been described in the art. Studies by Apse and Blumwald (Curr Opin Biotechnol. 13:146-150, 2002), Quesada et al. (Plant Physiol. 130: 951-963, 2002), Holmstrom et al. (Nature 379: 683-684, 1996), Xu et al. (Plant Physiol 110: 249-257, 1996), Pilon-Smits and Ebskamp (Plant Physiol 107: 125-130, 1995) and Tarczynski et al. (Science 259: 508-510, 1993) have all attempted at generating stress tolerant plants.

In addition, several U.S. patents and patent applications also describe polynucleotides associated with stress tolerance and their use in generating stress tolerant plants. U.S. Pat. Nos. 5,296,462 and 5,356,816 describe transforming plants with polynucleotides encoding proteins involved in cold adaptation in *Arabidopsis thaliana* for promoting cold tolerance.

U.S. Pat. No. 6,670,528 describes transforming plants with polynucleotides encoding polypeptides binding to stress responsive elements for promoting tolerance to abiotic stress.

U.S. Pat. No. 6,720,477 describes transforming plants with a polynucleotide encoding a signal transduction stress-related protein, capable of increasing tolerance of the transformed plants to abiotic stress.

U.S. application Ser. Nos. 09/938,842 and 10/342,224 describe abiotic stress-related genes and their use to confer upon plants tolerance to abiotic stress.

U.S. application Ser. No. 10/231,035 describes overexpressing a molybdenum cofactor sulfurase in plants for increasing tolerance to abiotic stress.

WO2004/104162 to Evogene Ltd. teaches polynucleotide sequences and methods of utilizing same for increasing the tolerance of a plant to abiotic stresses and/or increasing the biomass of a plant.

WO2007/020638 to Evogene Ltd. teaches polynucleotide sequences and methods of utilizing same for increasing the tolerance of a plant to abiotic stresses and/or increasing the biomass, vigor and/or yield of a plant.

WO2007/049275 to Evogene Ltd. teaches isolated polypeptides, polynucleotides encoding same for increasing tolerance of a plant to abiotic stress, and/or for increasing biomass, vigor and/or yield of a plant.

Additional background art includes U.S. Patent Appl. Nos. 20060183137A1 A1 and 20030056249A1.

SUMMARY OF THE INVENTION

According to an aspect of some embodiments of the present invention there is provided a method of increasing tolerance of a plant to abiotic stress, the method comprising expressing within the plant an exogenous polynucleotide encoding a polypeptide comprising an amino acid sequence at least 90% homologous to the amino acid sequence selected from the group consisting of SEQ ID NOs:201, 207, 212, 202-206, 208-211, 213-391, 1655, 961-1529, and 1660-1663, thereby increasing the tolerance of the plant to abiotic stress.

According to an aspect of some embodiments of the present invention there is provided a method of increasing tolerance of a plant to abiotic stress, the method comprising expressing within the plant an exogenous polynucleotide encoding a polypeptide comprising an amino acid sequence selected from the group consisting of SEQ ID NOs:201, 207, 212, 202-206, 208-211, 213-391, 1655, 961-1529, and 1660-1663, thereby increasing the tolerance of the plant to abiotic stress.

According to an aspect of some embodiments of the present invention there is provided a method of increasing biomass, growth rate, vigor and/or yield of a plant, the method comprising expressing within the plant an exogenous polynucleotide encoding a polypeptide comprising an amino acid sequence at least 90% homologous to the amino acid sequence selected from the group consisting of SEQ ID NOs:201, 207, 212, 202-206, 208-211, 213-391, 1655, 961-1529, and 1660-1663, thereby increasing the biomass, growth rate, vigor and/or yield of the plant.

According to an aspect of some embodiments of the present invention there is provided a method of increasing biomass, growth rate, vigor and/or yield of a plant, the method comprising expressing within the plant an exogenous polynucleotide encoding a polypeptide comprising an amino acid sequence selected from the group consisting of SEQ ID NOs:201, 207, 212, 202-206, 208-211, 213-391, 1655, 961-1529, and 1660-1663, thereby increasing the biomass, growth rate, vigor and/or yield of the plant.

According to an aspect of some embodiments of the present invention there is provided an isolated polynucleotide comprising a nucleic acid sequence at least 90% identical to the nucleic acid sequence selected from the group consisting of SEQ ID NOs:1530, 1561, 1532, 1531, 1562, 1533, 1538, 1549, 1665, 1566, 1554, 1563, 1557, 1564, 1534, 1536, 1552, 1553, 1666, 1547, 1548, 1556, 1559, 1560, 1654, 1555, 1540, 1543, 1668, 1539, 1550, 1558, 1565, 1541, 1667, 1542, 1544, 1537, 1551, 1545, 1-200, 1653, 392-960, and 1656-1659.

According to an aspect of some embodiments of the present invention there is provided an isolated polynucleotide comprising a nucleic acid sequence selected from the group consisting of SEQ ID NOs:1530, 1561, 1532, 1531, 1562, 1533, 1538, 1549, 1665, 1566, 1554, 1563, 1557, 1564, 1534, 1536, 1552, 1553, 1666, 1547, 1548, 1556, 1559, 1560, 1654, 1555, 1540, 1543, 1668, 1539, 1550, 1558, 1565, 1541, 1667, 1542, 1544, 1537, 1551, 1545, 1-200, 1653, 392-960, and 1656-1659.

According to an aspect of some embodiments of the present invention there is provided a nucleic acid construct comprising the isolated polynucleotide and a promoter for directing transcription of the nucleic acid sequence.

According to an aspect of some embodiments of the present invention there is provided an isolated polypeptide, comprising an amino acid sequence at least 90% homologous to the amino acid sequence selected from the group consisting of SEQ ID NOs:201, 207, 212, 202-206, 208-211, 213-391, 1655, 961-1529, and 1660-1663.

According to an aspect of some embodiments of the present invention there is provided an isolated polypeptide, comprising an amino acid sequence selected from the group consisting of SEQ ID NOs:201, 207, 212, 202-206, 208-211, 213-391, 1655, 961-1529, and 1660-1663.

According to an aspect of some embodiments of the present invention there is provided a plant cell comprising an exogenous polypeptide comprising an amino acid sequence at least 90% homologous to the amino acid sequence selected from the group consisting of SEQ ID NOs:201, 207, 212, 202-206, 208-211, 213-391, 1655, 961-1529, and 1660-1663.

According to an aspect of some embodiments of the present invention there is provided a plant cell comprising an exogenous polypeptide comprising an amino acid sequence selected from the group consisting of SEQ ID NOs:201, 207, 212, 202-206, 208-211, 213-391, 1655, 961-1529, and 1660-1663.

According to an aspect of some embodiments of the present invention there is provided a plant cell comprising an exogenous polynucleotide comprising a nucleic acid sequence at least 90% homologous to the nucleic acid sequence selected from the group consisting of SEQ ID NOs:1530, 1561, 1532, 1531, 1562, 1533, 1538, 1549, 1665, 1566, 1554, 1563, 1557, 1564, 1534, 1536, 1552, 1553, 1666, 1547, 1548, 1556, 1559, 1560, 1654, 1555, 1540, 1543, 1668, 1539, 1550, 1558, 1565, 1541, 1667, 1542, 1544, 1537, 1551, 1545, 1-200, 1653, 392-960, and 1656-1659.

According to an aspect of some embodiments of the present invention there is provided a plant cell comprising an exogenous polynucleotide comprising a nucleic acid sequence selected from the group consisting of SEQ ID NOs:1530, 1561, 1532, 1531, 1562, 1533, 1538, 1549, 1665, 1566, 1554, 1563, 1557, 1564, 1534, 1536, 1552, 1553, 1666, 1547, 1548, 1556, 1559, 1560, 1654, 1555, 1540, 1543, 1668, 1539, 1550, 1558, 1565, 1541, 1667, 1542, 1544, 1537, 1551, 1545, 1-200, 1653, 392-960, and 1656-1659. According to some embodiments of the invention, the nucleic acid sequence is selected from the group consisting of SEQ ID NOs:1530, 1561, 1532, 1531, 1562, 1533, 1538, 1549, 1665, 1566, 1554, 1563, 1557, 1564, 1534, 1536, 1552, 1553, 1666, 1547, 1548, 1556, 1559, 1560, 1654, 1555, 1540, 1543, 1668, 1539, 1550, 1558, 1565, 1541, 1667, 1542, 1544, 1537, 1551, 1545, 1-200, 1653, 392-960, and 1656-1659.

According to some embodiments of the invention, the polynucleotide is selected from the group consisting of SEQ ID NOs:1530, 1561, 1532, 1531, 1562, 1533, 1538, 1549, 1665, 1566, 1554, 1563, 1557, 1564, 1534, 1536, 1552, 1553, 1666, 1547, 1548, 1556, 1559, 1560, 1654, 1555, 1540, 1543, 1668, 1539, 1550, 1558, 1565, 1541, 1667, 1542, 1544, 1537, 1551, 1545, 1-200, 1653, 392-960, and 1656-1659.

According to some embodiments of the invention, the amino acid sequence is selected from the group consisting of SEQ ID NOs:201, 207, 212, 202-206, 208-211, 213-391, 1655, 961-1529, and 1660-1663.

According to some embodiments of the invention, the polypeptide is selected from the group consisting of SEQ ID NOs:201, 207, 212, 202-206, 208-211, 213-391, 1655, 961-1529, and 1660-1663.

According to some embodiments of the invention, the plant cell forms a part of a plant.

According to some embodiments of the invention, the abiotic stress is selected from the group consisting of salinity, drought, water deprivation, low temperature, high temperature, heavy metal toxicity, anaerobiosis, nutrient deficiency, nutrient excess, atmospheric pollution and UV irradiation.

According to some embodiments of the invention, the method further comprising growing the plant expressing the exogenous polynucleotide under the abiotic stress.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 2a—An image of a photograph of plants taken following 12 days on agar plates. FIG. 2b—An image of root analysis in which the length of the root measured is represented by the red arrow.

DESCRIPTION OF SPECIFIC EMBODIMENTS OF THE INVENTION

Figure 1:
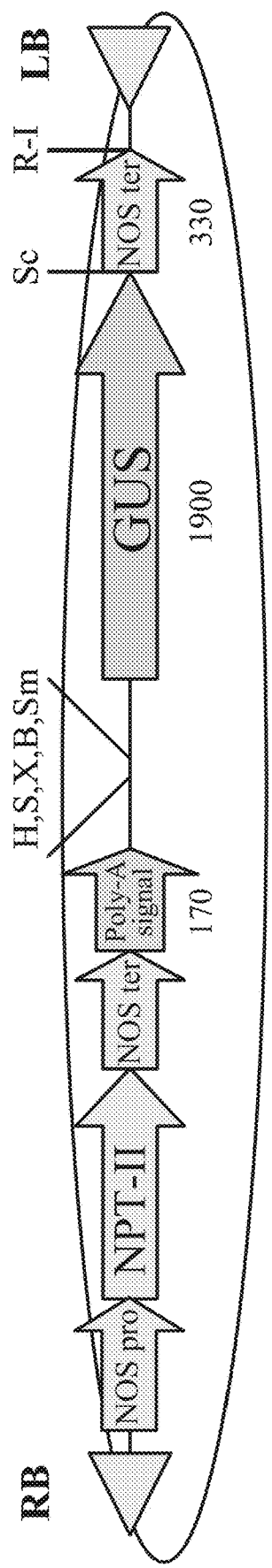
FIG. 1 is a schematic illustration of the pGI binary plasmid used for expressing the isolated polynucleotide sequences of the invention. RB—T-DNA right border; LB—T-DNA left border; H—HindIII restriction enzyme; X—XbaI restriction enzyme; B—BamHI restriction enzyme; S—SalI restriction enzyme; Sm—SmaI restriction enzyme; R-I—EcoRI restriction enzyme; Sc—SacI/SstI/Ecl136II; (numbers)—Length in base-pairs; NOS pro=nopaline synthase promoter; NPT-II=neomycin phosphotransferase gene; NOS ter=nopaline synthase terminator; Poly-A signal (polyadenylation signal); GUSintron—the GUS reporter gene (coding sequence and intron) The isolated polynucleotide sequences of the invention were cloned into the vector while replacing the GUSintron reporter gene.

The present invention, in some embodiments thereof, relates to isolated polypeptides and polynucleotides encoding same, and more particularly, but not exclusively, to methods of using same for increasing tolerance to abiotic stress, growth rate, yield, biomass and/or vigor of a plant.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

While reducing the invention to practice, the present inventors have identified novel polypeptides and polynucleotides which can be used to increase tolerance to abiotic stress, and improve growth rate, biomass, yield and/or vigor of a plant.

Thus, as shown in the Examples section which follows, the present inventors have employed a bioinformatics approach which combines clustering and assembly of sequences from databases of the *Arabidopsis*, rice and other publicly available plant genomes, expressed sequence tags (ESTs), protein and pathway databases and QTL information with a digital expression profile ("electronic Northern Blot") and identified polynucleotides and polypeptides which can increase tolerance to abiotic stress, and improve growth, biomass, yield and vigor (SEQ ID NOs:1-200 and 1653 for polynucleotides; SEQ ID NOs:201-391 and 1655 for polypeptides; Table 1, Example 1). Putative ABST orthologs from monocot species were identified by alignments of ortholog sequences and digital expression profiles (SEQ ID NOs:392-960, 1656-1659 for polynucleotides; SEQ ID NOs:961-1529, 1660-1663 for polypeptides; Table 2, Example 1). As is further described in Tables 3 and 4 of the Examples section which follows, representative polynucleotides were cloned (polynucleotide SEQ ID NOs:1530, 1538, 1532, 1549, 1665, 1566, 1554, 1563, 1557, 1561, 1564, 1534, 1536, 1552, 1553, 1666, 1547, 1548, 1556, 1559, 1560, 1654, 1555, 1540, 1543 and 1668). Additional polynucleotides having optimized nucleic acid sequences were prepared (polynucleotide SEQ ID NOs:1531, 1539, 1533, 1550, 1558, 1562, 1565, 1541, 1667, 1542, 1544, 1537, 1551 and 1545). As is further described in the Examples section which follows, transgenic plants exogenously expressing the cloned and/or optimized polynucleotides of the invention were generated. As shown in Tables 5-76, these plants exhibit increased seedling weight, root coverage, root length, and relative growth rate when grown under osmotic stress (in the presence of 25% PEG), nitrogen deficiency (in the presence of 0.75 mM Nitrogen) or regular conditions. In addition, as shown in Tables 77-188, plants exogenously expressing the polynucleotides of the invention exhibit increased rosette area, rosette diameter, leaf average area, relative growth rate of the above, plants biomass, plant seed yield, 1000 seed weight, and harvest index when grown under salinity stress or normal conditions. Altogether, these results suggest the use of the novel polynucleotides and polypeptides of the invention for increasing abiotic stress tolerance, and improving growth rate biomass, vigor and/or yield of a plant.

Thus, according to one aspect of the invention, there is provided a method of increasing abiotic stress tolerance, growth rate, biomass, yield and/or vigor of a plant. The method is effected by expressing within the plant an exogenous polynucleotide encoding a polypeptide comprising an amino acid sequence at least 60% homologous to the amino acid sequence selected from the group consisting of SEQ ID NOs:201, 207, 212, 202-206, 208-211, 213-391, 1655, 961-1529, and 1660-1663.

The phrase "abiotic stress" as used herein refers to any adverse effect on metabolism, growth, reproduction and/or viability of a plant. Accordingly, abiotic stress can be induced by suboptimal environmental growth conditions such as, for example, salinity, water deprivation, water deficit, drought, flooding, freezing, low or high temperature (e.g., chilling or excessive heat), toxic chemical pollution, heavy metal toxicity, anaerobiosis, nutrient deficiency, nutrient excess, atmospheric pollution or UV irradiation. The implications of abiotic stress are discussed in the Background section.

The phrase "abiotic stress tolerance" as used herein refers to the ability of a plant to endure an abiotic stress without suffering a substantial alteration in metabolism, growth, productivity and/or viability.

As used herein the phrase "plant biomass" refers to the amount (measured in grams of air-dry or dry tissue) of a tissue produced from the plant in a growing season, which could also determine or affect the plant yield or the yield per growing area.

As used herein the phrase "plant yield" refers to the amount (as determined by weight, volume or size) or quantity (numbers) of tissue produced or harvested per plant or per growing season. Hence increased yield could affect the economic benefit one can obtain from the plant in a certain growing area and/or growing time.

As used herein the phrase "plant vigor" refers to the amount (measured by weight) of tissue produced by the plant in a given time. Hence increase vigor could determine or affect the plant yield or the yield per growing time or growing area.

As used herein the term "increasing" refers to at least about 2%, at least about 3%, at least about 4%, at least about 5%, at least about 10%, at least about 15%, at least about 20%, at least about 30%, at least about 40%, at least about 50%, at least about 60%, at least about 70%, at least about 80% or greater increase in plant abiotic stress tolerance, growth, biomass, yield and/or vigor as compared to a native plant [i.e., a plant not modified with the biomolecules (polynucleotide or polypeptides) of the invention, e.g., a non-transformed plant of the same species which is grown under the same growth conditions).

As used herein, the phrase "exogenous polynucleotide" refers to a heterologous nucleic acid sequence which may not be naturally expressed within the plant or which over-expression in the plant is desired. The exogenous polynucleotide may be introduced into the plant in a stable or transient manner, so as to produce a ribonucleic acid (RNA) molecule and/or a polypeptide molecule. It should be noted that the exogenous polynucleotide may comprise a nucleic acid sequence which is identical or partially homologous to an endogenous nucleic acid sequence of the plant.

As mentioned, the exogenous polynucleotide of the invention encodes a polypeptide having an amino acid sequence at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more say 100% homologous to the amino acid sequence selected from the group consisting of SEQ ID NOs:201, 207, 212, 202-206, 208-211, 213-391, 1655, 961-1529, and 1660-1663.

Homology (e.g., percent homology) can be determined using any homology comparison software, including for example, the BlastP or TBLASTN software of the National Center of Biotechnology Information (NCBI) such as by using default parameters, when starting from a polypeptide sequence; or the tBLASTX algorithm (available via the NCBI) such as by using default parameters, which compares the six-frame conceptual translation products of a nucleotide query sequence (both strands) against a protein sequence database.

Homologous sequences include both orthologous and paralogous sequences. The term "paralogous" relates to gene-duplications within the genome of a species leading to paralogous genes. The term "orthologous" relates to homologous genes in different organisms due to ancestral relationship.

One option to identify orthologues in monocot plant species is by performing a reciprocal blast search. This may be done by a first blast involving blasting the sequence-of-interest against any sequence database, such as the publicly available NCBI database which may be found at: Hypertext Transfer Protocol://World Wide Web (dot) ncbi (dot) nlm (dot) nih (dot) gov. If orthologues in rice were sought, the sequence-of-interest would be blasted against, for example, the 28,469 full-length cDNA clones from *Oryza sativa* Nipponbare available at NCBI. The blast results may be filtered. The full-length sequences of either the filtered results or the non-filtered results are then blasted back (second blast) against the sequences of the organism from which the sequence-of-interest is derived. The results of the first and second blasts are then compared. An orthologue is identified when the sequence resulting in the highest score (best hit) in the first blast identifies in the second blast the query sequence (the original sequence-of-interest) as the best hit. Using the same rational a paralogue (homolog to a gene in the same organism) is found. In case of large sequence families, the ClustalW program may be used [Hypertext Transfer Protocol://World Wide Web (dot) ebi (dot) ac (dot) uk/Tools/clustalw2/index (dot) html], followed by a neighbor-joining tree (Hypertext Transfer Protocol://en (dot) wikipedia (dot) org/wiki/Neighbor-joining) which helps visualizing the clustering.

According to some embodiments of the invention, the exogenous polynucleotide encodes a polypeptide consisting of the amino acid sequence set forth by SEQ ID NO:201, 207, 212, 202-206, 208-211, 213-391, 1655, 961-1529, 1660-1662 or 1663.

According to some embodiments of the invention the exogenous polynucleotide comprises a nucleic acid sequence which is at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 93%, at least about 94%, at least about 95%, at least about 96%, at least about 97%, at least about 98%, at least about 99%, e.g., 100% identical to the nucleic acid sequence selected from the group consisting of SEQ ID NOs:1530, 1561, 1532, 1531, 1562, 1533, 1538, 1549, 1665, 1566, 1554, 1563, 1557, 1564, 1534, 1536, 1552, 1553, 1666, 1547, 1548, 1556, 1559, 1560, 1654, 1555, 1540, 1543, 1668, 1539, 1550, 1558, 1565, 1541, 1667, 1542, 1544, 1537, 1551, 1545, 1-200, 1653, 392-960, and 1656-1659.

Identity (e.g., percent homology) can be determined using any homology comparison software, including for example, the BlastN software of the National Center of Biotechnology Information (NCBI) such as by using default parameters.

According to some embodiments of the invention the exogenous polynucleotide is at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 93%, at least about 94%, at least about 95%, at least about 96%, at least about 97%, at least about 98%, at least about 99%, e.g., 100% identical to the polynucleotide selected from the group consisting of SEQ ID NOs:1530, 1561, 1532, 1531, 1562, 1533, 1538, 1549, 1665, 1566, 1554, 1563, 1557, 1564, 1534, 1536, 1552, 1553, 1666, 1547, 1548, 1556, 1559, 1560, 1654, 1555, 1540, 1543, 1668, 1539, 1550, 1558, 1565, 1541, 1667, 1542, 1544, 1537, 1551, 1545, 1-200, 1653, 392-960, and 1656-1659.

According to some embodiments of the invention the exogenous polynucleotide is set forth by SEQ ID NO:1530, 1561, 1532, 1531, 1562, 1533, 1538, 1549, 1665, 1566, 1554, 1563, 1557, 1564, 1534, 1536, 1552, 1553, 1666, 1547, 1548, 1556, 1559, 1560, 1654, 1555, 1540, 1543, 1668, 1539, 1550, 1558, 1565, 1541, 1667, 1542, 1544, 1537, 1551, 1545, 1-200, 1653, 392-960, and 1656-1658 or 1659.

As used herein the term "polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (identified or isolated) from a chromosome and thus it represents a contiguous portion of a chromosome.

As used herein the phrase "composite polynucleotide sequence" refers to a sequence, which is at least partially complementary and at least partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

Nucleic acid sequences encoding the polypeptides of the present invention may be optimized for expression. A non-limiting example of an optimized nucleic acid sequence is provided in SEQ ID NO:1531, which encodes the polypeptide comprising the amino acid sequence set forth by SEQ ID NO:201. Examples of such sequence modifications include, but are not limited to, an altered G/C content to more closely approach that typically found in the plant species of interest, and the removal of codons atypically found in the plant species commonly referred to as codon optimization.

The phrase "codon optimization" refers to the selection of appropriate DNA nucleotides for use within a structural gene or fragment thereof that approaches codon usage within the plant of interest. Therefore, an optimized gene or nucleic acid sequence refers to a gene in which the nucleotide sequence of a native or naturally occurring gene has been modified in order to utilize statistically-preferred or statistically-favored codons within the plant. The nucleotide sequence typically is examined at the DNA level and the coding region optimized for expression in the plant species determined using any suitable procedure, for example as described in Sardana et al. (1996, Plant Cell Reports 15:677-681). In this method, the standard deviation of codon usage, a measure of codon usage bias, may be calculated by first finding the squared proportional deviation of usage of each codon of the native gene relative to that of highly expressed plant genes, followed by a calculation of the average squared deviation. The formula used is: 1 SDCU=n=1 N [(Xn−Yn)/Yn] 2/N, where Xn refers to the frequency of usage of codon n in highly expressed plant genes, where Yn to the frequency of usage of codon n in the gene of interest and N refers to the total number of codons in the gene of interest. A Table of codon usage from highly expressed genes of dicotyledonous plants is compiled using the data of Murray et al. (1989, Nuc Acids Res. 17:477-498).

One method of optimizing the nucleic acid sequence in accordance with the preferred codon usage for a particular plant cell type is based on the direct use, without performing any extra statistical calculations, of codon optimization Tables such as those provided on-line at the Codon Usage Database through the NIAS (National Institute of Agrobiological Sciences) DNA bank in Japan (Hypertext Transfer Protocol://World Wide Web (dot) kazusa (dot) or (dot) jp/codon/). The Codon Usage Database contains codon usage Tables for a number of different species, with each codon usage Table having been statistically determined based on the data present in Genbank.

By using the above Tables to determine the most preferred or most favored codons for each amino acid in a particular species (for example, rice), a naturally-occurring nucleotide sequence encoding a protein of interest can be codon optimized for that particular plant species. This is effected by replacing codons that may have a low statistical incidence in the particular species genome with corresponding codons, in regard to an amino acid, that are statistically more favored. However, one or more less-favored codons may be selected to delete existing restriction sites, to create new ones at potentially useful junctions (5' and 3' ends to add signal peptide or termination cassettes, internal sites that might be used to cut and splice segments together to produce a correct full-length sequence), or to eliminate nucleotide sequences that may negatively effect mRNA stability or expression.

The naturally-occurring encoding nucleotide sequence may already, in advance of any modification, contain a number of codons that correspond to a statistically-favored codon in a particular plant species. Therefore, codon optimization of the native nucleotide sequence may comprise determining which codons, within the native nucleotide sequence, are not statistically-favored with regards to a particular plant, and modifying these codons in accordance with a codon usage table of the particular plant to produce a codon optimized derivative. A modified nucleotide sequence may be fully or partially optimized for plant codon usage provided that the protein encoded by the modified nucleotide sequence is produced at a level higher than the protein encoded by the corresponding naturally occurring or native gene. Construction of synthetic genes by altering the codon usage is described in for example PCT Patent Application 93/07278.

Thus, the invention encompasses nucleic acid sequences described hereinabove; fragments thereof, sequences hybridizable therewith, sequences homologous thereto, sequences encoding similar polypeptides with different codon usage, altered sequences characterized by mutations, such as deletion, insertion or substitution of one or more nucleotides, either naturally occurring or man induced, either randomly or in a targeted fashion.

The invention provides an isolated polypeptide having an amino acid sequence at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 93%, at least about 94%, at least about 95%, at least about 96%, at least about 97%, at least about 98%, at least about 99%, or more say 100% homologous to an amino acid sequence selected from the group consisting of SEQ ID NO:201, 207, 212, 202-206, 208-211, 213-391, 1655, 961-1529, and 1660-1663.

According to some embodiments of the invention, the polypeptide is set forth by SEQ ID NO:201, 207, 212, 202-206, 208-211, 213-391, 1655, 961-1529, and 1660-1662 or 1663.

The invention also encompasses fragments of the above described polypeptides and polypeptides having mutations, such as deletions, insertions or substitutions of one or more amino acids, either naturally occurring or man induced, either randomly or in a targeted fashion.

The term "plant" as used herein encompasses whole plants, ancestors and progeny of the plants and plant parts, including seeds, shoots, stems, roots (including tubers), and plant cells, tissues and organs. The plant may be in any form including suspension cultures, embryos, meristematic regions, callus tissue, leaves, gametophytes, sporophytes, pollen, and microspores. Plants that are particularly useful in the methods of the invention include all plants which belong to the superfamily Viridiplantae, in particular monocotyledonous and dicotyledonous plants including a fodder or forage legume, ornamental plant, food crop, tree, or shrub selected from the list comprising Acacia spp., Acer spp., Actinidia spp., Aesculus spp., Agathis australis, Albizia amara, Alsophila tricolor, Andropogon spp., Arachis spp, Areca catechu, Astelia fragrans, Astragalus cicer, Baikiaea plurijuga, Betula spp., Brassica spp., Bruguiera gymnorrhiza, Burkea africana, Butea frondosa, Cadaba farinosa, Calliandra spp, Camellia sinensis, Canna indica, Capsicum spp., Cassia spp., Centroema pubescens, Chacoomeles spp., Cinnamomum cassia, Coffea arabica, Colophospermum mopane, Coronillia varia, Cotoneaster serotina, Crataegus spp., Cucumis spp., Cupressus spp., Cyathea dealbata, Cydonia oblonga, Cryptomeria japonica, Cymbopogon spp., Cynthea dealbata, Cydonia oblonga, Dalbergia monetaria, Davallia divaricata, Desmodium spp., Dicksonia squarosa, Dibeteropogon amplectens, Dioclea spp, Dolichos spp., Dorycnium rectum, Echinochloa pyramidalis, Ehraffia spp., Eleusine coracana, Eragrestis spp., Erythrina spp., Eucalypfus spp., Euclea schimperi, Eulalia vi/losa, Pagopyrum spp., Feijoa sellowlana, Fragaria spp., Flemingia spp, Freycinetia banksli, Geranium thunbergii, GinAgo biloba, Glycine javanica, Gliricidia spp, Gossypium hirsutum, Grevillea spp., Guibourtia coleosperma, Hedysarum spp., Hemaffhia altissima, Heteropogon contoffus, Hordeum vulgare, Hyparrhenia rufa, Hypericum erectum, Hypeffhelia dissolute, Indigo incamata, Iris spp., Leptarrhena pyrolifolia, Lespediza spp., Lettuca spp., Leucaena leucocephala, Loudetia simplex, Lotonus bainesli, Lotus spp., Macrotyloma axillare, Malus spp., Manihot esculenta, Medicago saliva, Metasequoia glyptostroboides, Musa sapientum, Nicotianum spp., Onobrychis spp., Ornithopus spp., Oryza spp., Peltophorum africanum, Pennisetum spp., Persea gratissima, Petunia spp., Phaseolus spp., Phoenix canariensis, Phormium cookianum, Photinia spp., Picea glauca, Pinus spp., Pisum sativam, Podocarpus totara, Pogonarthria fleckii, Pogonaffhria squarrosa, Populus spp., Prosopis cineraria, Pseudotsuga menziesii, Pterolobium stellatum, Pyrus communis, Quercus spp., Rhaphiolepsis umbellata, Rhopalostylis sapida, Rhus natalensis, Ribes grossularia, Ribes spp., Robinia pseudoacacia, Rosa spp., Rubus spp., Salix spp., Schyzachyrium sanguineum, Sciadopitys vefficillata, Sequoia sempervirens, Sequoiadendron giganteum, Sorghum bicolor, Spinacia spp., Sporobolus fimbriatus, Stiburus alopecuroides, Stylosanthos humilis, Tadehagi spp, Taxodium distichum, Themeda triandra, Trifolium spp., Triticum spp., Tsuga heterophylla, Vaccinium spp., Vicia spp., Vitis vinifera, Watsonia pyramidata, Zantedeschia aethiopica, Zea mays, amaranth, artichoke, asparagus, broccoli, Brussels sprouts, cabbage, canola, carrot, cauliflower, celery, collard greens, flax, kale, lentil, oilseed rape, okra, onion, potato, rice, soybean, straw, sugar beet, sugar cane, sunflower, tomato, squash tea, maize, wheat, barely, rye, oat, peanut, pea, lentil and alfalfa, cotton, rapeseed, canola, pepper, sunflower, tobacco, eggplant, eucalyptus, a tree, an ornamental plant, a perennial grass and a forage crop. Alternatively algae and other non-Viridiplantae can be used for the methods of the present invention.

According to some embodiments of the invention, the plant used by the method of the invention is a crop plant such as rice, maize, wheat, barley, peanut, potato, sesame, olive tree, palm oil, banana, soybean, sunflower, canola, sugarcane, alfalfa, millet, leguminosae (bean, pea), flax, lupinus, rapeseed, tobacco, popular and cotton.

Expressing the exogenous polynucleotide of the invention within the plant can be effected by transforming one or more cells of the plant with the exogenous polynucleotide, followed by generating a mature plant from the transformed cells and cultivating the mature plant under conditions suitable for expressing the exogenous polynucleotide within the mature plant.

According to some embodiments of the invention, the transformation is effected by introducing to the plant cell a nucleic acid construct which includes the exogenous polynucleotide of some embodiments of the invention and at least one promoter capable of directing transcription of the exogenous polynucleotide in the plant cell. Further details of suitable transformation approaches are provided hereinbelow.

As used herein, the term "promoter" refers to a region of DNA which lies upstream of the transcriptional initiation site of a gene to which RNA polymerase binds to initiate transcription of RNA. The promoter controls where (e.g., which portion of a plant) and/or when (e.g., at which stage or condition in the lifetime of an organism) the gene is expressed.

Any suitable promoter sequence can be used by the nucleic acid construct of the present invention. According to some embodiments of the invention, the promoter is a constitutive promoter, a tissue-specific, or an abiotic stress-inducible promoter.

Suitable constitutive promoters include, for example, CaMV 35S promoter (SEQ ID NO:1546; Odell et al., Nature 313:810-812, 1985); Arabidopsis At6669 promoter (SEQ ID NO:1652; see PCT Publication No. WO04081173A2); maize Ubi 1 (Christensen et al., Plant Sol. Biol. 18:675-689, 1992); rice actin (McElroy et al., Plant Cell 2:163-171, 1990); pEMU (Last et al., Theor. Appl. Genet. 81:581-588, 1991); CaMV 19S (Nilsson et al., Physiol. Plant 100:456-462, 1997); GOS2 (de Pater et al., Plant J November; 2(6):837-44, 1992); ubiquitin (Christensen et al., Plant Mol. Biol. 18: 675-689, 1992); Rice cyclophilin (Bucholz et al., Plant Mol Biol. 25(5):837-43, 1994); Maize H3 histone (Lepetit et al., Mol. Gen. Genet. 231: 276-285, 1992); Actin 2 (An et al., Plant J. 10(1); 107-121, 1996), constitutive root tip CT2 promoter (SEQ ID NO:1535; see also PCT application No. IL/2005/000627) and Synthetic Super MAS (Ni et al., The Plant Journal 7: 661-76, 1995). Other constitutive promoters include those in U.S. Pat. Nos. 5,659,026, 5,608, 149; 5,608,144; 5,604,121; 5,569,597: 5,466,785; 5,399, 680; 5,268,463; and 5,608,142.

Suitable tissue-specific promoters include, but not limited to, leaf-specific promoters [such as described, for example, by Yamamoto et al., Plant J. 12:255-265, 1997; Kwon et al., Plant Physiol. 105:357-67, 1994; Yamamoto et al., Plant Cell Physiol. 35:773-778, 1994; Gotor et al., Plant J. 3:509-18, 1993; Orozco et al., Plant Mol. Biol. 23:1129-1138, 1993; and Matsuoka et al., Proc. Natl. Acad. Sci. USA 90:9586-9590, 1993], seed-preferred promoters [e.g., from seed specific genes (Simon, et al., Plant Mol. Biol. 5. 191, 1985; Scofield, et al., J. Biol. Chem. 262: 12202, 1987; Baszczynski, et al., Plant Mol. Biol. 14: 633, 1990), Brazil Nut albumin (Pearson' et al., Plant Mol. Biol. 18: 235-245, 1992), legumin (Ellis, et al. Plant Mol. Biol. 10: 203-214, 1988), Glutelin (rice) (Takaiwa, et al., Mol. Gen. Genet. 208: 15-22, 1986; Takaiwa, et al., FEBS Letts. 221: 43-47, 1987), Zein (Matzke et al., Plant Mol Biol, 143). 323-32 1990), napA (Stalberg, et al., Planta 199: 515-519, 1996), Wheat SPA (Albani et al, Plant Cell, 9: 171-184, 1997), sunflower oleosin (Cummins, et al., Plant Mol. Biol. 19: 873-876, 1992)], endosperm specific promoters [e.g., wheat LMW and HMW, glutenin-1 (Mol Gen Genet 216:81-90, 1989; NAR 17:461-2), wheat a, b and g gliadins (EMBO3:1409-15, 1984), Barley ltrl promoter, barley Bl, C, D hordein (Theor Appl Gen 98:1253-62, 1999; Plant J 4:343-55, 1993; Mol Gen Genet 250:750-60, 1996), Barley DOF (Mena et al., The Plant Journal, 116(1): 53-62, 1998), Biz2 (EP99106056.7), Synthetic promoter (Vicente-Carbajosa et al., Plant J. 13: 629-640, 1998), rice prolamin NRP33, rice-globulin Glb-1 (Wu et al., Plant Cell Physiology 39(8) 885-889, 1998), rice alpha-globulin REB/OHP-1 (Nakase et al. Plant Mol. Biol. 33: 513-S22, 1997), rice ADP-glucose PP (Trans Res 6:157-68, 1997), maize ESR gene family (Plant J 12:235-46, 1997), sorgum gamma-kafirin (PMB 32:1029-35, 1996)], embryo specific promoters [e.g., rice OSH1 (Sato et al., Proc. Nati. Acad. Sci. USA, 93: 8117-8122), KNOX (Postma-Haarsma of al, Plant Mol. Biol. 39:257-71, 1999), rice oleosin (Wu et at, J. Biochem., 123:386, 1998)], and flower-specific promoters [e.g., AtPRP4, chalene synthase (chsA) (Van der Meer, et al., Plant Mol. Biol. 15, 95-109, 1990), LAT52 (Twell et al., Mol. Gen Genet. 217:240-245; 1989), *apetala*-3].

Suitable abiotic stress-inducible promoters include, but not limited to, salt-inducible promoters such as RD29A (Yamaguchi-Shinozalei et al., Mol. Gen. Genet. 236:331-340, 1993); drought-inducible promoters such as maize rab17 gene promoter (Pla et. al., Plant Mol. Biol. 21:259-266, 1993), maize rab28 gene promoter (Busk et. al., Plant J. 11:1285-1295, 1997) and maize Ivr2 gene promoter (Pelleschi et. al., Plant Mol. Biol. 39:373-380, 1999); heat-inducible promoters such as heat tomato hsp80-promoter from tomato (U.S. Pat. No. 5,187,267).

The nucleic acid construct of some embodiments of the invention can further include an appropriate selectable marker and/or an origin of replication. According to some embodiments of the invention, the nucleic acid construct utilized is a shuttle vector, which can propagate both in *E. coli* (wherein the construct comprises an appropriate selectable marker and origin of replication) and be compatible with propagation in cells. The construct according to the present invention can be, for example, a plasmid, a bacmid, a phagemid, a cosmid, a phage, a virus or an artificial chromosome.

The nucleic acid construct of some embodiments of the invention can be utilized to stably or transiently transform plant cells. In stable transformation, the exogenous polynucleotide is integrated into the plant genome and as such it represents a stable and inherited trait. In transient transformation, the exogenous polynucleotide is expressed by the cell transformed but it is not integrated into the genome and as such it represents a transient trait.

There are various methods of introducing foreign genes into both monocotyledonous and dicotyledonous plants (Potrykus, I., Annu. Rev. Plant. Physiol., Plant. Mol. Biol. (1991) 42:205-225; Shimamoto et al., Nature (1989) 338: 274-276).

The principle methods of causing stable integration of exogenous DNA into plant genomic DNA include two main approaches:

(i) *Agrobacterium*-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S. and Arntzen, C. J., Butterworth Publishers, Boston, Mass. (1989) p. 93-112.

(ii) Direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; glass fibers or silicon carbide whisker transformation of cell cultures, embryos or callus tissue, U.S. Pat. No. 5,464,765 or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The *Agrobacterium* system includes the use of plasmid vectors that contain defined DNA segments that integrate into the plant genomic DNA. Methods of inoculation of the plant tissue vary depending upon the plant species and the *Agrobacterium* delivery system. A widely used approach is the leaf disc procedure which can be performed with any tissue explant that provides a good source for initiation of whole plant differentiation. See, e.g., Horsch et al. in Plant Molecular Biology Manual A5, Kluwer Academic Publishers, Dordrecht (1988) p. 1-9. A supplementary approach employs the *Agrobacterium* delivery system in combination with vacuum infiltration. The *Agrobacterium* system is especially viable in the creation of transgenic dicotyledonous plants.

There are various methods of direct DNA transfer into plant cells. In electroporation, the protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals or tungsten particles, and the microprojectiles are physically accelerated into cells or plant tissues.

Following stable transformation plant propagation is exercised. The most common method of plant propagation is by seed. Regeneration by seed propagation, however, has the deficiency that due to heterozygosity there is a lack of uniformity in the crop, since seeds are produced by plants according to the genetic variances governed by Mendelian rules. Basically, each seed is genetically different and each will grow with its own specific traits. Therefore, it is preferred that the transformed plant be produced such that the regenerated plant has the identical traits and characteristics of the parent transgenic plant. For this reason it is preferred that the transformed plant be regenerated by micropropagation which provides a rapid, consistent reproduction of the transformed plants.

Micropropagation is a process of growing new generation plants from a single piece of tissue that has been excised from a selected parent plant or cultivar. This process permits the mass reproduction of plants having the preferred tissue expressing the fusion protein. The new generation plants which are produced are genetically identical to, and have all of the characteristics of, the original plant. Micropropagation allows mass production of quality plant material in a short period of time and offers a rapid multiplication of selected cultivars in the preservation of the characteristics of the original transgenic or transformed plant. The advantages of cloning plants are the speed of plant multiplication and the quality and uniformity of plants produced.

Micropropagation is a multi-stage procedure that requires alteration of culture medium or growth conditions between stages. Thus, the micropropagation process involves four basic stages: Stage one, initial tissue culturing; stage two, tissue culture multiplication; stage three, differentiation and plant formation; and stage four, greenhouse culturing and hardening. During stage one, initial tissue culturing, the tissue culture is established and certified contaminant-free. During stage two, the initial tissue culture is multiplied until a sufficient number of tissue samples are produced to meet production goals. During stage three, the tissue samples grown in stage two are divided and grown into individual plantlets. At stage four, the transformed plantlets are transferred to a greenhouse for hardening where the plants' tolerance to light is gradually increased so that it can be grown in the natural environment.

According to some embodiments of the invention, the transgenic plants are generated by transient transformation of leaf cells, meristematic cells or the whole plant.

Transient transformation can be effected by any of the direct DNA transfer methods described above or by viral infection using modified plant viruses.

Viruses that have been shown to be useful for the transformation of plant hosts include CaMV, Tobacco mosaic virus (TMV), brome mosaic virus (BMV) and Bean Common Mosaic Virus (BV or BCMV). Transformation of plants using plant viruses is described in U.S. Pat. No. 4,855,237 (bean golden mosaic virus; BGV), EP-A 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172-189 (1988). Pseudovirus particles for use in expressing foreign DNA in many hosts, including plants are described in WO 87/06261.

According to some embodiments of the invention, the virus used for transient transformations is avirulent and thus is incapable of causing severe symptoms such as reduced growth rate, mosaic, ring spots, leaf roll, yellowing, streaking, pox formation, tumor formation and pitting. A suitable avirulent virus may be a naturally occurring avirulent virus or an artificially attenuated virus. Virus attenuation may be effected by using methods well known in the art including, but not limited to, sub-lethal heating, chemical treatment or by directed mutagenesis techniques such as described, for example, by Kurihara and Watanabe (Molecular Plant Pathology 4:259-269, 2003), Gal-on et al. (1992), Atreya et al. (1992) and Huet et al. (1994).

Suitable virus strains can be obtained from available sources such as, for example, the American Type culture Collection (ATCC) or by isolation from infected plants. Isolation of viruses from infected plant tissues can be effected by techniques well known in the art such as described, for example by Foster and Tatlor, Eds. "Plant Virology Protocols: From Virus Isolation to Transgenic Resistance (Methods in Molecular Biology (Humana Pr), Vol 81)", Humana Press, 1998. Briefly, tissues of an infected plant believed to contain a high concentration of a suitable virus, preferably young leaves and flower petals, are ground in a buffer solution (e.g., phosphate buffer solution) to produce a virus infected sap which can be used in subsequent inoculations.

Construction of plant RNA viruses for the introduction and expression of non-viral exogenous polynucleotide sequences in plants is demonstrated by the above references as well as by Dawson, W. O. et al., Virology (1989) 172:285-292; Takamatsu et al. EMBO J. (1987) 6:307-311; French et al. Science (1986) 231:1294-1297; Takamatsu et al. FEBS Letters (1990) 269:73-76; and U.S. Pat. No. 5,316,931.

When the virus is a DNA virus, suitable modifications can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

In one embodiment, a plant viral polynucleotide is provided in which the native coat protein coding sequence has been deleted from a viral polynucleotide, a non-native plant viral coat protein coding sequence and a non-native promoter, preferably the subgenomic promoter of the non-native coat protein coding sequence, capable of expression in the plant host, packaging of the recombinant plant viral polynucleotide, and ensuring a systemic infection of the host by the recombinant plant viral polynucleotide, has been inserted. Alternatively, the coat protein gene may be inactivated by insertion of the non-native polynucleotide sequence within it, such that a protein is produced. The recombinant plant viral polynucleotide may contain one or more additional non-native subgenomic promoters. Each non-native subgenomic promoter is capable of transcribing or expressing adjacent genes or polynucleotide sequences in the plant host and incapable of recombination with each other and with native subgenomic promoters. Non-native (foreign) polynucleotide sequences may be inserted adjacent the native plant viral subgenomic promoter or the native and a non-native plant viral subgenomic promoters if more than one polynucleotide sequence is included. The non-native polynucleotide sequences are transcribed or expressed in the host plant under control of the subgenomic promoter to produce the desired products.

In a second embodiment, a recombinant plant viral polynucleotide is provided as in the first embodiment except that the native coat protein coding sequence is placed adjacent one of the non-native coat protein subgenomic promoters instead of a non-native coat protein coding sequence.

In a third embodiment, a recombinant plant viral polynucleotide is provided in which the native coat protein gene is adjacent its subgenomic promoter and one or more non-native subgenomic promoters have been inserted into the viral polynucleotide. The inserted non-native subgenomic promoters are capable of transcribing or expressing adjacent genes in a plant host and are incapable of recombination with each other and with native subgenomic promoters. Non-native polynucleotide sequences may be inserted adjacent the non-native subgenomic plant viral promoters such that the sequences are transcribed or expressed in the host plant under control of the subgenomic promoters to produce the desired product.

In a fourth embodiment, a recombinant plant viral polynucleotide is provided as in the third embodiment except that the native coat protein coding sequence is replaced by a non-native coat protein coding sequence.

The viral vectors are encapsidated by the coat proteins encoded by the recombinant plant viral polynucleotide to produce a recombinant plant virus. The recombinant plant viral polynucleotide or recombinant plant virus is used to infect appropriate host plants. The recombinant plant viral polynucleotide is capable of replication in the host, systemic spread in the host, and transcription or expression of foreign gene(s) (exogenous polynucleotide) in the host to produce the desired protein.

Techniques for inoculation of viruses to plants may be found in Foster and Taylor, eds. "Plant Virology Protocols: From Virus Isolation to Transgenic Resistance (Methods in Molecular Biology (Humana Pr), Vol 81)", Humana Press, 1998; Maramorsh and Koprowski, eds. "Methods in Virology" 7 vols, Academic Press, New York 1967-1984; Hill, S. A. "Methods in Plant Virology", Blackwell, Oxford, 1984; Walkey, D. G. A. "Applied Plant Virology", Wiley, New York, 1985; and Kado and Agrawa, eds. "Principles and Techniques in Plant Virology", Van Nostrand-Reinhold, New York.

In addition to the above, the polynucleotide of the present invention can also be introduced into a chloroplast genome thereby enabling chloroplast expression.

A technique for introducing exogenous polynucleotide sequences to the genome of the chloroplasts is known. This technique involves the following procedures. First, plant cells are chemically treated so as to reduce the number of chloroplasts per cell to about one. Then, the exogenous polynucleotide is introduced via particle bombardment into the cells with the aim of introducing at least one exogenous polynucleotide molecule into the chloroplasts. The exogenous polynucleotide is selected such that it is integratable into the chloroplast's genome via homologous recombination which is readily effected by enzymes inherent to the chloroplast. To this end, the exogenous polynucleotide includes, in addition to a gene of interest, at least one polynucleotide stretch which is derived from the chloroplast's genome. In addition, the exogenous polynucleotide includes a selectable marker, which serves by sequential selection procedures to ascertain that all or substantially all of the copies of the chloroplast genomes following such selection will include the exogenous polynucleotide. Further details relating to this technique are found in U.S. Pat. Nos. 4,945,050; and 5,693,507 which are incorporated herein by reference. A polypeptide can thus be produced by the protein expression system of the chloroplast and become integrated into the chloroplast's inner membrane.

Since abiotic stress tolerance, growth, biomass, yield and/or vigor in plants can involve multiple genes acting additively or in synergy (see, for example, in Quesda et al., Plant Physiol. 130:951-063, 2002), the present invention also envisages expressing a plurality of exogenous polynucleotides in a single host plant to thereby achieve superior effect on abiotic stress tolerance, growth, biomass, yield and/or vigor.

Expressing a plurality of exogenous polynucleotides in a single host plant can be effected by co-introducing multiple nucleic acid constructs, each including a different exogenous polynucleotide, into a single plant cell. The transformed cell can then be regenerated into a mature plant using the methods described hereinabove.

Alternatively, expressing a plurality of exogenous polynucleotides in a single host plant can be effected by co-introducing into a single plant-cell a single nucleic-acid construct including a plurality of different exogenous polynucleotides. Such a construct can be designed with a single promoter sequence which can transcribe a polycistronic messenger RNA including all the different exogenous polynucleotide sequences. To enable co-translation of the different polypeptides encoded by the polycistronic mes sager RNA, the polynucleotide sequences can be inter-linked via an internal ribosome entry site (IRES) sequence which facilitates translation of polynucleotide sequences positioned downstream of the IRES sequence. In this case, a transcribed polycistronic RNA molecule encoding the different polypeptides described above will be translated from both the capped 5' end and the two internal IRES sequences of the polycistronic RNA molecule to thereby produce in the cell all different polypeptides. Alternatively, the construct can include several promoter sequences each linked to a different exogenous polynucleotide sequence.

The plant cell transformed with the construct including a plurality of different exogenous polynucleotides can be regenerated into a mature plant, using the methods described hereinabove.

Alternatively, expressing a plurality of exogenous polynucleotides can be effected by introducing different nucleic acid constructs, including different exogenous polynucleotides, into a plurality of plants. The regenerated transformed plants can then be cross-bred and resultant progeny selected for superior abiotic stress tolerance, growth, biomass, yield and/or vigor traits, using conventional plant breeding techniques.

According to some embodiments of the invention, the plant expressing the exogenous polynucleotide(s) is grown under normal conditions.

According to some embodiments of the invention, the method further comprising growing the plant expressing the exogenous polynucleotide(s) under the abiotic stress.

Thus, the invention encompasses plants exogenously expressing (as described above) the polynucleotide(s) and/or polypeptide(s) of the invention. Once expressed within the plant cell or the entire plant, the level of the polypeptide encoded by the exogenous polynucleotide can be determined by methods well known in the art such as, activity assays, Western blots using antibodies capable of specifically binding the polypeptide, Enzyme-Linked ImmunoSorbent Assay (ELISA), radio-immuno-assays (RIA), immunohistochemistry, immunocytochemistry, immunofluorescence and the like.

Methods of determining the level in the plant of the RNA transcribed from the exogenous polynucleotide are well known in the art and include, for example, Northern blot analysis, reverse transcription polymerase chain reaction (RT-PCR) analysis (including quantitative, semi-quantitative or real-time RT-PCR) and RNA—in situ hybridization.

The polynucleotides and polypeptides described hereinabove can be used in a wide range of economical plants, in a safe and cost effective manner.

The effect of the transgene (the exogenous polynucleotide encoding the polypeptide) on abiotic stress tolerance, growth, biomass, yield and/or vigor can be determined using known methods.

Abiotic Stress Tolerance

Transformed (i.e., expressing the transgene) and non-transformed (wild type) plants are exposed to an abiotic stress condition, such as water deprivation, suboptimal temperature (low temperature, high temperature), nutrient deficiency, nutrient excess, a salt stress condition, osmotic stress, heavy metal toxicity, anaerobiosis, atmospheric pollution and UV irradiation.

Salinity Tolerance Assay

Transgenic plants with tolerance to high salt concentrations are expected to exhibit better germination, seedling vigor or growth in high salt. Salt stress can be effected in many ways such as, for example, by irrigating the plants with a hyperosmotic solution, by cultivating the plants hydroponically in a hyperosmotic growth solution (e.g., Hoagland solution with added salt), or by culturing the plants in a hyperosmotic growth medium [e.g., 50% Murashige-Skoog medium (MS medium) with added salt]. Since different plants vary considerably in their tolerance to salinity, the salt concentration in the irrigation water, growth solution, or growth medium can be adjusted according to the specific characteristics of the specific plant cultivar or variety, so as to inflict a mild or moderate effect on the physiology and/or morphology of the plants (for guidelines as to appropriate concentration see, Bernstein and Kafkafi, Root Growth Under Salinity Stress In: Plant Roots, The Hidden Half 3rd ed. Waisel Y, Eshel A and Kafkafi U. (editors) Marcel Dekker Inc., New York, 2002, and reference therein).

For example, a salinity tolerance test can be performed by irrigating plants at different developmental stages with increasing concentrations of sodium chloride (for example 50 mM, 100 mM, 200 mM, 400 mM NaCl) applied from the bottom and from above to ensure even dispersal of salt. Following exposure to the stress condition the plants are frequently monitored until substantial physiological and/or morphological effects appear in wild type plants. Thus, the external phenotypic appearance, degree of wilting and overall success to reach maturity and yield progeny are compared between control and transgenic plants. Quantitative parameters of tolerance measured include, but are not limited to, the average wet and dry weight, growth rate, leaf size, leaf coverage (overall leaf area), the weight of the seeds yielded, the average seed size and the number of seeds produced per plant. Transformed plants not exhibiting substantial physiological and/or morphological effects, or exhibiting higher biomass than wild-type plants, are identified as abiotic stress tolerant plants.

Osmotic Tolerance Test

Osmotic stress assays (including sodium chloride and PEG assays) are conducted to determine if an osmotic stress phenotype was sodium chloride-specific or if it was a general osmotic stress related phenotype. Plants which are tolerant to osmotic stress may have more tolerance to drought and/or freezing. For salt and osmotic stress experiments, the medium is supplemented for example with 50 mM, 100 mM, 200 mM NaCl or 15%, 20% or 25% PEG. See also Examples 6 and 7 of the Examples section which follows.

Drought Tolerance Assay/Osmoticum Assay

Tolerance to drought is performed to identify the genes conferring better plant survival after acute water deprivation. To analyze whether the transgenic plants are more tolerant to drought, an osmotic stress produced by the non-ionic osmolyte sorbitol in the medium can be performed. Control and transgenic plants are germinated and grown in plant-agar plates for 4 days, after which they are transferred to plates containing 500 mM sorbitol. The treatment causes growth retardation, then both control and transgenic plants are compared, by measuring plant weight (wet and dry), yield, and by growth rates measured as time to flowering.

Conversely, soil-based drought screens are performed with plants overexpressing the polynucleotides detailed above. Seeds from control *Arabidopsis* plants, or other transgenic plants overexpressing the polypeptide of the invention are germinated and transferred to pots. Drought stress is obtained after irrigation is ceased accompanied by placing the pots on absorbent paper to enhance the soil-drying rate. Transgenic and control plants are compared to each other when the majority of the control plants develop severe wilting. Plants are re-watered after obtaining a significant fraction of the control plants displaying a severe wilting. Plants are ranked comparing to controls for each of two criteria: tolerance to the drought conditions and recovery (survival) following re-watering.

Cold Stress Tolerance

One way to analyze cold stress is as follows. Mature (25 day old) plants are transferred to 4° C. chambers for 1 or 2 weeks, with constitutive light. Later on plants are moved back to greenhouse. Two weeks later damages from chilling period, resulting in growth retardation and other phenotypes, are compared between control and transgenic plants, by measuring plant weight (wet and dry), and by comparing growth rates measured as time to flowering, plant size, yield, and the like.

Heat Stress Tolerance

One way to measure heat stress tolerance is by exposing the plants to temperatures above 34° C. for a certain period. Plant tolerance is examined after transferring the plants back to 22° C. for recovery and evaluation after 5 days relative to internal controls (non-transgenic plants) or plants not exposed to neither cold or heat stress.

Germination Tests

Germination tests compare the percentage of seeds from transgenic plants that could complete the germination process to the percentage of seeds from control plants that are treated in the same manner. Normal conditions are considered for example, incubations at 22° C. under 22-hour light 2-hour dark daily cycles. Evaluation of germination and seedling vigor is conducted between 4 and 14 days after planting. The basal media is 50% MS medium (Murashige and Skoog, 1962 Plant Physiology 15, 473-497).

Germination is checked also at unfavorable conditions such as cold (incubating at temperatures lower than 10° C. instead of 22° C.) or using seed inhibition solutions that contain high concentrations of an osmolyte such as sorbitol (at concentrations of 50 mM, 100 mM, 200 mM, 300 mM, 500 mM, and up to 1000 mM) or applying increasing concentrations of salt (of 50 mM, 100 mM, 200 mM, 300 mM, 500 mM NaCl).

Effect of the Transgene on Plant's Growth, Biomass, Yield and/or Vigor

Plant vigor can be calculated by the increase in growth parameters such as leaf area, fiber length, rosette diameter, plant fresh weight and the like per time.

The growth rate can be measured using digital analysis of growing plants. For example, images of plants growing in greenhouse on plot basis can be captured every 3 days and the rosette area can be calculated by digital analysis. Rosette area growth is calculated using the difference of rosette area between days of sampling divided by the difference in days between samples.

Measurements of seed yield can be done by collecting the total seeds from 8-16 plants together, weighting them using analytical balance and dividing the total weight by the number of plants. Seed per growing area can be calculated in the same manner while taking into account the growing area given to a single plant. Increase seed yield per growing area could be achieved by increasing seed yield per plant, and/or by increasing number of plants capable of growing in a given area.

Evaluation of the seed yield per plant can be done by measuring the amount (weight or size) or quantity (i.e., number) of dry seeds produced and harvested from 8-16 plants and divided by the number of plants.

Evaluation of growth rate can be done by measuring plant biomass produced, rosette area, leaf size or root length per time (can be measured in $cm^2$ per day of leaf area).

Fiber length can be measured using fibrograph. The fibrograph system was used to compute length in terms of "Upper Half Mean" length. The upper half mean (UHM) is the average length of longer half of the fiber distribution. The fibrograph measures length in span lengths at a given percentage point (Hypertext Transfer Protocol://World Wide Web (dot) cottoninc (dot) com/ClassificationofCotton/?Pg=4#Length).

Thus, the present invention is of high agricultural value for promoting the yield of commercially desired crops (e.g., biomass of vegetative organ such as poplar wood, or reproductive organ such as number of seeds or seed biomass).

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Identifying Putative Abiotic Stress—Tolerance and or Yield/Biomass Increase Genes The present inventors have identified genes which increase abiotic stress-tolerance (ABST) and/or growth rate/yield/biomass/vigor, as follows. The genes were validated in vivo as previously described in WO2004/104162 to the present assignee. All nucleotide sequence datasets used here were originated from publicly available databases. Sequence data from 50 different species (mainly plant species) was introduced into a single, comprehensive database. Other information on gene expression, protein annotation, enzymes and pathways were also incorporated. Major databases used include:

Genomes
- Arabidopsis genome [TAR genome version 6 (Hypertext Transfer Protocol://World Wide Web (dot) arabidopsis (dot) org/)]
- Rice genome [IRGSP build 4.0 (Hypertext Transfer Protocol://rgp (dot) dna (dot) affrc (dot) go (dot) jp/IRGSP/)].
- Poplar [Populus trichocarpa release 1.1 from JGI (assembly release v1.0) (Hypertext Transfer Protocol://World Wide Web (dot) genome (dot) jgi-psf (dot) org/)]
- Brachypodium [JGI 4× assembly Hypertext Transfer Protocol://World Wide Web (dot) brachpodium (dot) org)]
- Soybean [DOE-JGI SCP, version Glyma0 (Hypertext Transfer Protocol://World Wide Web (dot) phytozome (dot) net/)]
- Grape [NCBI WGS assembly ftp://ftp (dot) ncbi (dot) nih (dot) gov/genbank/wgs/)]
- Castobean [TIGR/J Craig Venter Institute 4× assemby Hypertext Transfer Protocol://msc (dot) jcvi (dot) org/r_communis
- Sorghum [DOE-JGI SCP, version Sbi1 Hypertext Transfer Protocol://World Wide Web (dot) phytozome (dot) net/)].

Expressed EST and mRNA sequences were extracted from
- GeneBank versions 154, 157, 160, 161, 164, and 165 (Hypertext Transfer Protocol://World Wide Web (dot) ncbi (dot) nlm (dot) nih (dot) gov/dbEST/)
- RefSeq (Hypertext Transfer Protocol://World Wide Web (dot) ncbi (dot) nlm (dot) nih (dot) gov/RefSeq/).
- TAR (Hypertext Transfer Protocol://World Wide Web (dot) arabidopsis (dot) org/).

Protein and pathway databases
- Uniprot (Hypertext Transfer Protocol://World Wide Web.expasy.uniprot.org/).
- AraCyc (Hypertext Transfer Protocol://World Wide Web (dot) arabidopsis (dot) org/biocyc/index (dot) jsp).
- ENZYME (Hypertext Transfer Protocol://expasy.org/enzyme/).

Microarray datasets were downloaded from
- GEO (Hypertext Transfer Protocol://World Wide Web.ncbi.nlm.nih.gov/geo/)
- TAIR (Hypertext Transfer Protocol://World Wide Web.arabidopsis.org/).
- Proprietary Evogene's cotton fiber microarray data QTL information
- Gramene (Hypertext Transfer Protocol://World Wide Web (dot) gramene (dot) org/qtl/).

Database Assembly was performed to build a wide, rich, reliable annotated and easy to analyze database comprised of publicly available genomic mRNA, ESTs DNA sequences, data from various crops as well as gene expression, protein annotation and pathway data QTLs, and other relevant information.

Database assembly is comprised of a toolbox of gene refining, structuring, annotation and analysis tools enabling to construct a tailored database for each gene discovery project. Gene refining and structuring tools enable to reliably detect splice variants and antisense transcripts, generating understanding of various potential phenotypic outcomes of a single gene. The capabilities of the "LEADS" platform of Compugen LTD for analyzing human genome have been confirmed and accepted by the scientific committee ("Widespread Antisense Transcription", Yelin, et al. (2003) Nature Biotechnology 21, 379-85; "Splicing of Alu Sequences", Lev-Maor, et al. (2003) Science 300 (5623), 1288-91), and have proven most efficient in plant genomics as well.

EST Clustering and Gene Assembly

For clustering and assembly of arabidopsis and rice genes the "genomic LEADS" version was employed. This tool allows most accurate clustering of ESTs and mRNA sequences on genome, and predicts gene structure as well as alternative splicing events and anti-sense transcription.

For organisms with no available full genome sequence data, "expressed LEADS" as well as TIGR (Hypertext Transfer Protocol://World Wide Web (dot) tigr (dot) org/) clustering software were applied. The results of the two clustering tools were compared and in cases where clusters predicted by the two tools were significantly different, both versions were presented and considered.

Gene annotation-Predicted genes and proteins were annotated as follows:
- Blast search (Hypertext Transfer Protocol://World Wide Web (dot) ncbi (dot) nlm (dot) nih (dot) gov (dot) library (dot) vu (dot) edu (dot) au/BLAST/) against all plant UniProt (Hypertext Transfer Protocol://World Wide Web (dot) expasy (dot) uniprot (dot) org/) sequences was performed.
- Frame-Finder (Hypertext Transfer Protocol://World Wide Web (dot) ebi (dot) ac (dot) uk/~guy/estate/) calculations with default statistics was used to predict protein sequences for each transcript.
- The predicted proteins were analyzed by InterPro (Hypertext Transfer Protocol://World Wide Web (dot) ebi (dot) ac (dot) uk/interpro/).
- Blast against proteins from AraCyc and ENZYME databases was used to map the predicted transcripts to AraCyc pathways.
- Each transcript was compared using tblastx algorithm (Hypertext Transfer Protocol://World Wide Web (dot)

ncbi (dot) nlm (dot) nih (dot) gov (dot) library (dot) vu (dot) edu (dot) au/BLAST/) against all other organism databases to validate the accuracy of the predicted protein sequence, and for efficient detection of orthologs.

Gene Expression Profiling

Few data sources were exploited for gene expression profiling, namely microarray data and digital expression profile (see below). According to gene expression profile, a correlation analysis was performed to identify genes which are co-regulated under different development stages and environmental conditions.

Publicly available microarray datasets were downloaded from TAIR and NCBI GEO sites, renormalized, and integrated into the database. Expression profiling was one of the most important resource data for identifying genes important for ABST. Moreover, when homolog genes from different crops were responsive to ABST, the genes were marked as "highly predictive to improve ABST".

A digital expression profile summary was compiled for each cluster according to all keywords included in the sequence records comprising the cluster. Digital expression, also known as electronic Northern Blot, is a tool that displays virtual expression profile based on the EST sequences forming the gene cluster. The tool can provide the expression profile of a cluster in terms of plant anatomy (in what tissues/organs is the gene expressed), developmental stage (the developmental stages at which a gene can be found) and profile of treatment (provides the physiological conditions under which a gene is expressed such as drought, cold, pathogen infection, etc). Given a random distribution of ESTs in the different clusters, the digital expression provides a probability value that describes the probability of a cluster having a total of N ESTs to contain X ESTs from a certain collection of libraries. For the probability calculations are taken into consideration: a) the number of ESTs in the cluster, b) the number of ESTs of the implicated and related libraries, c) the overall number of ESTs available representing the species. Thereby clusters with low probability values are highly enriched with ESTs from the group of libraries of interest indicating a specialized expression.

The concepts of orthology and paralogy have recently been applied to functional characterizations and classifications on the scale of whole-genome comparisons. Orthologs and paralogs constitute two major types of homologs: The first evolved from a common ancestor by specialization, and the latter are related by duplication events. It is assumed that paralogs arising from ancient duplication events are likely to have diverged in function while true orthologs are more likely to retain identical function over evolutionary time.

To further investigate and identify the ABST putative ortholog genes from monocot species, two computational methods were integrated:

(i) Method for Alignments of Ortholog Sequences based on construction ortholog groups across multiple eukaryotic taxa, using modifications on the Markov cluster algorithm to group putative orthologs and paralogs. These putative orthologs were further organized under Phylogram—a branching diagram (tree) assumed to be an estimate of a phylogeny of the genes.

(ii) Method for Generating Genes Expression Profile "Digital Expression"

The present inventors have performed considerable work aimed at annotating sequences. Expression data was analyzed and the EST libraries were classified using a fixed vocabulary of custom terms such as experimental treatments. The annotations from all the ESTs clustered to a gene were analyzed statistically by comparing their frequency in the cluster versus their abundance in the database, allowing to construct a numeric and graphic expression profile of that gene, which is termed "digital expression".

The rationale of using these two complementary methods is based on the assumption that true orthologs are likely to retain identical function over evolutionary time. These two methods (sequence and expression pattern) provide two different sets of indications on function similarities between two homologous genes, similarities in the sequence level—identical amino acids in the protein domains and similarity in expression profiles.

Overall, 110 genes were identified to have a major impact on ABST when overexpressed in plants. The identified ABST genes, their curated polynucleotide and polypeptide sequences, as well as their updated sequences according to Genebank database are summarized in Table 1, hereinbelow.

TABLE 1

Identified ABST Genes

| SEQ ID NO: Polynucleotide | Gene Name | Cluster Name | Organism | SEQ ID NO: Polypeptide | Polynucleotide Description | Polypeptide Description |
|---|---|---|---|---|---|---|
| 1 | MAB1 | MAB1.0.rice\|gb154\|BM421111_T1 | rice | 201 | | |
| 2 | | MAB1.1.rice\|gb157.2\|BM421111_T1 | rice | 202 | updated to production gb157.2 | updated to production gb157.2 |
| 3 | MAB2 | MAB2.0.rice\|gb154\|AU225547_T1 | rice | | | No predicted protein |
| 4 | | MAB2.1.rice\|gb157.2\|AU225547_T1 | rice | | updated to production gb157.2 | |
| 5 | MAB3 | MAB3.0.rice\|gb154\|BE039995_T1 | rice | 203 | | |
| 6 | | MAB3.1.rice\|gb157.2\|BE039995_T1 | rice | 204 | updated to production gb157.2 | updated to production gb157.2 |
| 7 | MAB4 | MAB4.0.rice\|gb154\|BI812277_T1 | rice | 205 | | |
| 8 | | MAB4.7.rice\|gb157.2\|BI812277_CT1 | rice | | curated | |
| 9 | MAB5 | MAB5.0.rice\|gb154\|CB624106_T1 | rice | 206 | | |
| 10 | MAB6 | MAB6.0.arabidopsis\|gb154\|Z47404_T1 | arabidopsis | 207 | | |
| 11 | MAB7 | MAB7.0.arabidopsis\|6\|AT5G47560.1 | arabidopsis | 208 | | |
| 12 | | MAB7.1.arabidopsis\|gb165\|AT5G47560_T1 | arabidopsis | 209 | updated to production gb165 | updated to production gb165 |

TABLE 1-continued

Identified ABST Genes

| SEQ ID NO: Polynucleotide | Gene Name | Cluster Name | Organism | SEQ ID NO: Polypeptide | Polynucleotide Description | Polypeptide Description |
|---|---|---|---|---|---|---|
| 13 | MAB8 | MAB8.0.rice\|gb154\|BU672931_T1 | rice | 210 | | |
| 14 | | MAB8.7.rice\|gb154\|BU672931_T1 | rice | | Bioinformatics & DNA Curated | |
| 15 | MAB9 | MAB9.0.arabidopsis\|gb154\|BE844934_T1 | arabidopsis | 211 | | |
| 16 | MAB10 | MAB10.0.arabidopsis\|gb154\|Z27056_T1 | arabidopsis | 212 | | |
| 17 | MAB11 | MAB11.0.arabidopsis\|gb154\|Z34014_T1 | arabidopsis | 213 | | |
| 18 | | MAB11.1.arabidopsis\|gb165\|AT5G52300_T1 | arabidopsis | 214 | updated to production gb165 | updated to production gb165 |
| 19 | MAB12 | MAB12.0.arabidopsis\|gb154\|ATLTIL40_T1 | arabidopsis | 215 | | |
| 20 | | MAB12.1.arabidopsis\|gb165\|AT5G52310_T1 | arabidopsis | 216 | updated to production gb165 | updated to production gb165 |
| 21 | MAB13 | MAB13.0.arabidopsis\|6\|AT2G38760.1 | arabidopsis | 217 | | |
| 22 | | MAB13.1.arabidopsis\|gb165\|AT2G38760_T1 | arabidopsis | 218 | updated to production gb165 | updated to production gb165 |
| 23 | MAB14 | MAB14.0.rice\|gb154\|AB042259_T1 | rice | 219 | | |
| 24 | | MAB14.1.rice\|gb157.2\|AB042259_T1 | rice | 220 | updated to production gb157.2 | updated to production gb157.2 |
| 25 | MAB15 | MAB15.0.sorghum\|gb154\|AI724695_T1 | sorghum | 221 | | |
| 26 | MAB16 | MAB16.0.rice\|gb154\|BI795172_T1 | rice | 222 | | |
| 27 | | MAB16.1.rice\|gb157.2\|BI795172_T1 | rice | 223 | updated to production gb157.2 | updated to production gb157.2 |
| 28 | MAB17 | MAB17.0.soybean\|gb154\|BE821839_T1 | soybean | 224 | | |
| 29 | MAB18 | MAB18.0.barley\|gb154\|BF625971_T1 | barley | 225 | | |
| | | | | 226 | | protein Bioinformatics & Protein Curated |
| 30 | MAB19 | MAB19.0.sorghum\|gb154\|AW563861_T1 | sorghum | 227 | | |
| 31 | | MAB19.1.sorghum\|gb161.xeno\|AW563861_T1 | sorghum | 228 | updated to production gb161.xeno | updated to production gb161.xeno |
| 32 | MAB20 | MAB20.0.arabidopsis\|gb154\|T04691_T1 | arabidopsis | 229 | | |
| 33 | | MAB20.1.arabidopsis\|gb165\|AT1G61890_T1 | arabidopsis | 230 | updated to production gb165 | updated to production gb165 |
| 34 | MAB21 | MAB21.0.rice\|gb154\|BE230053_T1 | rice | 231 | | |
| 35 | | MAB21.1.rice\|gb157.2\|BE230053_T1 | rice | 232 | updated to production gb157.2 | updated to production gb157.2 |
| 36 | MAB22 | MAB22.0.tomato\|gb154\|BG791299_T1 | tomato | 233 | | |
| | | | | 234 | | Curated |
| 37 | MAB23 | MAB23.0.rice\|gb154\|BI305810_T1 | rice | 235 | | |
| 38 | MAB24 | MAB24.0.rice\|gb154\|BI808273_T1 | rice | 236 | | |
| 39 | | MAB24.7.rice\|gb157.2\|BI808273_CT1 | rice | | curated | |
| 40 | MAB25 | MAB25.0.arabidopsis\|6\|AT1G27760.1 | arabidopsis | 237 | | |
| 41 | | MAB25.1.arabidopsis\|gb165\|AT1G27760_T1 | arabidopsis | 238 | updated to production gb165 | updated to production gb165 |
| 42 | MAB26 | MAB26.0.rice\|gb154\|AW155625_T1 | rice | 239 | | |
| 43 | | MAB26.7.rice\|gb157.2\|BI305400_CT1 | rice | | curated | |
| 44 | MAB27 | MAB27.0.arabidopsis\|gb154\|AY045660_T1 | arabidopsis | 240 | | |
| 45 | | MAB27.7.arabidopsis\|gb165\|AT5G24120_CT1 | arabidopsis | | curated | |
| 46 | MAB28 | MAB28.0.rice\|gb154\|BI795108_T1 | rice | 241 | | |
| 47 | | MAB28.7.rice\|gb157.2\|BI795108_CT1 | rice | | curated | |
| 48 | MAB29 | MAB29.0.arabidopsis\|gb154\|AU239137_T2 | arabidopsis | 242 | | |
| 49 | | MAB29.1.arabidopsis\|gb165\|AT2G25600_T1 | arabidopsis | 243 | updated to production gb165 | updated to production gb165 |
| 50 | MAB30 | MAB30.0.arabidopsis\|gb154\|AY062542_T1 | arabidopsis | 244 | | |
| 51 | | MAB30.7.arabidopsis\|gb165\|AT1G70300_CT1 | arabidopsis | | Curated | |
| 52 | MAB31 | MAB31.0.soybean\|gb154\|BI968709_T1 | soybean | 245 | | |
| 53 | | MAB31.7.soybean\|gb162\|BI968709_CT1 | soybean | 246 | Curated | curated |
| 54 | MAB32 | MAB32.0.rice\|gb154\|AF039532_T1 | rice | 247 | | |
| 55 | MAB33 | MAB33.0.maize\|gb154\|AI615215_T1 | maize | 248 | | |
| 56 | | MAB33.1.maize\|gb164\|AI615215_T1 | maize | 249 | | updated to production gb164 |
| 57 | MAB34 | MAB34.0.barley\|gb154\|TG_BF625450_T1 | barley | 250 | | |

TABLE 1-continued

Identified ABST Genes

| SEQ ID NO: Polynucleotide | Gene Name | Cluster Name | Organism | SEQ ID NO: Polypeptide | Polynucleotide Description | Polypeptide Description |
|---|---|---|---|---|---|---|
| 58 | | MAB34.1.barley\|gb157.2\|BF625450_T1 | barley | 251 | updated to production gb157.2 | updated to production gb157.2 |
| 59 | MAB35 | MAB35.0.*arabidopsis*\|gb154\|AA651513_T1 | *arabidopsis* | 252 | | |
| 60 | | MAB35.1.*arabidopsis*\|gb165\|AT2G16890_T1 | *arabidopsis* | 253 | updated to production gb165 | updated to production gb165 |
| 61 | MAB36 | MAB36.0.*arabidopsis*\|gb154\|AU239340_T1 | *arabidopsis* | 254 | | |
| 62 | | MAB36.1.*arabidopsis*\|gb165\|AT4G27570_T1 | *arabidopsis* | 255 | updated to production gb165 | updated to production gb165 |
| 63 | MAB37 | MAB37.0.tomato\|gb154\|BG125939_T1 | tomato | 256 | | |
| 64 | | MAB37.7.tomato\|gb164\|BG125939_CT1 | tomato | | curated | |
| 65 | MAB38 | MAB38.0.wheat\|gb154\|BE492836_T1 | wheat | 257 | | |
| 66 | | MAB38.7.wheat\|gb164\|BE492836_CT1 | wheat | 258 | curated | curated |
| 67 | MAB39 | MAB39.0.barley\|gb154\|AL500200_T1 | barley | 259 | | |
| 68 | | MAB39.1.barley\|gb157.2\|AL500200_T1 | barley | 260 | updated to production gb157.2 | updated to production gb157.2 |
| 69 | MAB40 | MAB40.0.rice\|gb154\|AA754628_T1 | rice | 261 | | |
| 70 | | MAB40.7.rice\|gb157.2\|AA754628_CT1 | rice | | curated | |
| 71 | MAB41 | MAB41.0.tomato\|gb154\|AI489494_T1 | tomato | 262 | | |
| 72 | | MAB41.7.tomato\|gb164\|AI489494_CT1 | tomato | | curated | |
| 73 | MAB42 | MAB42.0.*sorghum*\|gb154\|BE595950_T1 | *sorghum* | 263 | | |
| 74 | | MAB42.7.*sorghum*\|gb161.xeno\|AI881418_CT1 | *sorghum* | 264 | curated | curated |
| 75 | MAB43 | MAB43.0.*arabidopsis*\|gb154\|BE662945_T1 | *arabidopsis* | 265 | | |
| 76 | | MAB43.1.*arabidopsis*\|gb165\|AT5G26920_T1 | *arabidopsis* | 266 | updated to production gb165 | updated to production gb165 |
| 77 | MAB44 | MAB44.0.*arabidopsis*\|gb154\|H36025_T1 | *arabidopsis* | 267 | | |
| 78 | | MAB44.1.*arabidopsis*\|gb165\|AT1G67360_T1 | *arabidopsis* | 268 | updated to production gb165 | updated to production gb165 |
| 79 | MAB45 | MAB45.0.wheat\|gb154\|TG_BQ172359_T1 | wheat | 269 | | |
| 80 | | MAB45.1.wheat\|gb164\|BQ172359_T1 | wheat | 270 | updated to production gb164 | updated to production gb164 |
| 81 | MAB46 | MAB46.0.*arabidopsis*\|gb154\|AA389812_T1 | *arabidopsis* | 271 | | |
| 82 | MAB47 | MAB47.0.*sorghum*\|gb154\|AW672286_T1 | *sorghum* | 272 | | |
| 83 | | MAB47.7.*sorghum*\|gb161.xeno\|AI948276_CT1 | *sorghum* | 273 | Curated | Curated |
| 84 | MAB48 | MAB48.0.rice\|gb154\|BI802161_T1 | rice | 274 | | |
| 85 | | MAB48.7.rice\|gb157.2\|AU092454_CT1 | rice | 275 | curated | curated |
| 86 | MAB49 | MAB49.0.maize\|gb154\|TG_AI621810_T1 | maize | 276 | | |
| 87 | | MAB49.7.maize\|gb164\|AI621810_CT1 | maize | | Curated | |
| 88 | MAB50 | MAB50.0.*arabidopsis*\|gb154\|W43146_T1 | *arabidopsis* | 277 | | |
| 89 | | MAB50.1.*arabidopsis*\|gb165\|AT5G48570_T1 | *arabidopsis* | 278 | updated to production gb165 | updated to production gb165 |
| 90 | MAB91 | MAB91.0.*arabidopsis*\|gb154\|AU236480_T1 | *arabidopsis* | 279 | | |
| | | | | 280 | | curated |
| 91 | MAB96 | MAB96.0.*arabidopsis*\|gb154\|Z27256_T1 | *arabidopsis* | 281 | | |
| 92 | | MAB96.7.*arabidopsis*\|gb165\|AT5G03800_CT1 | *arabidopsis* | 282 | curated | curated |
| 93 | MAB99 | MAB99.0.tomato\|gb154\|BG735056_T1 | tomato | 283 | | |
| 94 | MAB100 | MAB100.0.*arabidopsis*\|gb154\|Z37259_T1 | *arabidopsis* | 284 | | |
| 95 | | MAB100.1.*arabidopsis*\|gb165\|AT1G01470_T1 | *arabidopsis* | 285 | updated to production gb165 | updated to production gb165 |
| 96 | MAB104 | MAB104.0.rice\|gb154\|BE039215_T1 | rice | 286 | | |
| 97 | | MAB104.1.rice\|gb157.2\|BE039215_T1 | rice | 287 | updated to production gb157.2 | updated to production gb157.2 |
| 98 | MAB121 | MAB121.0.sugarcane\|gb157\|CA079500_T1 | sugarcane | 288 | | |
| 99 | | MAB121.1.sugarcane\|gb157.2\|CA079500_T1 | sugarcane | 289 | updated to production gb157.2 | updated to production gb157.2 |
| 100 | MAB122 | MAB122.0.maize\|gb154\|AI901344_T9 | maize | 290 | | |
| 101 | MAB123 | MAB123.0.barley\|gb157\|BF626638_T1 | barley | 291 | | |
| 102 | | MAB123.1.barley\|gb157.2\|BF626638_T1 | barley | 292 | updated to production gb157.2 | updated to production gb157.2 |
| 103 | MAB124 | MAB124.0.sugarcane\|gb157\|CA284042_T1 | sugarcane | 293 | | |
| 104 | | MAB124.1.sugarcane\|gb157.2\|CA284042_T1 | sugarcane | 294 | updated to production gb157.2 | updated to production gb157.2 |
| 105 | MAB125 | MAB125.0.rice\|gb157\|CF957213_T1 | rice | 295 | | |

TABLE 1-continued

Identified ABST Genes

| SEQ ID NO: Polynucleotide | Gene Name | Cluster Name | Organism | SEQ ID NO: Polypeptide | Polynucleotide Description | Polypeptide Description |
|---|---|---|---|---|---|---|
| 106 | | MAB125.1.rice\|gb157.2\|CF957213_T1 | rice | 296 | updated to production gb157.2 | updated to production gb157.2 |
| 107 | MAB126 | MAB126.0.grape\|gb157\|BQ797309_T1 | grape | 297 | | |
| 108 | | MAB126.1.grape\|gb160\|BQ797309_T1 | grape | 298 | updated to production gb160 | updated to production gb160 |
| 109 | MAB127 | MAB127.0.grape\|gb157\|CB971532_T1 | grape | 299 | | |
| 110 | | MAB127.1.grape\|gb160\|CB971532_T1 | grape | 300 | updated to production gb160 | updated to production gb160 |
| 111 | MAB128 | MAB128.0.sugarcane\|gb157\|CA142162_T1 | sugarcane | 301 | | |
| 112 | | MAB128.1.sugarcane\|gb157.2\|CA142162_T1 | sugarcane | 302 | updated to production gb157.2 | updated to production gb157.2 |
| 113 | MAB129 | MAB129.0.tomato\|gb157\|AI486106_T1 | tomato | 303 | | |
| 114 | | MAB129.1.tomato\|gb164\|AI486106_T1 | tomato | 304 | updated to production gb164 | updated to production gb164 |
| 115 | MAB130 | MAB130.0.canola\|gb157\|CD829694_T1 | canola | 305 | | |
| 116 | MAB131 | MAB131.0.tomato\|gb157\|AW928843_T1 | tomato | 306 | | |
| 117 | | MAB131.1.tomato\|gb164\|AW928843_T1 | tomato | 307 | updated to production gb164 | updated to production gb164 |
| 118 | MAB132 | MAB132.0.barley\|gb157\|BF621624_T1 | barley | 308 | | |
| 119 | MAB133 | MAB133.0.barley\|gb157\|BE411546_T1 | barley | 309 | | |
| 120 | | MAB133.1.barley\|gb157.2\|BE411546_T1 | barley | 310 | updated to production gb157.2 | updated to production gb157.2 |
| 121 | MAB134 | MAB134.0.barley\|gb157\|BE437407_T1 | barley | 311 | | |
| | | | | 312 | | protein Bioinformatics & Protein Curated |
| 122 | MAB135 | MAB135.0.lotus\|gb157\|AI967693_T1 | lotus | 313 | | |
| 123 | | MAB135.1.lotus\|gb157.2\|AI967693_T1 | lotus | 314 | updated to production gb157.2 | updated to production gb157.2 |
| 124 | MAB136 | MAB136.0.rice\|gb157\|AK058573_T1 | rice | 315 | | |
| 125 | | MAB136.1.rice\|gb157.2\|AK058573_T1 | rice | 316 | updated to production gb157.2 | updated to production gb157.2 |
| 126 | MAB137 | MAB137.0.barley\|gb157\|AL508624_T1 | barley | 317 | from provisional patent | |
| 127 | | MAB137.1.barley\|gb157.2\|AL508624_T1 | barley | 318 | updated to production gb157.2 | updated to production gb157.2 |
| 128 | MAB138 | MAB138.0.potato\|gb157\|BI177281_T1 | potato | 319 | from provisional patent | |
| 129 | | MAB138.1.potato\|gb157.2\|BI177281_T1 | potato | 320 | updated to production gb157.2 | updated to production gb157.2 |
| 130 | MAB139 | MAB139.0.cotton\|gb157.2\|AI727826_T1 | cotton | 321 | from provisional patent | |
| 131 | | MAB139.1.cotton\|gb164\|AI727826_T1 | cotton | 322 | updated to production gb164 | updated to production gb164 |
| 132 | MAB140 | MAB140.0.barley\|gb157\|BI778498_T1 | barley | 323 | from provisional patent | |
| 133 | | MAB140.1.barley\|gb157.2\|BI778498_T1 | barley | 324 | updated to production gb157.2 | updated to production gb157.2 |
| 134 | MAB141 | MAB141.0.barley\|gb157\|BE421008_T1 | barley | 325 | from provisional patent | |
| 135 | MAB142 | MAB142.0.cotton\|gb157.2\|AI055631_T2 | cotton | 326 | from provisional patent | |
| 136 | | MAB142.0.cotton\|gb157.2\|AI055631_T1 | cotton | 327 | from provisional patent | |

TABLE 1-continued

Identified ABST Genes

| SEQ ID NO: Polynucleotide | Gene Name | Cluster Name | Organism | SEQ ID NO: Polypeptide | Polynucleotide Description | Polypeptide Description |
|---|---|---|---|---|---|---|
| 137 | | MAB142.1.cotton\|gb164\|AW187041_T1 | cotton | 328 | updated to production gb164 | updated to production gb164 |
| 138 | MAB143 | MAB143.0.tomato\|gb157\|AI487157_T1 | tomato | 329 | from provisional patent | |
| 139 | | MAB143.1.tomato\|gb164\|AI487157_T1 | tomato | 330 | updated to production gb164 | updated to production gb164 |
| 140 | MAB144 | MAB144.0.grape\|gb157\|CA814960_T1 | grape | 331 | from provisional patent | |
| 141 | | MAB144.1.grape\|gb160\|CA814960_T1 | grape | 332 | updated to production gb160 | updated to production gb160 |
| 142 | MAB145 | MAB145.0.barley\|gb157\|BE413365_T1 | barley | 333 | from provisional patent | |
| 143 | MAB146 | MAB146.0.tomato\|gb157\|AI773927_T1 | tomato | 334 | from provisional patent | |
| 144 | | MAB146.1.tomato\|gb164\|AI773927_T1 | tomato | 335 | updated to production gb164 | updated to production gb164 |
| 145 | MAB147 | MAB147.0.tobacco\|gb157\|EB446189_T1 | tobacco | 336 | | |
| 146 | | MAB147.1.tobacco\|gb162\|EB446189_T1 | tobacco | 337 | updated to production gb162 | updated to production gb162 |
| 147 | MAB148 | MAB148.0.*medicago*\|gb157\|AW256654_T1 | *medicago* | 338 | | |
| 148 | | MAB148.1.*medicago*\|gb157.2\|AW256654_T1 | *medicago* | 339 | updated to production gb157.2 | updated to production gb157.2 |
| 149 | MAB150 | MAB150.0.canola\|gb157\|CD818831_T1 | canola | 340 | | |
| 150 | | MAB150.1.canola\|gb161\|CD818831_T1 | canola | 341 | updated to production gb161 | updated to production gb161 |
| 151 | MAB151 | MAB151.0.potato\|gb157\|BQ513540_T1 | potato | 342 | | |
| 152 | | MAB151.1.potato\|gb157.2\|BQ513540_T1 | potato | 343 | updated to production gb157.2 | updated to production gb157.2 |
| 153 | MAB152 | MAB152.0.grape\|gb157\|BQ798655_T1 | grape | 344 | | |
| 154 | | MAB152.1.grape\|gb160\|BQ798655_T1 | grape | 345 | updated to production gb160 | updated to production gb160 |
| 155 | MAB153 | MAB153.0.sugarcane\|gb157\|BQ533857_T1 | sugarcane | 346 | | |
| 156 | | MAB153.1.sugarcane\|gb157.2\|BQ533857_T1 | sugarcane | 347 | updated to production gb157.2 | updated to production gb157.2 |
| 157 | MAB154 | MAB154.0.sugarcane\|gb157\|BQ537570_T3 | sugarcane | 348 | | |
| 158 | | MAB154.0.sugarcane\|gb157\|BQ537570_T2 | sugarcane | 349 | | |
| 159 | | MAB154.0.sugarcane\|gb157\|BQ537570_T1 | sugarcane | 350 | | |
| 160 | | MAB154.1.sugarcane\|gb157.2\|BQ537570_T1 | sugarcane | 351 | updated to production gb157.2 | updated to production gb157.2 |
| 161 | MAB155 | MAB155.0.*sorghum*\|gb157\|AW676730_T1 | *sorghum* | 352 | | |
| 162 | | MAB155.1.*sorghum*\|gb161.xeno\|AW676730_T1 | *sorghum* | 353 | updated to production gb161.xeno | updated to production gb161.xeno |
| 163 | MAB156 | MAB156.0.tobacco\|gb157\|AB117525_T1 | tobacco | 354 | | |
| 164 | | MAB156.1.tobacco\|gb162\|AB117525_T1 | tobacco | 355 | updated to production gb162 | updated to production gb162 |
| 165 | MAB157 | MAB157.0.sugarcane\|gb157\|BQ533820_T2 | sugarcane | 356 | | |
| 166 | | MAB157.0.sugarcane\|gb157\|BQ533820_T1 | sugarcane | 357 | | |
| 167 | | MAB157.1.sugarcane\|gb157.2\|BQ533820_T1 | sugarcane | 358 | updated to production gb157.2 | updated to production gb157.2 |
| 168 | MAB158 | MAB158.0.cotton\|gb157.2\|AI054450_T1 | cotton | 359 | | |
| 169 | MAB159 | MAB159.0.canola\|gb157\|CD818468_T1 | canola | 360 | | |

TABLE 1-continued

Identified ABST Genes

| SEQ ID NO: Polynucleotide | Gene Name | Cluster Name | Organism | SEQ ID NO: Polypeptide | Polynucleotide Description | Polypeptide Description |
|---|---|---|---|---|---|---|
| 170 | MAB160 | MAB160.0.barley\|gb157\|BF622450_T1 | barley | 361 | | |
| 171 | MAB161 | MAB161.0.poplar\|gb157\|BU896597_T1 | poplar | 362 | | |
| 172 | | MAB161.1.poplar\|gb157.2\|BU896597_T1 | poplar | 363 | updated to production gb157.2 | updated to production gb157.2 |
| 173 | MAB162 | MAB162.0.sugarcane\|gb157\|BU102611_T1 | sugarcane | 364 | | |
| 174 | | MAB162.1.sugarcane\|gb157.2\|BU102611_T1 | sugarcane | 365 | updated to production gb157.2 | updated to production gb157.2 |
| 175 | MAB163 | MAB163.0.barley\|gb157\|AL501813_T1 | barley | 366 | | |
| 176 | | MAB163.1.barley\|gb157.2\|AL501813_T1 | barley | 367 | updated to production gb157.2 | updated to production gb157.2 |
| 177 | MAB164 | MAB164.0.barley\|gb157\|BF253543_T1 | barley | 368 | | |
| 178 | | MAB164.1.barley\|gb157.2\|BF253543_T1 | barley | 369 | updated to production gb157.2 | updated to production gb157.2 |
| 179 | MAB165 | MAB165.0.grape\|gb157\|BQ793123_T1 | grape | 370 | | |
| 180 | MAB166 | MAB166.0.poplar\|gb157\|CV228694_T1 | poplar | 371 | | |
| 181 | | MAB166.1.poplar\|gb157.2\|CV228694_T1 | poplar | 372 | updated to production gb157.2 | updated to production gb157.2 |
| 182 | MAB167 | MAB167.0.canola\|gb157\|CX278043_T1 | canola | 373 | | |
| 183 | | MAB167.1.canola\|gb161\|CX278043_T1 | canola | 374 | updated to production gb161 | updated to production gb161 |
| 184 | MAB168 | MAB168.0.grape\|gb157\|BG273815_T1 | grape | 375 | | |
| 185 | | MAB168.1.grape\|gb160\|BG273815_T1 | grape | 376 | updated to production gb160 | updated to production gb160 |
| 186 | MAB169 | MAB169.0.cotton\|gb157.2\|COTLEA14B_T1 | cotton | 377 | | |
| 187 | | MAB169.1.cotton\|gb164\|COTLEA14B_T1 | cotton | 378 | updated to production gb164 | updated to production gb164 |
| 188 | MAB170 | MAB170.0.barley\|gb157\|BE412505_T1 | barley | 379 | | |
| 189 | | MAB170.1.barley\|gb157.2\|BE412505_T1 | barley | 380 | updated to production gb157.2 | updated to production gb157.2 |
| 190 | MAB171 | MAB171.0.sugarcane\|gb157\|CA123631_T1 | sugarcane | 381 | | |
| 191 | | MAB171.1.sugarcane\|gb157.2\|CA123631_T1 | sugarcane | 382 | updated to production gb157.2 | updated to production gb157.2 |
| 192 | MAB172 | MAB172.0.sugarcane\|gb157\|BQ478980_T1 | sugarcane | 383 | | |
| 193 | | MAB172.0.sugarcane\|gb157\|BQ478980_T2 | sugarcane | 384 | | |
| 194 | MAB173 | MAB173.0.barley\|gb157\|BY836652_T1 | barley | 385 | | |
| 195 | | MAB173.1.barley\|gb157.2\|BY836652_T1 | barley | 386 | updated to production gb157.2 | updated to production gb157.2 |
| 196 | MAB174 | MAB174.0.barley\|gb157\|BG342904_T1 | barley | 387 | | |
| 197 | | MAB174.1.barley\|gb157.2\|BG342904_T1 | barley | 388 | updated to production gb157.2 | updated to production gb157.2 |
| 198 | MAB175 | MAB175.0.tomato\|gb157\|BG126606_T1 | tomato | 389 | | |
| 199 | | MAB175.0.tomato\|gb157\|BG126606_T2 | tomato | 390 | | |
| 200 | | MAB175.1.tomato\|gb164\|BG126606_T1 | tomato | 391 | updated to production gb164 | updated to production gb164 |
| 1653 | MAB66 | MAB66.0.tomato\|gb164\|BG124832_CT1 | tomato | 1651 | | |

Polynucleotides and polypeptides with significant homology to the identified ABST genes have been identified from the databases using BLAST software using the BlastX algorithm. The query nucleotide sequences were SEQ ID NOs:1, 3, 5, 7, 9, 10, 11, 13, 15, 16, 17, 19, 21, 23, 25, 26, 28, 29, 30, 32, 34, 36, 37, 38, 40, 42, 44, 46, 48, 50, 52, 54, 55, 57, 59, 61, 63, 65, 67, 69, 71, 73, 75, 77, 79, 81, 82, 84, 86, 88, 90, 91, 93, 94, 96, 98, 100, 101, 103, 105, 107, 109, 111, 113, 115, 116, 118, 119, 121, 122, 124, 126, 128, 130, 132, 134, 135, 138, 140, 142, 143, 145, 147, 149, 151, 153, 155, 157, 161, 163, 165, 168, 169, 170, 171, 173, 175, 177, 179, 180, 182, 184, 186, 188, 190, 192, 194, 196, 198 and 1653, and the identified ABST homologs are provided in Table 2, below.

TABLE 2

ABST Gene homologs

| Polynucleotide SEQ ID NO: | Cluster name | Organism | Polypeptide SEQ ID NO: | Homolog to a polypeptide encoded by polynucleotide SEQ ID NO. | % Global identity |
|---|---|---|---|---|---|
| 392 | apple\|gb157.3\|CN444532_T1 | apple | 961 | Seq357.MAB157.15.sugarcane | 85 |
| 393 | apple\|gb157.3\|CN445371_T1 | apple | 962 | Seq376.MAB168.15.grape | 87 |
| 394 | apple\|gb157.3\|CN878026_T1 | apple | 963 | Seq350.MAB154.15.sugarcane | 80 |
| 395 | apple\|gb157.3\|CK900582_T1 | apple | 964 | Seq321.MAB139.15.cotton | 85 |
| 396 | apple\|gb157.3\|CN888579_T2 | apple | 965 | Seq256.MAB37.15.tomato | 86 |
| 397 | apple\|gb157.3\|CN888579_T3 | apple | 966 | Seq256.MAB37.15.tomato | 81 |
| 398 | apple\|gb157.3\|CO066535_T1 | apple | 967 | Seq370.MAB165.15.grape | 84 |
| 399 | apple\|gb157.3\|CN888579_T1 | apple | 968 | Seq256.MAB37.15.tomato | 86 |
| 400 | apple\|gb157.3\|CN496860_T1 | apple | 969 | Seq321.MAB139.15.cotton | 81 |
| 401 | apricot\|gb157.2\|BQ134642_T1 | apricot | 970 | Seq329.MAB143.15.tomato | 82 |
| 402 | apricot\|gb157.2\|CB822088_T1 | apricot | 971 | Seq256.MAB37.15.tomato | 88 |
| 403 | aquilegia\|gb157.3\|DR915383_T1 | aquilegia | 972 | Seq321.MAB139.15.cotton | 83 |
| 404 | aquilegia\|gb157.3\|DR913600_T1 | aquilegia | 973 | Seq344.MAB152.15.grape | 83 |
| 405 | aquilegia\|gb157.3\|DR920101_T1 | aquilegia | 974 | Seq370.MAB165.15.grape | 87 |
| 406 | aquilegia\|gb157.3\|DT727583_T1 | aquilegia | 975 | Seq311.MAB134.15.barley | 80 |
| 407 | aquilegia\|gb157.3\|DR918523_T1 | aquilegia | 976 | Seq376.MAB168.15.grape | 82 |
| 408 | arabidopsis\|gb165\|AT1G67890_T2 | arabidopsis | 977 | Seq263.MAB42.15.sorghum | 80 |
| 409 | arabidopsis\|gb165\|AT1G78070_T2 | arabidopsis | 978 | Seq207.MAB6.15.arabidopsis | 97 |
| 410 | arabidopsis\|gb165\|AT1G52890_T3 | arabidopsis | 979 | Seq211.MAB9.15.arabidopsis | 85 |
| 411 | arabidopsis\|gb165\|AT3G06620_T1 | arabidopsis | 980 | Seq357.MAB157.15.sugarcane | 80 |
| 412 | arabidopsis\|gb165\|AT1G67890_T1 | arabidopsis | 981 | Seq263.MAB42.15.sorghum | 80 |
| 413 | arabidopsis\|gb165\|AT5G14860_T1 | arabidopsis | 982 | Seq341.MAB150.15.canola | 80 |
| 414 | arabidopsis\|gb165\|AT5G49470_T2 | arabidopsis | 983 | Seq263.MAB42.15.sorghum | 81 |
| 415 | arabidopsis\|gb165\|AT5G49470_T1 | arabidopsis | 984 | Seq263.MAB42.15.sorghum | 81 |
| 416 | arabidopsis\|gb165\|AT3G24170_T1 | arabidopsis | 985 | Seq376.MAB168.15.grape | 80 |
| 417 | arabidopsis\|gb165\|AT1G11670_T1 | arabidopsis | 986 | Seq229.MAB20.15.arabidopsis | 84 |
| 418 | arabidopsis\|gb165\|AT3G25230_T1 | arabidopsis | 987 | Seq370.MAB165.15.grape | 80 |
| 419 | arabidopsis\|gb165\|AT4G32500_T2 | arabidopsis | 988 | Seq242.MAB29.15.arabidopsis | 81 |
| 420 | arabidopsis\|gb165\|AT5G06760_T1 | arabidopsis | 989 | Seq373.MAB167.15.canola | 84 |
| 421 | arabidopsis\|gb165\|AT4G27410_T3 | arabidopsis | 990 | Seq211.MAB9.15.arabidopsis | 94 |
| 422 | arabidopsis\|gb165\|AT4G27560_T1 | arabidopsis | 991 | Seq254.MAB36.15.arabidopsis | 94 |
| 423 | artemisia\|gb164\|EY047508_T1 | artemisia | 992 | Seq321.MAB139.15.cotton | 80 |
| 424 | artemisia\|gb164\|EY060376_T1 | artemisia | 993 | Seq376.MAB168.15.grape | 85 |
| 425 | artemisia\|gb164\|EY089381_T1 | artemisia | 994 | Seq256.MAB37.15.tomato | 86 |
| 426 | artemisia\|gb164\|EY042537_T1 | artemisia | 995 | Seq349.MAB154.15.sugarcane | 80 |
| 427 | b_juncea\|gb164\|EVGN00102008310737_T1 | b_juncea | 996 | Seq360.MAB159.15.canola | 97 |
| 428 | b_juncea\|gb164\|EVGN08486004170336_T1 | b_juncea | 997 | Seq373.MAB167.15.canola | 94 |
| 429 | b_juncea\|gb164\|EVGN00429914360666_T1 | b_juncea | 998 | Seq370.MAB165.15.grape | 83 |
| 430 | b_juncea\|gb164\|EVGN00258430752139Pl_T1 | b_juncea | 999 | Seq376.MAB168.15.grape | 80 |
| 431 | b_juncea\|gb164\|EVGN01568909822952_T1 | b_juncea | 1000 | Seq373.MAB167.15.canola | 98 |
| 432 | b_oleracea\|gb161\|DY029719_T1 | b_oleracea | 1001 | Seq370.MAB165.15.grape | 82 |
| 433 | b_oleracea\|gb161\|AM385106_T1 | b_oleracea | 1002 | Seq360.MAB159.15.canola | 96 |
| 434 | b_oleracea\|gb161\|AM387179_T1 | b_oleracea | 1003 | Seq360.MAB159.15.canola | 91 |
| 435 | b_oleracea\|gb161\|AM061306_T1 | b_oleracea | 1004 | Seq284.MAB100.15.arabidopsis | 86 |
| 436 | b_oleracea\|gb161\|AB125639_T1 | b_oleracea | 1005 | Seq376.MAB168.15.grape | 80 |
| 437 | b_rapa\|gb162\|EE523634_T1 | b_rapa | 1006 | Seq229.MAB20.15.arabidopsis | 92 |
| 438 | b_rapa\|gb162\|EX024909_T1 | b_rapa | 1007 | Seq217.MAB13.15.arabidopsis | 83 |
| 439 | b_rapa\|gb162\|EX070158_T2 | b_rapa | 1008 | Seq211.MAB9.15.arabidopsis | 95 |
| 440 | b_rapa\|gb162\|CA992067_T1 | b_rapa | 1009 | Seq360.MAB159.15.canola | 94 |
| 441 | b_rapa\|gb162\|EE520623_T1 | b_rapa | 1010 | Seq280.MAB91.10.arabidopsis | 89 |
| 442 | b_rapa\|gb162\|CV545896_T1 | b_rapa | 1011 | Seq208.MAB7.15.arabidopsis | 88 |
| 443 | b_rapa\|gb162\|CO749564_T1 | b_rapa | 1012 | Seq370.MAB165.15.grape | 82 |
| 444 | b_rapa\|gb162\|CV434105_T1 | b_rapa | 1013 | Seq217.MAB13.15.arabidopsis | 83 |
| 445 | b_rapa\|gb162\|AF008441_T1 | b_rapa | 1014 | Seq376.MAB168.15.grape | 80 |
| 446 | b_rapa\|gb162\|EX070158_T1 | b_rapa | 1015 | Seq211.MAB9.15.arabidopsis | 86 |
| 447 | b_rapa\|gb162\|EX088727_T1 | b_rapa | 1016 | Seq271.MAB46.15.arabidopsis | 93 |
| 448 | b_rapa\|gb162\|BG544469_T1 | b_rapa | 1017 | Seq360.MAB159.15.canola | 82 |
| 449 | b_rapa\|gb162\|DN962625_T1 | b_rapa | 1018 | Seq237.MAB25.15.arabidopsis | 85 |
| 450 | b_rapa\|gb162\|CV544672_T1 | b_rapa | 1019 | Seq284.MAB100.15.arabidopsis | 88 |
| 451 | barley\|gb157.2\|BI947678_T1 | barley | 1020 | Seq368.MAB164.15.barley | 92 |
| 452 | barley\|gb157.2\|AV835424_T1 | barley | 1021 | Seq257.MAB38.15.wheat | 97 |
| 453 | barley\|gb157.2\|BE455969_T1 | barley | 1022 | Seq290.MAB122.15.maize | 84 |
| 454 | barley\|gb157.2\|BE519575_T2 | barley | 1023 | Seq263.MAB42.15.sorghum | 81 |
| 455 | barley\|gb157.2\|BF625959_T1 | barley | 1024 | Seq221.MAB15.15.sorghum | 83 |
| 456 | barley\|gb157.2\|B0461470_T1 | barley | 1025 | Seq356.MAB157.15.sugarcane | 82 |
| 457 | basilicum\|gb157.3\|DY333033_T1 | basilicum | 1026 | Seq256.MAB37.15.tomato | 87 |
| 458 | bean\|gb164\|CB542809_T1 | bean | 1027 | Seq376.MAB168.15.grape | 80 |
| 459 | bean\|gb164\|CV529652_T1 | bean | 1028 | Seq370.MAB165.15.grape | 83 |
| 460 | bean\|gb164\|CB543453_T1 | bean | 1029 | Seq368.MAB164.15.barley | 80 |
| 461 | bean\|gb164\|CV535253_T1 | bean | 1030 | Seq256.MAB37.15.tomato | 88 |
| 462 | beet\|gb162\|BQ592516_T1 | beet | 1031 | Seq256.MAB37.15.tomato | 86 |
| 463 | beet\|gb162\|BQ488223_T1 | beet | 1032 | Seq211.MAB9.15.arabidopsis | 88 |
| 464 | beet\|gb162\|BQ583768_T1 | beet | 1033 | Seq385.MAB173.15.barley | 85 |

TABLE 2-continued

ABST Gene homologs

| Polynucleotide SEQ ID NO: | Cluster name | Organism | Polypeptide SEQ ID NO: | Homolog to a polypeptide encoded by polynucleotide SEQ ID NO. | % Global identity |
|---|---|---|---|---|---|
| 465 | beet\|gb162\|BQ591963_T1 | beet | 1034 | Seq368.MAB164.15.barley | 80 |
| 466 | brachypodium\|gb161.xeno\|BE519575_T1 | brachypodium | 1035 | Seq356.MAB157.15.sugarcane | 85 |
| 467 | brachypodium\|gb161.xeno\|BG368321_T1 | brachypodium | 1036 | Seq247.MAB32.15.rice | 81 |
| 468 | brachypodium\|gb161.xeno\|BE400652_T1 | brachypodium | 1037 | Seq368.MAB164.15.barley | 95 |
| 469 | brachypodium\|gb161.xeno\|AI502884_T1 | brachypodium | 1038 | Seq210.MAB8.15.rice | 82 |
| 470 | brachypodium\|gb161.xeno\|BY836652_T1 | brachypodium | 1039 | Seq385.MAB173.15.barley | 90 |
| 471 | brachypodium\|gb161.xeno\|BE414917_T1 | brachypodium | 1040 | Seq309.MAB133.15.barley | 93 |
| 472 | brachypodium\|gb161.xeno\|BF202085_T1 | brachypodium | 1041 | Seq291.MAB123.15.barley | 83 |
| 473 | brachypodium\|gb161.xeno\|BE406378_T1 | brachypodium | 1042 | Seq219.MAB14.15.rice | 80 |
| 474 | brachypodium\|gb161.xeno\|BE517562_T1 | brachypodium | 1043 | Seq366.MAB163.15.barley | 85 |
| 475 | brachypodium\|gb161.xeno\|BE420294_T1 | brachypodium | 1044 | Seq290.MAB122.15.maize | 85 |
| 476 | brachypodium\|gb161.xeno\|BG369416_T1 | brachypodium | 1045 | Seq270.MAB45.15.wheat | 89 |
| 477 | brachypodium\|gb161.xeno\|BE406039_T2 | brachypodium | 1046 | Seq241.MAB28.15.rice | 93 |
| 478 | brachypodium\|gb161.xeno\|BE418087_T1 | brachypodium | 1047 | Seq325.MAB141.15.barley | 86 |
| 479 | brachypodium\|gb161.xeno\|BE470780_T1 | brachypodium | 1048 | Seq221.MAB15.15.sorghum | 81 |
| 480 | brachypodium\|gb161.xeno\|AV835424_T1 | brachypodium | 1049 | Seq257.MAB38.15.wheat | 93 |
| 481 | brachypodium\|gb161.xeno\|BE398656_T1 | brachypodium | 1050 | Seq308.MAB132.15.barley | 93 |
| 482 | brachypodium\|gb161.xeno\|BE437407_T1 | brachypodium | 1051 | Seq311.MAB134.15.barley | 98 |
| 483 | brachypodium\|gb161.xeno\|BE406039_T3 | brachypodium | 1052 | Seq333.MAB145.15.barley | 81 |
| 484 | brachypodium\|gb161.xeno\|BE490408_T1 | brachypodium | 1053 | Seq264.MAB42.10.sorghum | 80 |
| 485 | brachypodium\|gb161.xeno\|BE403745_T1 | brachypodium | 1054 | Seq379.MAB170.15.barley | 92 |
| 486 | brachypodium\|gb161.xeno\|BE490591_T1 | brachypodium | 1055 | Seq366.MAB163.15.barley | 87 |
| 487 | brachypodium\|gb161.xeno\|BQ461470_T2 | brachypodium | 1056 | Seq356.MAB157.15.sugarcane | 85 |
| 488 | brachypodium\|gb161.xeno\|BE517562_T2 | brachypodium | 1057 | Seq366.MAB163.15.barley | 83 |
| 489 | brachypodium\|gb161.xeno\|BE413341_T1 | brachypodium | 1058 | Seq336.MAB147.15.tobacco | 80 |
| 490 | brachypodium\|gb161.xeno\|BE515529_T1 | brachypodium | 1059 | Seq259.MAB39.15.barley | 96 |
| 491 | brachypodium\|gb161.xeno\|DV471778_T1 | brachypodium | 1060 | Seq348.MAB154.15.sugarcane | 83 |
| 492 | canola\|gb161\|EL587045_T1 | canola | 1061 | Seq277.MAB50.15.arabidopsis | 87 |
| 493 | canola\|gb161\|CX279297_T1 | canola | 1062 | Seq280.MAB91.10.arabidopsis | 85 |
| 494 | canola\|gb161\|CD815143_T1 | canola | 1063 | Seq222.MAB16.15.rice | 80 |
| 495 | canola\|gb161\|CD831036_T1 | canola | 1064 | Seq284.MAB100.15.arabidopsis | 86 |
| 496 | canola\|gb161\|EE466962_T1 | canola | 1065 | Seq360.MAB159.15.canola | 83 |
| 497 | canola\|gb161\|CN726580_T1 | canola | 1066 | Seq305.MAB130.15.canola | 89 |
| 498 | canola\|gb161\|CD829644_T1 | canola | 1067 | Seq373.MAB167.15.canola | 86 |
| 499 | canola\|gb161\|AY245887_T1 | canola | 1068 | Seq211.MAB9.15.arabidopsis | 87 |
| 500 | canola\|gb161\|EE411591_T1 | canola | 1069 | Seq207.MAB6.15.arabidopsis | 88 |
| 501 | canola\|gb161\|DY020345_T1 | canola | 1070 | Seq211.MAB9.15.arabidopsis | 92 |
| 502 | canola\|gb161\|CD820718_T1 | canola | 1071 | Seq360.MAB159.15.canola | 95 |
| 503 | canola\|gb161\|CX189134_T1 | canola | 1072 | Seq221.MAB15.15.sorghum | 81 |
| 504 | canola\|gb161\|EG021120_T1 | canola | 1073 | Seq360.MAB159.15.canola | 83 |
| 505 | canola\|gb161\|ES906182_T1 | canola | 1074 | Seq244.MAB30.15.arabidopsis | 92 |
| 506 | canola\|gb161\|ES911977_T1 | canola | 1075 | Seq229.MAB20.15.arabidopsis | 88 |
| 507 | canola\|gb161\|CD814410_T1 | canola | 1076 | Seq217.MAB13.15.arabidopsis | 81 |
| 508 | canola\|gb161\|ES904177_T1 | canola | 1077 | Seq208.MAB7.15.arabidopsis | 87 |
| 509 | canola\|gb161\|CD813775_T1 | canola | 1078 | Seq370.MAB165.15.grape | 82 |
| 510 | canola\|gb161\|CD824419_T1 | canola | 1079 | Seq229.MAB20.15.arabidopsis | 94 |
| 511 | canola\|gb161\|CD825454_T1 | canola | 1080 | Seq229.MAB20.15.arabidopsis | 90 |
| 512 | canola\|gb161\|CD834184_T1 | canola | 1081 | Seq284.MAB100.15.arabidopsis | 88 |
| 513 | canola\|gb161\|EE469078_T1 | canola | 1082 | Seq370.MAB165.15.grape | 83 |
| 514 | canola\|gb161\|GFXAJ535111X1_T1 | canola | 1083 | Seq305.MAB130.15.canola | 99 |
| 515 | canola\|gb161\|EE448267_T1 | canola | 1084 | Seq222.MAB16.15.rice | 80 |
| 516 | canola\|gb161\|CX193415_T1 | canola | 1085 | Seq237.MAB25.15.arabidopsis | 85 |
| 517 | canola\|gb161\|CD813278_T1 | canola | 1086 | Seq375.MAB168.15.grape | 80 |
| 518 | castorbean\|gb160\|MDL28401M000077_T1 | castorbean | 1087 | Seq370.MAB165.15.grape | 86 |
| 519 | castorbean\|gb160\|EE258294_T1 | castorbean | 1088 | Seq256.MAB37.15.tomato | 87 |
| 520 | castorbean\|gb160\|MDL28066M000021_T1 | castorbean | 1089 | Seq370.MAB165.15.grape | 85 |
| 521 | castorbean\|gb160\|AM267339_T1 | castorbean | 1090 | Seq222.MAB16.15.rice | 80 |
| 522 | castorbean\|gb160\|EG659656_T1 | castorbean | 1091 | Seq376.MAB168.15.grape | 83 |
| 523 | castorbean\|gb160\|EG656754_T1 | castorbean | 1092 | Seq263.MAB42.15.sorghum | 82 |
| 524 | castorbean\|gb160\|EE259826_T1 | castorbean | 1093 | Seq362.MAB161.15.poplar | 83 |
| 525 | castorbean\|gb160\|EG659299_T1 | castorbean | 1094 | Seq300.MAB127.15.grape | 81 |
| 526 | castorbean\|gb160\|EE259565_T1 | castorbean | 1095 | Seq276.MAB49.15.maize | 80 |
| 527 | castorbean\|gb160\|EE255133_T1 | castorbean | 1096 | Seq321.MAB139.15.cotton | 84 |
| 528 | castorbean\|gb160\|MDL29822M003364_T1 | castorbean | 1097 | Seq336.MAB147.15.tobacco | 82 |
| 529 | castorbean\|gb160\|EG661241_T1 | castorbean | 1098 | Seq371.MAB166.15.poplar | 85 |
| 530 | centaurea\|gb161\|EH713943_T1 | centaurea | 1099 | Seq321.MAB139.15.cotton | 82 |
| 531 | centaurea\|gb161\|EH724589_T1 | centaurea | 1100 | Seq256.MAB37.15.tomato | 84 |
| 532 | centaurea\|gb161\|EH717520_T1 | centaurea | 1101 | Seq329.MAB143.15.tomato | 80 |
| 533 | centaurea\|gb161\|EH711566_T1 | centaurea | 1102 | Seq370.MAB165.15.grape | 81 |
| 534 | centaurea\|gb161\|EH713337_T1 | centaurea | 1103 | Seq259.MAB39.15.barley | 81 |
| 535 | centaurea\|gb161\|EH713628_T1 | centaurea | 1104 | Seq376.MAB168.15.grape | 83 |
| 536 | centaurea\|gb161\|EH738263_T1 | centaurea | 1105 | Seq385.MAB173.15.barley | 80 |
| 537 | centaurea\|gb161\|EH727723_T1 | centaurea | 1106 | Seq256.MAB37.15.tomato | 84 |

TABLE 2-continued

ABST Gene homologs

| Polynucleotide SEQ ID NO: | Cluster name | Organism | Polypeptide SEQ ID NO: | Homolog to a polypeptide encoded by polynucleotide SEQ ID NO. | % Global identity |
|---|---|---|---|---|---|
| 538 | cichorium\|gb161\|DT212291_T1 | cichorium | 1107 | Seq370.MAB165.15.grape | 80 |
| 539 | cichorium\|gb161\|DT211081_T1 | cichorium | 1108 | Seq376.MAB168.15.grape | 83 |
| 540 | cichorium\|gb161\|EH692437_T1 | cichorium | 1109 | Seq256.MAB37.15.tomato | 86 |
| 541 | cichorium\|gb161\|DT212218_T1 | cichorium | 1110 | Seq256.MAB37.15.tomato | 89 |
| 542 | citrus\|gb157.2\|CB290836_T1 | citrus | 1111 | Seq376.MAB168.15.grape | 85 |
| 543 | citrus\|gb157.2\|BQ624861_T1 | citrus | 1112 | Seq276.MAB49.15.maize | 82 |
| 544 | citrus\|gb157.2\|BQ624727_T1 | citrus | 1113 | Seq370.MAB165.15.grape | 85 |
| 545 | citrus\|gb157.2\|CB290836_T2 | citrus | 1114 | Seq376.MAB168.15.grape | 86 |
| 546 | citrus\|gb157.2\|CX672218_T2 | citrus | 1115 | Seq357.MAB157.15.sugarcane | 83 |
| 547 | citrus\|gb157.2\|CF504250_T1 | citrus | 1116 | Seq222.MAB16.15.rice | 82 |
| 548 | citrus\|gb157.2\|CK933948_T1 | citrus | 1117 | Seq256.MAB37.15.tomato | 86 |
| 549 | clover\|gb162\|BB926896_T1 | clover | 1118 | Seq256.MAB37.15.tomato | 82 |
| 550 | clover\|gb162\|BB904696_T1 | clover | 1119 | Seq263.MAB42.15.sorghum | 84 |
| 551 | coffea\|gb157.2\|DV676382_T1 | coffea | 1120 | Seq256.MAB37.15.tomato | 91 |
| 552 | coffea\|gb157.2\|DV688680_T1 | coffea | 1121 | Seq332.MAB144.15.grape | 83 |
| 553 | coffea\|gb157.2\|DQ124044_T1 | coffea | 1122 | Seq303.MAB129.15.tomato | 80 |
| 554 | cotton\|gb164\|BF268276_T1 | cotton | 1123 | Seq370.MAB165.15.grape | 84 |
| 555 | cotton\|gb164\|CO113031_T1 | cotton | 1124 | Seq319.MAB138.15.potato | 80 |
| 556 | cotton\|gb164\|AI730186_T1 | cotton | 1125 | Seq256.MAB37.15.tomato | 81 |
| 557 | cotton\|gb164\|CO103100_T1 | cotton | 1126 | Seq256.MAB37.15.tomato | 86 |
| 558 | cotton\|gb164\|BE051970_T1 | cotton | 1127 | Seq370.MAB165.15.grape | 84 |
| 559 | cotton\|gb164\|AI725698_T1 | cotton | 1128 | Seq376.MAB168.15.grape | 85 |
| 560 | cotton\|gb164\|AI728290_T1 | cotton | 1129 | Seq370.MAB165.15.grape | 82 |
| 561 | cotton\|gb164\|AI055482_T1 | cotton | 1130 | Seq370.MAB165.15.grape | 85 |
| 562 | cotton\|gb164\|ES794517_T1 | cotton | 1131 | Seq327.MAB142.15.cotton | 81 |
| 563 | cotton\|gb164\|BF268276_T2 | cotton | 1132 | Seq370.MAB165.15.grape | 84 |
| 564 | cotton\|gb164\|CO109448_T1 | cotton | 1133 | Seq376.MAB168.15.grape | 83 |
| 565 | cotton\|gb164\|DT459182_T1 | cotton | 1134 | Seq375.MAB168.15.grape | 84 |
| 566 | cotton\|gb164\|BG441162_T1 | cotton | 1135 | Seq256.MAB37.15.tomato | 85 |
| 567 | cowpea\|gb165\|FF390508_T1 | cowpea | 1136 | Seq256.MAB37.15.tomato | 84 |
| 568 | cowpea\|gb165\|FF390203_T1 | cowpea | 1137 | Seq259.MAB39.15.barley | 86 |
| 569 | cowpea\|gb165\|DQ267475_T1 | cowpea | 1138 | Seq376.MAB168.15.grape | 83 |
| 570 | cowpea\|gb165\|FF382851_T1 | cowpea | 1139 | Seq224.MAB17.15.soybean | 89 |
| 571 | cowpea\|gb165\|FF394009_T1 | cowpea | 1140 | Seq370.MAB165.15.grape | 85 |
| 572 | dandelion\|gb161\|DQ160099_T1 | dandelion | 1141 | Seq376.MAB168.15.grape | 82 |
| 573 | dandelion\|gb161\|DY823013_T1 | dandelion | 1142 | Seq256.MAB37.15.tomato | 82 |
| 574 | dandelion\|gb161\|DY820394_T2 | dandelion | 1143 | Seq256.MAB37.15.tomato | 88 |
| 575 | dandelion\|gb161\|DY813450_T2 | dandelion | 1144 | Seq256.MAB37.15.tomato | 85 |
| 576 | dandelion\|gb161\|DY820394_1 | dandelion | 1145 | Seq256.MAB37.15.tomato | 87 |
| 577 | fescue\|gb161\|DT687914_T1 | fescue | 1146 | Seq290.MAB122.15.maize | 93 |
| 578 | fescue\|gb161\|DT702477_T1 | fescue | 1147 | Seq291.MAB123.15.barley | 87 |
| 579 | fescue\|gb161\|DT705881_T1 | fescue | 1148 | Seq311.MAB134.15.barley | 96 |
| 580 | fescue\|gb161\|DT682501_T1 | fescue | 1149 | Seq321.MAB139.15.cotton | 82 |
| 581 | fescue\|gb161\|DT699000_T1 | fescue | 1150 | Seq309.MAB133.15.barley | 90 |
| 582 | fescue\|gb161\|DT706685_T1 | fescue | 1151 | Seq259.MAB39.15.barley | 96 |
| 583 | fescue\|gb161\|DT698326_T1 | fescue | 1152 | Seq368.MAB164.15.barley | 95 |
| 584 | fescue\|gb161\|DT677453_T1 | fescue | 1153 | Seq379.MAB170.15.barley | 95 |
| 585 | fescue\|gb161\|DT674734_T1 | fescue | 1154 | Seq333.MAB145.15.barley | 88 |
| 586 | ginger\|gb164\|DY377113_T1 | ginger | 1155 | Seq223.MAB16.15.rice | 81 |
| 587 | grape\|gb160\|BQ792651_T1 | grape | 1156 | Seq222.MAB16.15.rice | 84 |
| 588 | grape\|gb160\|BQ793581_T1 | grape | 1157 | Seq371.MAB166.15.poplar | 80 |
| 589 | iceplant\|gb164\|BM658279_T1 | iceplant | 1158 | Seq376.MAB168.15.grape | 83 |
| 590 | iceplant\|gb164\|BE034140_T1 | iceplant | 1159 | Seq303.MAB129.15.tomato | 81 |
| 591 | ipomoea\|gb157.2\|AU224303_T1 | ipomoea | 1160 | Seq256.MAB37.15.tomato | 91 |
| 592 | ipomoea\|gb157.2\|AU224807_T1 | ipomoea | 1161 | Seq385.MAB173.15.barley | 80 |
| 593 | ipomoea\|gb157.2\|CJ758382_T1 | ipomoea | 1162 | Seq371.MAB166.15.poplar | 83 |
| 594 | lettuce\|gb157.2\|DW048067_T1 | lettuce | 1163 | Seq256.MAB37.15.tomato | 87 |
| 595 | lettuce\|gb157.2\|DW046482_T1 | lettuce | 1164 | Seq256.MAB37.15.tomato | 85 |
| 596 | lettuce\|gb157.2\|DW062524_T1 | lettuce | 1165 | Seq259.MAB39.15.barley | 81 |
| 597 | lettuce\|gb157.2\|DW048641_T1 | lettuce | 1166 | Seq370.MAB165.15.grape | 80 |
| 598 | lettuce\|gb157.2\|DW055618_T1 | lettuce | 1167 | Seq371.MAB166.15.poplar | 80 |
| 599 | lettuce\|gb157.2\|DY961700_T2 | lettuce | 1168 | Seq211.MAB9.15.arabidopsis | 83 |
| 600 | lettuce\|gb157.2\|DW075962_T1 | lettuce | 1169 | Seq256.MAB37.15.tomato | 87 |
| 601 | lettuce\|gb157.2\|DW047202_T1 | lettuce | 1170 | Seq376.MAB168.15.grape | 83 |
| 602 | lotus\|gb157.2\|BF177835_T1 | lotus | 1171 | Seq256.MAB37.15.tomato | 90 |
| 603 | lotus\|gb157.2\|BW601503_T1 | lotus | 1172 | Seq211.MAB9.15.arabidopsis | 84 |
| 604 | maize\|gb164\|T15319_T2 | maize | 1173 | Seq276.MAB49.15.maize | 96 |
| 605 | maize\|gb164\|AI649734_T1 | maize | 1174 | Seq264.MAB42.10.sorghum | 90 |
| 606 | maize\|gb164\|BE638692_T1 | maize | 1175 | Seq228.MAB19.15.sorghum | 88 |
| 607 | maize\|gb164\|AW498283_T1 | maize | 1176 | Seq210.MAB8.15.rice | 80 |
| 608 | maize\|gb164\|AI622375_T1 | maize | 1177 | Seq309.MAB133.15.barley | 90 |
| 609 | maize\|gb164\|BQ034409_T1 | maize | 1178 | Seq290.MAB122.15.maize | 100 |
| 610 | maize\|gb164\|EC895235_T1 | maize | 1179 | Seq210.MAB8.15.rice | 86 |

TABLE 2-continued

ABST Gene homologs

| Polynucleotide SEQ ID NO: | Cluster name | Organism | Polypeptide SEQ ID NO: | Homolog to a polypeptide encoded by polynucleotide SEQ ID NO. | % Global identity |
|---|---|---|---|---|---|
| 611 | maize\|gb164\|AI947795_T2 | maize | 1180 | Seq325.MAB141.15.barley | 80 |
| 612 | maize\|gb164\|AI947974_T1 | maize | 1181 | Seq227.MAB19.15.sorghum | 93 |
| 613 | maize\|gb164\|AI619086_T1 | maize | 1182 | Seq346.MAB153.15.sugarcane | 95 |
| 614 | maize\|gb164\|AA143925_T1 | maize | 1183 | Seq221.MAB15.15.sorghum | 94 |
| 615 | maize\|gb164\|AW179463_T1 | maize | 1184 | Seq321.MAB139.15.cotton | 82 |
| 616 | maize\|gb164\|BE051802_T1 | maize | 1185 | Seq231.MAB21.15.rice | 89 |
| 617 | maize\|gb164\|AI942091_T1 | maize | 1186 | Seq309.MAB133.15.barley | 89 |
| 618 | maize\|gb164\|AI944064_T1 | maize | 1187 | Seq383.MAB172.15.sugarcane | 96 |
| 619 | maize\|gb164\|T15319_T1 | maize | 1188 | Seq276.MAB49.15.maize | 96 |
| 620 | maize\|gb164\|AI782993_T1 | maize | 1189 | Seq241.MAB28.15.rice | 82 |
| 621 | maize\|gb164\|T26945_T1 | maize | 1190 | Seq370.MAB165.15.grape | 80 |
| 622 | maize\|gb164\|AI941749_T1 | maize | 1191 | Seq269.MAB45.15.wheat | 91 |
| 623 | maize\|gb164\|AI891255_T1 | maize | 1192 | Seq311.MAB134.15.barley | 95 |
| 624 | maize\|gb164\|CD975046_T1 | maize | 1193 | Seq203.MAB3.15.rice | 88 |
| 625 | maize\|gb164\|AW360563_T1 | maize | 1194 | Seq241.MAB28.15.rice | 81 |
| 626 | maize\|gb164\|AI901860_T1 | maize | 1195 | Seq259.MAB39.15.barley | 85 |
| 627 | maize\|gb164\|AI948098_T1 | maize | 1196 | Seq381.MAB171.15.sugarcane | 95 |
| 628 | maize\|gb164\|AI444730_T1 | maize | 1197 | Seq241.MAB28.15.rice | 83 |
| 629 | maize\|gb164\|AW216308_T1 | maize | 1198 | Seq288.MAB121.15.sugarcane | 89 |
| 630 | maize\|gb164\|BM268089_T1 | maize | 1199 | Seq381.MAB171.15.sugarcane | 92 |
| 631 | maize\|gb164\|AI438597_T1 | maize | 1200 | Seq352.MAB155.15.sorghum | 91 |
| 632 | maize\|gb164\|AW927739_T1 | maize | 1201 | Seq350.MAB154.15.sugarcane | 97 |
| 633 | maize\|gb164\|AI891255_T2 | maize | 1202 | Seq311.MAB134.15.barley | 95 |
| 634 | maize\|gb164\|AI920760_T1 | maize | 1203 | Seq286.MAB104.15.rice | 89 |
| 635 | medicago\|gb157.2\|AI974487_T1 | medicago | 1204 | Seq370.MAB165.15.grape | 87 |
| 636 | medicago\|gb157.2\|BE325770_T1 | medicago | 1205 | Seq256.MAB37.15.tomato | 88 |
| 637 | medicago\|gb157.2\|AW685603_T1 | medicago | 1206 | Seq376.MAB168.15.grape | 82 |
| 638 | medicago\|gb157.2\|AL368329_T1 | medicago | 1207 | Seq311.MAB134.15.barley | 80 |
| 639 | medicago\|gb157.2\|AW688497_T1 | medicago | 1208 | Seq370.MAB165.15.grape | 80 |
| 640 | medicago\|gb157.2\|AL37709_T1 | medicago | 1209 | Seq224.MAB17.15.soybean | 80 |
| 641 | medicago\|gb157.2\|AI974241_T1 | medicago | 1210 | Seq334.MAB146.15.tomato | 83 |
| 642 | medicago\|gb157.2\|BF632135_T1 | medicago | 1211 | Seq344.MAB152.15.grape | 85 |
| 643 | melon\|gb165\|DV633691_T1 | melon | 1212 | Seq376.MAB168.15.grape | 80 |
| 644 | melon\|gb165\|DV632564_T1 | melon | 1213 | Seq368.MAB164.15.barley | 80 |
| 645 | melon\|gb165\|DV633584_T1 | melon | 1214 | Seq344.MAB152.15.grape | 86 |
| 646 | melon\|gb165\|AM714958_T1 | melon | 1215 | Seq259.MAB39.15.barley | 81 |
| 647 | nicotiana_benthamiana\|gb162\|EH364164_T1 | nicotiana_benthamiana | 1216 | Seq256.MAB37.15.tomato | 95 |
| 648 | oat\|gb164\|CN816769_T1 | oat | 1217 | Seq368.MAB164.15.barley | 94 |
| 649 | oat\|gb164\|BE439108_T1 | oat | 1218 | Seq312.MAB134.10.barley | 85 |
| 650 | onion\|gb162\|CF437899_T1 | onion | 1219 | Seq256.MAB37.15.tomato | 81 |
| 651 | onion\|gb162\|CF437716_T1 | onion | 1220 | Seq276.MAB49.15.maize | 82 |
| 652 | onion\|gb162\|CF439314_T1 | onion | 1221 | Seq370.MAB165.15.grape | 80 |
| 653 | papaya\|gb165\|EX245596_T1 | papaya | 1222 | Seq370.MAB165.15.grape | 88 |
| 654 | papaya\|gb165\|EX299345_T1 | papaya | 1223 | Seq263.MAB42.15.sorghum | 82 |
| 655 | papaya\|gb165\|EX248971_T1 | papaya | 1224 | Seq362.MAB161.15.poplar | 86 |
| 656 | papaya\|gb165\|EX227965_T1 | papaya | 1225 | Seq332.MAB144.15.grape | 83 |
| 657 | papaya\|gb165\|EX264060_T1 | papaya | 1226 | Seq376.MAB168.15.grape | 89 |
| 658 | papaya\|gb165\|EX291966_T1 | papaya | 1227 | Seq370.MAB165.15.grape | 82 |
| 659 | peach\|gb157.2\|BU039922_T1 | peach | 1228 | Seq300.MAB127.15.grape | 82 |
| 660 | peach\|gb157.2\|BU039373_T1 | peach | 1229 | Seq370.MAB165.15.grape | 83 |
| 661 | peach\|gb157.2\|AJ631618_T1 | peach | 1230 | Seq276.MAB49.15.maize | 80 |
| 662 | peach\|gb157.2\|BU040470_T1 | peach | 1231 | Seq376.MAB168.15.grape | 89 |
| 663 | peach\|gb157.2\|BU039381_T1 | peach | 1232 | Seq256.MAB37.15.tomato | 88 |
| 664 | peanut\|gb161\|ES754023_T1 | peanut | 1233 | Seq332.MAB144.15.grape | 80 |
| 665 | peanut\|gb161\|EH043199_T1 | peanut | 1234 | Seq256.MAB37.15.tomato | 88 |
| 666 | pepper\|gb157.2\|BM063531_T1 | pepper | 1235 | Seq256.MAB37.15.tomato | 96 |
| 667 | pepper\|gb157.2\|BM062846_T1 | pepper | 1236 | Seq221.MAB15.15.sorghum | 82 |
| 668 | pepper\|gb157.2\|BM061776_T1 | pepper | 1237 | Seq329.MAB143.15.tomato | 90 |
| 669 | pepper\|gb157.2\|BM064151_T1 | pepper | 1238 | Seq306.MAB131.15.tomato | 88 |
| 670 | pepper\|gb157.2\|BM061313_T1 | pepper | 1239 | Seq211.MAB9.15.arabidopsis | 86 |
| 671 | pepper\|gb157.2\|BI480604_T1 | pepper | 1240 | Seq276.MAB49.15.maize | 80 |
| 672 | periwinkle\|gb164\|EG559012_T1 | periwinkle | 1241 | Seq259.MAB39.15.barley | 80 |
| 673 | petunia\|gb157.2\|CV292753_T1 | petunia | 1242 | Seq263.MAB42.15.sorghum | 80 |
| 674 | petunia\|gb157.2\|CV298220_T1 | petunia | 1243 | Seq283.MAB99.15.tomato | 81 |
| 675 | pine\|gb157.2\|DR088714_T1 | pine | 1244 | Seq357.MAB157.15.sugarcane | 80 |
| 676 | pine\|gb157.2\|AW290504_T1 | pine | 1245 | Seq344.MAB152.15.grape | 82 |
| 677 | pineapple\|gb157.2\|CO731309_T1 | pineapple | 1246 | Seq222.MAB16.15.rice | 83 |
| 678 | pineapple\|gb157.2\|DT336648_T1 | pineapple | 1247 | Seq376.MAB168.15.grape | 81 |
| 679 | pineapple\|gb157.2\|CO731994_T1 | pineapple | 1248 | Seq219.MAB14.15.rice | 80 |
| 680 | poplar\|gb157.2\|AI162293_T1 | poplar | 1249 | Seq298.MAB126.15.grape | 82 |
| 681 | poplar\|gb157.2\|AI165439_T1 | poplar | 1250 | Seq298.MAB126.15.grape | 80 |
| 682 | poplar\|gb157.2\|AI162293_T3 | poplar | 1251 | Seq298.MAB126.15.grape | 80 |

TABLE 2-continued

ABST Gene homologs

| Poly-nucleotide SEQ ID NO: | Cluster name | Organism | Polypeptide SEQ ID NO: | Homolog to a polypeptide encoded by polynucleotide SEQ ID NO. | % Global identity |
|---|---|---|---|---|---|
| 683 | poplar\|gb157.2\|BI120274_T3 | poplar | 1252 | Seq256.MAB37.15.tomato | 81 |
| 684 | poplar\|gb157.2\|BI120274_T2 | poplar | 1253 | Seq344.MAB152.15.grape | 89 |
| 685 | poplar\|gb157.2\|BF299457_T1 | poplar | 1254 | Seq370.MAB165.15.grape | 85 |
| 686 | poplar\|gb157.2\|BI120274_T1 | poplar | 1255 | Seq344.MAB152.15.grape | 86 |
| 687 | poplar\|gb157.2\|BI122516_T1 | poplar | 1256 | Seq362.MAB161.15.poplar | 90 |
| 688 | poplar\|gb157.2\|BU821689_T1 | poplar | 1257 | Seq321.MAB139.15.cotton | 81 |
| 689 | poplar\|gb157.2\|AI166955_T1 | poplar | 1258 | Seq344.MAB152.15.grape | 87 |
| 690 | poplar\|gb157.2\|BI069450_T1 | poplar | 1259 | Seq376.MAB168.15.grape | 85 |
| 691 | potato\|gb157.2\|BG594910_T1 | potato | 1260 | Seq370.MAB165.15.grape | 82 |
| 692 | potato\|gb157.2\|M487418_T1 | potato | 1261 | Seq321.MAB139.15.cotton | 82 |
| 693 | potato\|gb157.2\|BQ516076_T2 | potato | 1262 | Seq389.MAB175.15.tomato | 97 |
| 694 | potato\|gb157.2\|BE921143_T1 | potato | 1263 | Seq349.MAB154.15.sugarcane | 80 |
| 695 | potato\|gb157.2\|BG592541_T1 | potato | 1264 | Seq256.MAB37.15.tomato | 90 |
| 696 | potato\|gb157.2\|BF052848_T1 | potato | 1265 | Seq321.MAB139.15.cotton | 81 |
| 697 | potato\|gb157.2\|BF460150_T1 | potato | 1266 | Seq370.MAB165.15.grape | 84 |
| 698 | potato\|gb157.2\|BG097985_T1 | potato | 1267 | Seq303.MAB129.15.tomato | 91 |
| 699 | potato\|gb157.2\|BE923564_T1 | potato | 1268 | Seq342.MAB151.15.potato | 90 |
| 700 | potato\|gb157.2\|X86021_T1 | potato | 1269 | Seq334.MAB146.15.tomato | 97 |
| 701 | potato\|gb157.2\|BG594768_T1 | potato | 1270 | Seq329.MAB143.15.tomato | 97 |
| 702 | potato\|gb157.2\|BF154203_T1 | potato | 1271 | Seq256.MAB37.15.tomato | 98 |
| 703 | potato\|gb157.2\|BE344306_T1 | potato | 1272 | Seq357.MAB157.15.sugarcane | 82 |
| 704 | potato\|gb157.2\|BF460309_T1 | potato | 1273 | Seq329.MAB143.15.tomato | 98 |
| 705 | potato\|gb157.2\|BQ516076_T1 | potato | 1274 | Seq390.MAB175.15.tomato | 96 |
| 706 | potato\|gb157.2\|BI176616_T1 | potato | 1275 | Seq256.MAB37.15.tomato | 88 |
| 707 | potato\|gb157.2\|BQ117692_T1 | potato | 1276 | Seq354.MAB156.15.tobacco | 86 |
| 708 | potato\|gb157.2\|AJ487418_T2 | potato | 1277 | Seq321.MAB139.15.cotton | 81 |
| 709 | potato\|gb157.2\|BG351229_T1 | potato | 1278 | Seq357.MAB157.15.sugarcane | 81 |
| 710 | potato\|gb157.2\|M487418_T3 | potato | 1279 | Seq321.MAB139.15.cotton | 84 |
| 711 | potato\|gb157.2\|BF154154_T1 | potato | 1280 | Seq256.MAB37.15.tomato | 99 |
| 712 | radish\|gb164\|EY895633_T1 | radish | 1281 | Seq373.MAB167.15.canola | 93 |
| 713 | radish\|gb164\|EX772944_T1 | radish | 1282 | Seq356.MAB157.15.sugarcane | 83 |
| 714 | radish\|gb164\|EW725846_T1 | radish | 1283 | Seq237.MAB25.15.arabidopsis | 84 |
| 715 | radish\|gb164\|EV527306_T1 | radish | 1284 | Seq229.MAB20.15.arabidopsis | 94 |
| 716 | radish\|gb164\|EV565850_T1 | radish | 1285 | Seq277.MAB50.15.arabidopsis | 90 |
| 717 | radish\|gb164\|EX772722_T1 | radish | 1286 | Seq360.MAB159.15.canola | 88 |
| 718 | radish\|gb164\|EX775718_T1 | radish | 1287 | Seq376.MAB168.15.grape | 81 |
| 719 | radish\|gb164\|EV535278_T1 | radish | 1288 | Seq360.MAB159.15.canola | 81 |
| 720 | radish\|gb164\|EV565334_T1 | radish | 1289 | Seq211.MAB9.15.arabidopsis | 91 |
| 721 | radish\|gb164\|EV528083_T1 | radish | 1290 | Seq252.MAB35.15.arabidopsis | 80 |
| 722 | radish\|gb164\|T25168_T1 | radish | 1291 | Seq376.MAB168.15.grape | 80 |
| 723 | radish\|gb164\|EV544010_T1 | radish | 1292 | Seq229.MAB20.15.arabidopsis | 91 |
| 724 | radish\|gb164\|EW713752_T1 | radish | 1293 | Seq373.MAB167.15.canola | 86 |
| 725 | radish\|gb164\|EV568565_T1 | radish | 1294 | Seq284.MAB100.15.arabidopsis | 88 |
| 726 | radish\|gb164\|EV543867_T1 | radish | 1295 | Seq373.MAB167.15.canola | 88 |
| 727 | radish\|gb164\|EX770974_T1 | radish | 1296 | Seq211.MAB9.15.arabidopsis | 85 |
| 728 | radish\|gb164\|EV566819_T1 | radish | 1297 | Seq217.MAB13.15.arabidopsis | 81 |
| 729 | rice\|gb157.2\|NM001059403_T1 | rice | 1298 | Seq261.MAB40.15.rice | 84 |
| 730 | rice\|gb157.2\|C28755_T1 | rice | 1299 | Seq321.MAB139.15.cotton | 80 |
| 731 | rice\|gb157.2\|AA750806_T1 | rice | 1300 | Seq290.MAB122.15.maize | 83 |
| 732 | rice\|gb157.2\|AA751345_T1 | rice | 1301 | Seq321.MAB139.15.cotton | 80 |
| 733 | rice\|gb157.2\|BE040195_T6 | rice | 1302 | Seq346.MAB153.15.sugarcane | 95 |
| 734 | rice\|gb157.2\|BI118752_T1 | rice | 1303 | Seq276.MAB49.15.maize | 94 |
| 735 | rice\|gb157.2\|AW070148_T1 | rice | 1304 | Seq350.MAB154.15.sugarcane | 87 |
| 736 | rice\|gb157.2\|AW069929_T1 | rice | 1305 | Seq309.MAB133.15.barley | 93 |
| 737 | rice\|gb157.2\|AW070094_T1 | rice | 1306 | Seq274.MAB48.15.rice | 83 |
| 738 | rice\|gb157.2\|AA753115_T4 | rice | 1307 | Seq259.MAB39.15.barley | 90 |
| 739 | rice\|gb157.2\|BI795037_T4 | rice | 1308 | Seq385.MAB173.15.barley | 100 |
| 740 | rice\|gb157.2\|AU092454_T1 | rice | 1309 | Seq274.MAB48.15.rice | 100 |
| 741 | rice\|gb157.2\|AA753115_T3 | rice | 1310 | Seq259.MAB39.15.barley | 91 |
| 742 | rice\|gb157.2\|BE040195_T1 | rice | 1311 | Seq346.MAB153.15.sugarcane | 91 |
| 743 | rice\|gb157.2\|CB624284_T1 | rice | 1312 | Seq264.MAB42.10.sorghum | 82 |
| 744 | rice\|gb157.2\|AU030125_T3 | rice | 1313 | Seq357.MAB157.15.sugarcane | 88 |
| 745 | rice\|gb157.2\|AU164313_T1 | rice | 1314 | Seq270.MAB45.15.wheat | 84 |
| 746 | rice\|gb157.2\|BI799463_T1 | rice | 1315 | Seq221.MAB15.15.sorghum | 85 |
| 747 | rice\|gb157.2\|AW070094_T3 | rice | 1316 | Seq274.MAB48.15.rice | 80 |
| 748 | rice\|gb157.2\|AA753115_T1 | rice | 1317 | Seq259.MAB39.15.barley | 91 |
| 749 | rice\|gb157.2\|AU093322_T2 | rice | 1318 | Seq228.MAB19.15.sorghum | 85 |
| 750 | rice\|gb157.2\|AU030125_T1 | rice | 1319 | Seq263.MAB42.15.sorghum | 80 |
| 751 | rice\|gb157.2\|AA752703_T1 | rice | 1320 | Seq295.MAB125.15.rice | 88 |
| 752 | rice\|gb157.2\|NM001067464_T1 | rice | 1321 | Seq205.MAB4.15.rice | 93 |
| 753 | rice\|gb157.2\|NM001052309_T1 | rice | 1322 | Seq295.MAB125.15.rice | 91 |
| 754 | rice\|gb157.2\|CA763128_T2 | rice | 1323 | Seq219.MAB14.15.rice | 80 |
| 755 | rice\|gb157.2\|AW070148_T2 | rice | 1324 | Seq348.MAB154.15.sugarcane | 87 |

TABLE 2-continued

ABST Gene homologs

| Poly-nucleotide SEQ ID NO: | Cluster name | Organism | Poly-peptide SEQ ID NO: | Homolog to a polypeptide encoded by polynucleotide SEQ ID NO. | % Global identity |
|---|---|---|---|---|---|
| 756 | rice\|gb157.2\|AU093322_T1 | rice | 1325 | Seq228.MAB19.15.sorghum | 86 |
| 757 | rice\|gb157.2\|AA753115_T5 | rice | 1326 | Seq259.MAB39.15.barley | 94 |
| 758 | rice\|gb157.2\|AU030125_T4 | rice | 1327 | Seq263.MAB42.15.sorghum | 80 |
| 759 | rye\|gb164\|BF429408_T1 | rye | 1328 | Seq309.MAB133.15.barley | 97 |
| 760 | rye\|gb164\|BE494847_T1 | rye | 1329 | Seq368.MAB164.15.barley | 97 |
| 761 | safflower\|gb162\|EL373402_T1 | safflower | 1330 | Seq376.MAB168.15.grape | 81 |
| 762 | safflower\|gb162\|EL374175_T1 | safflower | 1331 | Seq259.MAB39.15.barley | 83 |
| 763 | safflower\|gb162\|EL377332_T1 | safflower | 1332 | Seq385.MAB173.15.barley | 81 |
| 764 | safflower\|gb162\|EL373487_T1 | safflower | 1333 | Seq263.MAB42.15.sorghum | 80 |
| 765 | safflower\|gb162\|EL374095_T1 | safflower | 1334 | Seq256.MAB37.15.tomato | 86 |
| 766 | safflower\|gb162\|EL382051_T1 | safflower | 1335 | Seq256.MAB37.15.tomato | 86 |
| 767 | safflower\|gb162\|EL409148_T1 | safflower | 1336 | Seq385.MAB173.15.barley | 80 |
| 768 | sorghum\|gb161.xeno\|AW224927_T1 | sorghum | 1337 | Seq288.MAB121.15.sugarcane | 94 |
| 769 | sorghum\|gb161.xeno\|T26945_T2 | sorghum | 1338 | Seq370.MAB165.15.grape | 81 |
| 770 | sorghum\|gb161.xeno\|AI932179_T3 | sorghum | 1339 | Seq286.MAB104.15.rice | 91 |
| 771 | sorghum\|gb161.xeno\|T15319_T1 | sorghum | 1340 | Seq276.MAB49.15.maize | 97 |
| 772 | sorghum\|gb161.xeno\|AI615215_T1 | sorghum | 1341 | Seq248.MAB33.15.maize | 92 |
| 773 | sorghum\|gb161.xeno\|BG102066_T2 | sorghum | 1342 | Seq290.MAB122.15.maize | 90 |
| 774 | sorghum\|gb161.xeno\|AW672419_T2 | sorghum | 1343 | Seq276.MAB49.15.maize | 97 |
| 775 | sorghum\|gb161.xeno\|AW672419_T3 | sorghum | 1344 | Seq276.MAB49.15.maize | 95 |
| 776 | sorghum\|gb161.xeno\|AI901860_T1 | sorghum | 1345 | Seq259.MAB39.15.barley | 84 |
| 777 | sorghum\|gb161.xeno\|AI621995_T3 | sorghum | 1346 | Seq384.MAB172.15.sugarcane | 97 |
| 778 | sorghum\|gb161.xeno\|AI881418_T2 | sorghum | 1347 | Seq264.MAB42.10.sorghum | 100 |
| 779 | sorghum\|gb161.xeno\|AI891255_T1 | sorghum | 1348 | Seq311.MAB134.15.barley | 95 |
| 780 | sorghum\|gb161.xeno\|AI782993_T1 | sorghum | 1349 | Seq241.MAB28.15.rice | 84 |
| 781 | sorghum\|gb161.xeno\|AI724629_T1 | sorghum | 1350 | Seq350.MAB154.15.sugarcane | 99 |
| 782 | sorghum\|gb161.xeno\|AA143925_T1 | sorghum | 1351 | Seq221.MAB15.15.sorghum | 100 |
| 783 | sorghum\|gb161.xeno\|AI621995_T2 | sorghum | 1352 | Seq383.MAB172.15.sugarcane | 99 |
| 784 | sorghum\|gb161.xeno\|T26945_T1 | sorghum | 1353 | Seq370.MAB165.15.grape | 81 |
| 785 | sorghum\|gb161.xeno\|AW179463_T1 | sorghum | 1354 | Seq321.MAB139.15.cotton | 80 |
| 786 | sorghum\|gb161.xeno\|ZMU90944_T2 | sorghum | 1355 | Seq367.MAB163.15.barley | 80 |
| 787 | sorghum\|gb161.xeno\|T15319_T2 | sorghum | 1356 | Seq276.MAB49.15.maize | 95 |
| 788 | sorghum\|gb161.xeno\|AI621995_T1 | sorghum | 1357 | Seq383.MAB172.15.sugarcane | 99 |
| 789 | sorghum\|gb161.xeno\|AI932179_T1 | sorghum | 1358 | Seq286.MAB104.15.rice | 90 |
| 790 | sorghum\|gb161.xeno\|AI621995_T4 | sorghum | 1359 | Seq383.MAB172.15.sugarcane | 99 |
| 791 | sorghum\|gb161.xeno\|ZMU90944_T3 | sorghum | 1360 | Seq367.MAB163.15.barley | 80 |
| 792 | sorghum\|gb161.xeno\|AI665229_T2 | sorghum | 1361 | Seq346.MAB153.15.sugarcane | 96 |
| 793 | sorghum\|gb161.xeno\|AI939836_T1 | sorghum | 1362 | Seq309.MAB133.15.barley | 92 |
| 794 | sorghum\|gb161.xeno\|BI099068_T1 | sorghum | 1363 | Seq270.MAB45.15.wheat | 83 |
| 795 | sorghum\|gb161.xeno\|AI665229_T1 | sorghum | 1364 | Seq346.MAB153.15.sugarcane | 96 |
| 796 | sorghum\|gb161.xeno\|AW672419_T1 | sorghum | 1365 | Seq276.MAB49.15.maize | 97 |
| 797 | sorghum\|gb161.xeno\|AW498283_T1 | sorghum | 1366 | Seq210.MAB8.15.rice | 83 |
| 798 | sorghum\|gb161.xeno\|AW923775_T1 | sorghum | 1367 | Seq231.MAB21.15.rice | 88 |
| 799 | sorghum\|gb161.xeno\|T15319_T3 | sorghum | 1368 | Seq276.MAB49.15.maize | 85 |
| 800 | soybean\|gb162\|BG839539_T1 | soybean | 1369 | Seq368.MAB164.15.barley | 80 |
| 801 | soybean\|gb162\|CA783290_T1 | soybean | 1370 | Seq259.MAB39.15.barley | 81 |
| 802 | soybean\|gb162\|BU551043_T1 | soybean | 1371 | Seq256.MAB37.15.tomato | 88 |
| 803 | soybean\|gb162\|EV282184_T1 | soybean | 1372 | Seq371.MAB166.15.poplar | 82 |
| 804 | soybean\|gb162\|BI967468_T1 | soybean | 1373 | Seq368.MAB164.15.barley | 80 |
| 805 | soybean\|gb162\|BI321879_T1 | soybean | 1374 | Seq259.MAB39.15.barley | 81 |
| 806 | soybean\|gb162\|AW132704_T1 | soybean | 1375 | Seq256.MAB37.15.tomato | 90 |
| 807 | soybean\|gb162\|BU764498_T1 | soybean | 1376 | Seq256.MAB37.15.tomato | 86 |
| 808 | soybean\|gb162\|CA953156_T1 | soybean | 1377 | Seq298.MAB126.15.grape | 80 |
| 809 | soybean\|gb162\|CF922618_T1 | soybean | 1378 | Seq259.MAB39.15.barley | 84 |
| 810 | soybean\|gb162\|BU544425_T1 | soybean | 1379 | Seq357.MAB157.15.sugarcane | 81 |
| 811 | soybean\|gb162\|BU765332_T1 | soybean | 1380 | Seq233.MAB22.15.tomato | 80 |
| 812 | soybean\|gb162\|CA936077_T1 | soybean | 1381 | Seq376.MAB168.15.grape | 83 |
| 813 | soybean\|gb162\|BE823013_T1 | soybean | 1382 | Seq376.MAB168.15.grape | 83 |
| 814 | soybean\|gb162\|CD417415_T1 | soybean | 1383 | Seq370.MAB165.15.grape | 85 |
| 815 | soybean\|gb162\|BE660691_T1 | soybean | 1384 | Seq362.MAB161.15.poplar | 81 |
| 816 | soybean\|gb162\|CD395628_T1 | soybean | 1385 | Seq370.MAB165.15.grape | 82 |
| 817 | soybean\|gb162\|BU549206_T2 | soybean | 1386 | Seq259.MAB39.15.barley | 80 |
| 818 | soybean\|gb162\|AW351120_T1 | soybean | 1387 | Seq298.MAB126.15.grape | 82 |
| 819 | soybean\|gb162\|AW132704_T2 | soybean | 1388 | Seq256.MAB37.15.tomato | 90 |
| 820 | soybean\|gb162\|BE584244_T1 | soybean | 1389 | Seq256.MAB37.15.tomato | 91 |
| 821 | spruce\|gb162\|CO234968_T1 | spruce | 1390 | Seq344.MAB152.15.grape | 83 |
| 822 | spurge\|gb161\|DV146052_T1 | spurge | 1391 | Seq357.MAB157.15.sugarcane | 81 |
| 823 | spurge\|gb161\|DV127024_T1 | spurge | 1392 | Seq344.MAB152.15.grape | 83 |
| 824 | spurge\|gb161\|DV124157_T1 | spurge | 1393 | Seq376.MAB168.15.grape | 85 |
| 825 | strawberry\|gb164\|EX683450_T1 | strawberry | 1394 | Seq348.MAB154.15.sugarcane | 81 |
| 826 | strawberry\|gb164\|EX683265_T1 | strawberry | 1395 | Seq370.MAB165.15.grape | 81 |
| 827 | strawberry\|gb164\|DY675409_T1 | strawberry | 1396 | Seq256.MAB37.15.tomato | 81 |
| 828 | sugarcane\|gb157.2\|CA115287_T1 | sugarcane | 1397 | Seq357.MAB157.15.sugarcane | 88 |

TABLE 2-continued

ABST Gene homologs

| Poly-nucleotide SEQ ID NO: | Cluster name | Organism | Poly-peptide SEQ ID NO: | Homolog to a polypeptide encoded by polynucleotide SEQ ID NO. | % Global identity |
|---|---|---|---|---|---|
| 829 | sugarcane\|gb157.2\|CA216001_T1 | sugarcane | 1398 | Seq259.MAB39.15.barley | 85 |
| 830 | sugarcane\|gb157.2\|CA072819_T1 | sugarcane | 1399 | Seq241.MAB28.15.rice | 83 |
| 831 | sugarcane\|gb157.2\|CA125036_T1 | sugarcane | 1400 | Seq291.MAB123.15.barley | 82 |
| 832 | sugarcane\|gb157.2\|CA071646_T1 | sugarcane | 1401 | Seq286.MAB104.15.rice | 90 |
| 833 | sugarcane\|gb157.2\|CA117936_T2 | sugarcane | 1402 | Seq228.MAB19.15.sorghum | 93 |
| 834 | sugarcane\|gb157.2\|BQ537163_T1 | sugarcane | 1403 | Seq276.MAB49.15.maize | 96 |
| 835 | sugarcane\|gb157.2\|CA074253_T1 | sugarcane | 1404 | Seq241.MAB28.15.rice | 83 |
| 836 | sugarcane\|gb157.2\|CA102030_T1 | sugarcane | 1405 | Seq385.MAB173.15.barley | 85 |
| 837 | sugarcane\|gb157.2\|CA068084_T1 | sugarcane | 1406 | Seq366.MAB163.15.barley | 80 |
| 838 | sugarcane\|gb157.2\|CA233048_T1 | sugarcane | 1407 | Seq290.MAB122.15.maize | 80 |
| 839 | sugarcane\|gb157.2\|CA090429_T1 | sugarcane | 1408 | Seq288.MAB121.15.sugarcane | 95 |
| 840 | sugarcane\|gb157.2\|CA095299_T1 | sugarcane | 1409 | Seq370.MAB165.15.grape | 80 |
| 841 | sugarcane\|gb157.2\|BQ533298_T1 | sugarcane | 1410 | Seq311.MAB134.15.barley | 95 |
| 842 | sugarcane\|gb157.2\|CA107649_T1 | sugarcane | 1411 | Seq248.MAB33.15.maize | 90 |
| 843 | sugarcane\|gb157.2\|BQ536274_T1 | sugarcane | 1412 | Seq231.MAB21.15.rice | 88 |
| 844 | sugarcane\|gb157.2\|CA117936_T1 | sugarcane | 1413 | Seq228.MAB19.15.sorghum | 94 |
| 845 | sugarcane\|gb157.2\|BQ533234_T1 | sugarcane | 1414 | Seq221.MAB15.15.sorghum | 99 |
| 846 | sugarcane\|gb157.2\|CA072307_T1 | sugarcane | 1415 | Seq309.MAB133.15.barley | 93 |
| 847 | sugarcane\|gb157.2\|CA073476_T1 | sugarcane | 1416 | Seq290.MAB122.15.maize | 91 |
| 848 | sugarcane\|gb157.2\|CA065809_T1 | sugarcane | 1417 | Seq366.MAB163.15.barley | 80 |
| 849 | sugarcane\|gb157.2\|CA072307_T2 | sugarcane | 1418 | Seq309.MAB133.15.barley | 93 |
| 850 | sunflower\|gb162\|DY909111_T1 | sunflower | 1419 | Seq336.MAB147.15.tobacco | 83 |
| 851 | sunflower\|gb162\|DY941035_T1 | sunflower | 1420 | Seq376.MAB168.15.grape | 82 |
| 852 | sunflower\|gb162\|CD857487_T1 | sunflower | 1421 | Seq370.MAB165.15.grape | 81 |
| 853 | sunflower\|gb162\|DY942252_T1 | sunflower | 1422 | Seq311.MAB134.15.barley | 80 |
| 854 | sunflower\|gb162\|CD850784_T1 | sunflower | 1423 | Seq256.MAB37.15.tomato | 83 |
| 855 | sunflower\|gb162\|BQ968872_T1 | sunflower | 1424 | Seq357.MAB157.15.sugarcane | 83 |
| 856 | sunflower\|gb162\|EE616266_T1 | sunflower | 1425 | Seq256.MAB37.15.tomato | 84 |
| 857 | sunflower\|gb162\|EE641694_T1 | sunflower | 1426 | Seq256.MAB37.15.tomato | 84 |
| 858 | sunflower\|gb162\|DY924220_T1 | sunflower | 1427 | Seq259.MAB39.15.barley | 81 |
| 859 | sunflower\|gb162\|DY910907_T1 | sunflower | 1428 | Seq370.MAB165.15.grape | 80 |
| 860 | sunflower\|gb162\|AY029172_T1 | sunflower | 1429 | Seq321.MAB139.15.cotton | 81 |
| 861 | sunflower\|gb162\|DY909077_T1 | sunflower | 1430 | Seq321.MAB139.15.cotton | 80 |
| 862 | sunflower\|gb162\|DY921635_T1 | sunflower | 1431 | Seq376.MAB168.15.grape | 83 |
| 863 | sunflower\|gb162\|DY913894_T1 | sunflower | 1432 | Seq256.MAB37.15.tomato | 82 |
| 864 | switchgrass\|gb165\|FE608718_T1 | switchgrass | 1433 | Seq370.MAB165.15.grape | 81 |
| 865 | switchgrass\|gb165\|FE624581_T1 | switchgrass | 1434 | Seq333.MAB145.15.barley | 87 |
| 866 | switchgrass\|gb165\|FE604798_T1 | switchgrass | 1435 | Seq269.MAB45.15.wheat | 90 |
| 867 | switchgrass\|gb165\|DN151012_T1 | switchgrass | 1436 | Seq309.MAB133.15.barley | 90 |
| 868 | switchgrass\|gb165\|FE619903_T1 | switchgrass | 1437 | Seq383.MAB172.15.sugarcane | 95 |
| 869 | switchgrass\|gb165\|DN144676_T1 | switchgrass | 1438 | Seq385.MAB173.15.barley | 87 |
| 870 | switchgrass\|gb165\|FE609872_T1 | switchgrass | 1439 | Seq228.MAB19.15.sorghum | 89 |
| 871 | switchgrass\|gb165\|FE617860_T1 | switchgrass | 1440 | Seq381.MAB171.15.sugarcane | 88 |
| 872 | switchgrass\|gb165\|DN145750_T1 | switchgrass | 1441 | Seq221.MAB15.15.sorghum | 95 |
| 873 | switchgrass\|gb165\|FE597811_T1 | switchgrass | 1442 | Seq248.MAB33.15.maize | 83 |
| 874 | switchgrass\|gb165\|FE647199_T1 | switchgrass | 1443 | Seq381.MAB171.15.sugarcane | 90 |
| 875 | switchgrass\|gb165\|DN145034_T1 | switchgrass | 1444 | Seq276.MAB49.15.maize | 95 |
| 876 | switchgrass\|gb165\|FE617335_T1 | switchgrass | 1445 | Seq286.MAB104.15.rice | 91 |
| 877 | switchgrass\|gb165\|FE597809_T1 | switchgrass | 1446 | Seq350.MAB154.15.sugarcane | 95 |
| 878 | switchgrass\|gb165\|FE597811_T2 | switchgrass | 1447 | Seq248.MAB33.15.maize | 85 |
| 879 | switchgrass\|gb165\|FE635691_T1 | switchgrass | 1448 | Seq311.MAB134.15.barley | 95 |
| 880 | switchgrass\|gb165\|FE653022_T1 | switchgrass | 1449 | Seq385.MAB173.15.barley | 83 |
| 881 | switchgrass\|gb165\|DN144793_T1 | switchgrass | 1450 | Seq259.MAB39.15.barley | 90 |
| 882 | switchgrass\|gb165\|FE641674_T1 | switchgrass | 1451 | Seq309.MAB133.15.barley | 89 |
| 883 | thellungiella\|gb157.2\|DN775606_T1 | thellungiella | 1452 | Seq212.MAB10.15.arabidopsis | 82 |
| 884 | thellungiella\|gb157.2\|DN773228_T1 | thellungiella | 1453 | Seq211.MAB9.15.arabidopsis | 98 |
| 885 | thellungiella\|gb157.2\|DN772771_T1 | thellungiella | 1454 | Seq208.MAB7.15.arabidopsis | 89 |
| 886 | thellungiella\|gb157.2\|DN774422_T1 | thellungiella | 1455 | Seq360.MAB159.15.canola | 83 |
| 887 | thellungiella\|gb157.2\|DN774140_T1 | thellungiella | 1456 | Seq284.MAB100.15.arabidopsis | 86 |
| 888 | tobacco\|gb162\|DW003503_T1 | tobacco | 1457 | Seq329.MAB143.15.tomato | 93 |
| 889 | tobacco\|gb162\|BP532373_T1 | tobacco | 1458 | Seq357.MAB157.15.sugarcane | 82 |
| 890 | tobacco\|gb162\|CN949739_T1 | tobacco | 1459 | Seq370.MAB165.15.grape | 84 |
| 891 | tobacco\|gb162\|BQ843111_T1 | tobacco | 1460 | Seq319.MAB138.15.potato | 90 |
| 892 | tobacco\|gb162\|EB683054_T1 | tobacco | 1461 | Seq307.MAB131.15.tomato | 89 |
| 893 | tobacco\|gb162\|EB428197_T1 | tobacco | 1462 | Seq222.MAB16.15.rice | 80 |
| 894 | tobacco\|gb162\|EB445060_T1 | tobacco | 1463 | Seq283.MAB99.15.tomato | 90 |
| 895 | tobacco\|gb162\|EB447202_T1 | tobacco | 1464 | Seq390.MAB175.15.tomato | 88 |
| 896 | tobacco\|gb162\|DW001113_T1 | tobacco | 1465 | Seq256.MAB37.15.tomato | 88 |
| 897 | tobacco\|gb162\|EH623692_T1 | tobacco | 1466 | Seq303.MAB129.15.tomato | 85 |
| 898 | tomato\|gb164\|BG127210_T1 | tomato | 1467 | Seq342.MAB151.15.potato | 82 |
| 899 | tomato\|gb164\|BG128089_T2 | tomato | 1468 | Seq222.MAB16.15.rice | 80 |
| 900 | tomato\|gb164\|AW219181_T1 | tomato | 1469 | Seq256.MAB37.15.tomato | 90 |
| 901 | tomato\|gb164\|BG127288_T1 | tomato | 1470 | Seq370.MAB165.15.grape | 83 |

TABLE 2-continued

ABST Gene homologs

| Poly-nucleotide SEQ ID NO: | Cluster name | Organism | Poly-peptide SEQ ID NO: | Homolog to a polypeptide encoded by polynucleotide SEQ ID NO. | % Global identity |
|---|---|---|---|---|---|
| 902 | tomato\|gb164\|BG133509_T1 | tomato | 1471 | Seq256.MAB37.15.tomato | 88 |
| 903 | tomato\|gb164\|BG131241_T1 | tomato | 1472 | Seq309.MAB133.15.barley | 80 |
| 904 | tomato\|gb164\|BG129621_T1 | tomato | 1473 | Seq350.MAB154.15.sugarcane | 80 |
| 905 | tomato\|gb164\|AI779004_T1 | tomato | 1474 | Seq309.MAB133.15.barley | 81 |
| 906 | tomato\|gb164\|BG129572_T1 | tomato | 1475 | Seq321.MAB139.15.cotton | 80 |
| 907 | tomato\|gb164\|BG135408_T1 | tomato | 1476 | Seq319.MAB138.15.potato | 98 |
| 908 | triphysaria\|gb164\|DR173028_T1 | triphysaria | 1477 | Seq329.MAB143.15.tomato | 81 |
| 909 | triphysaria\|gb164\|BM357524_T2 | triphysaria | 1478 | Seq283.MAB99.15.tomato | 85 |
| 910 | triphysaria\|gb164\|EY133838_T1 | triphysaria | 1479 | Seq311.MAB134.15.barley | 80 |
| 911 | triphysaria\|gb164\|BM357406_T1 | triphysaria | 1480 | Seq329.MAB143.15.tomato | 83 |
| 912 | triphysaria\|gb164\|BM357011_T1 | triphysaria | 1481 | Seq259.MAB39.15.barley | 80 |
| 913 | triphysaria\|gb164\|BM357524_T1 | triphysaria | 1482 | Seq376.MAB168.15.grape | 85 |
| 914 | triphysaria\|gb164\|EY137290_T1 | triphysaria | 1483 | Seq256.MAB37.15.tomato | 88 |
| 915 | wheat\|gb164\|CA484259_T1 | wheat | 1484 | Seq241.MAB28.15.rice | 84 |
| 916 | wheat\|gb164\|BE606422_T1 | wheat | 1485 | Seq379.MAB170.15.barley | 96 |
| 917 | wheat\|gb164\|BE406378_T1 | wheat | 1486 | Seq219.MAB14.15.rice | 80 |
| 918 | wheat\|gb164\|BE470780_T1 | wheat | 1487 | Seq221.MAB15.15.sorghum | 84 |
| 919 | wheat\|gb164\|BE418087_T1 | wheat | 1488 | Seq325.MAB141.15.barley | 95 |
| 920 | wheat\|gb164\|BQ294643_T1 | wheat | 1489 | Seq269.MAB45.15.wheat | 94 |
| 921 | wheat\|gb164\|BE415314_T1 | wheat | 1490 | Seq250.MAB34.15.barley | 82 |
| 922 | wheat\|gb164\|AL822647_T1 | wheat | 1491 | Seq259.MAB39.15.barley | 98 |
| 923 | wheat\|gb164\|BE406667_T1 | wheat | 1492 | Seq250.MAB34.15.barley | 89 |
| 924 | wheat\|gb164\|BF475039_T1 | wheat | 1493 | Seq221.MAB15.15.sorghum | 83 |
| 925 | wheat\|gb164\|CK196180_T1 | wheat | 1494 | Seq323.MAB140.15.barley | 80 |
| 926 | wheat\|gb164\|BE403745_T1 | wheat | 1495 | Seq379.MAB170.15.barley | 97 |
| 927 | wheat\|gb164\|BQ620260_T1 | wheat | 1496 | Seq311.MAB134.15.barley | 100 |
| 928 | wheat\|gb164\|BM138204_T1 | wheat | 1497 | Seq333.MAB145.15.barley | 91 |
| 929 | wheat\|gb164\|BE401114_T1 | wheat | 1498 | Seq291.MAB123.15.barley | 94 |
| 930 | wheat\|gb164\|BE498161_T1 | wheat | 1499 | Seq388.MAB174.15.barley | 93 |
| 931 | wheat\|gb164\|BQ744502_T1 | wheat | 1500 | Seq250.MAB34.15.barley | 85 |
| 932 | wheat\|gb164\|BE415172_T1 | wheat | 1501 | Seq366.MAB163.15.barley | 94 |
| 933 | wheat\|gb164\|CD490875_T1 | wheat | 1502 | Seq276.MAB49.15.maize | 97 |
| 934 | wheat\|gb164\|CA625741_T1 | wheat | 1503 | Seq309.MAB133.15.barley | 87 |
| 935 | wheat\|gb164\|BE443720_T1 | wheat | 1504 | Seq318.MAB137.15.barley | 94 |
| 936 | wheat\|gb164\|BE420294_T1 | wheat | 1505 | Seq290.MAB122.15.maize | 84 |
| 937 | wheat\|gb164\|BE516581_T1 | wheat | 1506 | Seq387.MAB174.15.barley | 95 |
| 938 | wheat\|gb164\|BE406039_T1 | wheat | 1507 | Seq333.MAB145.15.barley | 90 |
| 939 | wheat\|gb164\|BM136483_T1 | wheat | 1508 | Seq333.MAB145.15.barley | 92 |
| 940 | wheat\|gb164\|BE425976_T1 | wheat | 1509 | Seq250.MAB34.15.barley | 81 |
| 941 | wheat\|gb164\|CN011148_T1 | wheat | 1510 | Seq270.MAB45.15.wheat | 84 |
| 942 | wheat\|gb164\|BE419039_T1 | wheat | 1511 | Seq250.MAB34.15.barley | 80 |
| 943 | wheat\|gb164\|CA603413_T1 | wheat | 1512 | Seq323.MAB140.15.barley | 85 |
| 944 | wheat\|gb164\|CA743309_T1 | wheat | 1513 | Seq321.MAB139.15.cotton | 80 |
| 945 | wheat\|gb164\|BG262336_T1 | wheat | 1514 | Seq366.MAB163.15.barley | 94 |
| 946 | wheat\|gb164\|CD881765_T1 | wheat | 1515 | Seq219.MAB14.15.rice | 80 |
| 947 | wheat\|gb164\|BE352629_T1 | wheat | 1516 | Seq291.MAB123.15.barley | 96 |
| 948 | wheat\|gb164\|BE398656_T1 | wheat | 1517 | Seq308.MAB132.15.barley | 97 |
| 949 | wheat\|gb164\|BE403195_T1 | wheat | 1518 | Seq291.MAB123.15.barley | 94 |
| 950 | wheat\|gb164\|BE488904_T1 | wheat | 1519 | Seq367.MAB163.15.barley | 91 |
| 951 | wheat\|gb164\|BE492528_T1 | wheat | 1520 | Seq311.MAB134.15.barley | 100 |
| 952 | wheat\|gb164\|BE427383_T1 | wheat | 1521 | Seq219.MAB14.15.rice | 80 |
| 953 | wheat\|gb164\|CA646957_T1 | wheat | 1522 | Seq250.MAB34.15.barley | 89 |
| 954 | wheat\|gb164\|BE443720_T2 | wheat | 1523 | Seq318.MAB137.15.barley | 92 |
| 955 | wheat\|gb164\|BE490408_T1 | wheat | 1524 | Seq264.MAB42.10.sorghum | 81 |
| 956 | wheat\|gb164\|BE420295_T1 | wheat | 1525 | Seq379.MAB170.15.barley | 96 |
| 957 | wheat\|gb164\|AL825998_T1 | wheat | 1526 | Seq308.MAB132.15.barley | 97 |
| 958 | wheat\|gb164\|CA693465_T1 | wheat | 1527 | Seq308.MAB132.15.barley | 97 |
| 959 | wheat\|gb164\|BE585772_T1 | wheat | 1528 | Seq366.MAB163.15.barley | 95 |
| 960 | wheat\|gb164\|CA613914_T1 | wheat | 1529 | Seq356.MAB157.15.sugarcane | 84 |
| 1656 | >tomato\|gb164\|BG129621_T1 | tomato | 1660 | Seq1649.MAB66.tomato | 82 |
| 1657 | potato\|gb157.2\|BE921143_T1 | potato | 1661 | Seq1649.MAB66.tomato | 82 |
| 1658 | pepper\|gb157.2\|BM061807_T1 | pepper | 1662 | Seq1649.MAB66.tomato | 80 |
| 1659 | >triphysaria\|gb164\|BM357011_T1 | triphysaria | 1663 | Seq1649.MAB66.tomato | 80 |

Table 2: *- Homology was calculated as % of identity over the aligned sequences. The query sequences were polynucleotide sequences SEQ ID NOs: 1, 3, 5, 7, 9, 10, 11, 13, 15, 16, 17, 19, 21, 23, 25, 26, 28, 29, 30, 32, 34, 36, 37, 38, 40, 42, 44, 46, 48, 50, 52, 54, 55, 57, 59, 61, 63, 65, 67, 69, 71, 73, 75, 77, 79, 81, 82, 84, 86, 88, 90, 91, 93, 94, 96, 98, 100, 101, 103, 105, 107, 109, 111, 113, 115, 116, 118, 119, 121, 122, 124, 126, 128, 130, 132, 134, 135, 138, 140, 142, 143, 145, 147, 149, 151, 153, 155, 157, 161, 163, 165, 168, 169, 170, 171, 173, 175, 177, 179, 180, 182, 184, 186, 188, 190, 192, 194, 196, 198 and 1649, and the subject sequences are protein sequences identified in the database based on greater than 80 % identity to the predicted translated sequences of the query nucleotide sequences. Shown are the homologous polypeptides and the polynucleotides encoding same.

Example 2

Generating the Putative ABST Genes

Several DNA sequences of the ABST genes are synthesized by GeneArt (Hypertext Transfer Protocol://World Wide Web (dot) geneart (dot) com/). Synthetic DNA is designed in silico, based on the encoded amino-acid sequences of the ABST genes and using codon-usage Tables calculated from plant transcriptomes (example of such Tables can be found in the Codon Usage Database available online at Hypertext Transfer Protocol://World Wide Web (dot) kazusa (dot) or (dot) jp/codon/). The optimized coding sequences are designed in a way that no changes are introduced in the encoded amino acid sequence while using codons preferred for expression in dicotyledonous plants (mainly tomato and *Arabidopsis*) and monocotyledonous plants such as maize. At least one silent mutation per 20 nucleotide base pairs is introduced in the sequence compared to the original sequences to avoid possible silencing when over-expressing the gene in the target crop. To the optimized sequences the following restriction enzymes sites are added—SalI, XbaI, BamHI, SmaI at the 5' end and SacI at the 3' end. The sequences synthesized by the supplier (GeneArt, Gmbh) are cloned in the pCR-Script plasmid.

Example 3

Gene Cloning and Generation of Binary Vectors for Plant Expression

To validate their role in improving ABST and yield, selected genes were overexpressed in plants, as follows.
Cloning Strategy
Selected genes from those presented in Example 1 were cloned into binary vectors for the generation of transgenic plants. For cloning, the full-length open reading frames (ORFs) were identified. EST clusters and in some cases mRNA sequences were analyzed to identify the entire open reading frame by comparing the results of several translation algorithms to known proteins from other plant species.

In order to clone the full-length cDNAs, reverse transcription (RT) followed by polymerase chain reaction (PCR; RT-PCR) was performed on total RNA extracted from leaves, roots or other plant tissues, growing under either normal or nutrient deficient conditions. Total RNA extraction, production of cDNA and PCR amplification was performed using standard protocols described elsewhere (Sambrook J., E. F. Fritsch, and T. Maniatis. 1989. Molecular Cloning. A Laboratory Manual., 2nd Ed. Cold Spring Harbor Laboratory Press, New York.) which are well known to those skilled in the art. PCR products were purified using PCR purification kit (Qiagen)

Usually, 2 sets of primers were prepared for the amplification of each gene, via nested PCR (meaning first amplifying the gene using external primers and then using the produced PCR product as a template for a second PCR reaction, where the internal set of primers are used). Alternatively, one or two of the internal primers were used for gene amplification, both in the first and the second PCR reactions (meaning only 2-3 primers were designed for a gene). To facilitate further cloning of the cDNAs, an 8-12 bp extension is added to the 5' of each internal primer. The primer extension includes an endonuclease restriction site. The restriction sites are selected using two parameters: (a) the restriction site does not exist in the cDNA sequence; and (b) the restriction sites in the forward and reverse primers are designed such that the digested cDNA is inserted in the sense direction into the binary vector utilized for transformation. In Table 3 below, primers used for cloning ABST genes are provided.

TABLE 3

Cloned ABST genes from cDNA libraries or genomic DNA and the primers used for the cloning

| Gene Id | Polynucleotide SEQ ID NO. of the cloned gene | Polypeptide SEQ ID NO. of the encoded polypeptide | Restriction Enzymes used for cloning | Primers used for amplification (SEQ ID NO:) |
|---|---|---|---|---|
| MAB1 | 1530 | 201 | EcoRV | MAB1_EF_EcoRV AAGATATCAGACCAGAGGAGAAGACTCGATC (SEQ ID NO: 1567) MAB1_NF_EcoRV AAGATATCAGACTCCGTTCGGAGAAAAGG (SEQ ID NO: 1568) MAB1_ER_EcoRV ATGATATCTGAAGAACATCGCCTTGTCATC (SEQ ID NO: 1569) MAB1_NR_EcoRV AAGATATCACCTTGTCATCGGATCATCTCC (SEQ ID NO: 1570) |
| MAB1_GA (optimized for expression in Maize and G. Max) | 1531 | | | Synthetic product (from pGA14_MAB1_GA) |
| MAB14 | 1538 | 219 | EcoRV | MAB14_EF_EcoRV ATGATATCCAACGAATGAAGACTAGTAGCTG (SEQ ID NO: 1571) MAB14_NF_EcoRV ATGATATCCCAGATGGAATCCTGCCCT (SEQ ID NO: 1572) |

TABLE 3-continued

Cloned ABST genes from cDNA libraries or genomic
DNA and the primers used for the cloning

| Gene Id | Polynucleotide SEQ ID NO. of the cloned gene | Polypeptide SEQ ID NO. of the encoded polypeptide | Restriction Enzymes used for cloning | Primers used for amplification (SEQ ID NO:) |
|---|---|---|---|---|
| | | | | MAB14_ER_EcoRV ATGATATCGTGTCAATGAAGGGAACGTGC (SEQ ID NO: 1573) MAB14_NR_EcoRV ATGATATCGCAAATGGATTCAGATATTCTG (SEQ ID NO: 1574) |
| MAB14_GA (optimized for expression in Maize) | 1539 | | | Synthetic product (from pGA14_MAB14_GA) |
| MAB10 | 1532 | 212 | SalI, XbaI | MAB 10 F Sal- GCAGTCGACAACTCACAGTTCCAAACACACA (SEQ ID NO: 1575) MAB 10 R Xba- GGTCTAGAATGTAAATGTCTTCGTATTAGGC (SEQ ID NO: 1576) MAB 10 NR Xba- CCTCTAGAATCACCCGAAATAACTAGTGTC (SEQ ID NO: 1577) |
| MAB10_GA (optimized for expression in Maize) | 1533 | | | Synthetic product (from pGA18_MAB10_GA) |
| MAB25 | 1549 | 237 | PstI, SmaI | MAB_25_EF_PstI- AACTGCAGCCATCGTCGTAATCCTTCTAGC (SEQ ID NO: 1578) MAB25_NF_PstI- AACTGCAGTAATCATGGGGAGGAAATCTC (SEQ ID NO: 1579) MAB25_ER_SmaI- GGGTGACAATTCCGAGTCTCAGC (SEQ ID NO: 1580) MAB25_NR_SmaI- TCCCGGGCAATTGGTCAATGGCACTC (SEQ ID NO: 1581) |
| MAB25_GA (optimized for expression in Maize) | 1550 | | | Synthetic product (from pGA14_MAB25_GA) |
| MAB134 | 1665 | 311 | SalI, XbaI | MAB134_EF_SalI- AATGTCGACTCTCGTCTCTTGCTCCCAGAG (SEQ ID NO: 1582) MAB134_NF_SalI- AATGTCGACCGACACCCTTCTCCTCCTC (SEQ ID NO: 1583) MAB134_ER_XbaI- TTTCTAGATCATATTCCAACATCCACTTC (SEQ ID NO: 1584) MAB134_NR_XbaI- TTTCTAGACTGCTATGTTCCACTGACTACAC (SEQ ID NO: 1585) |
| MAB99 | 1566 | 283 | SalI, SacI | MAB99_NF_SalI- AAAGTCGACCAGTTAATTCTCCGTTGTCTACTC (SEQ ID NO: 1586) MAB99_NR_SacI- TGAGCTCCTGCTTGAAACTTGCTGCTAG (SEQ ID NO: 1587) |
| MAB36 | 1554 | 254 | SalI, XbaI | MAB 36 F Sal- GGAGTCGACACAGAAATGGGTGGTTTGAAG (SEQ ID NO: 1588) MAB 36 Ext R Xba- |

TABLE 3-continued

Cloned ABST genes from cDNA libraries or genomic
DNA and the primers used for the cloning

| Gene Id | Polynucleotide SEQ ID NO. of the cloned gene | Polypeptide SEQ ID NO. of the encoded polypeptide | Restriction Enzymes used for cloning | Primers used for amplification (SEQ ID NO:) |
|---|---|---|---|---|
| | | | | CCTCTAGAAATGATCACTCACTGCAACTTAG (SEQ ID NO: 1589) MAB 36 NR Xba- CCTCTAGACACTCACTGCAACTTAGAAACATC (SEQ ID NO: 1590) |
| MAB7 | 1563 | 208 | SalI, XbaI | MAB 7 Ex F Sal- AACGTCGACGCTCATTTCTCTTCTTCTTTGG (SEQ ID NO: 1591) MAB 7 NF Sal- GACGTCGACTCTTCTTTGGTTCTTACATTTCTC (SEQ ID NO: 1592) MAB 7 Ex R Xba- TCTCTAGAGCAAGACGTTATAAACCATGC (SEQ ID NO: 1593) MAB 7 NR Xba- TCTCTAGAAGAAGACACGCTGGACAATG (SEQ ID NO: 1594) |
| MAB44 | 1557 | 267 | SalI, SacI | MAB 44 NF sal AAGGTCGACCATAAAGAACAGTGACAGGCG (SEQ ID NO: 1595) MAB 44 NR Sc AGAGCTCCACGTAGTACATTTTCACAGCAC (SEQ ID NO: 1596) |
| MAB44_GA (optimized for expression in Maize) | 1558 | | | Synthetic product (from pCR4Blunt-TOPO_MAB44_GA) |
| MAB6 | 1561 | 207 | SalI, XbaI | MAB 6-Ex F Sal- ACCGTCGACCCTTCTCCAATTTCGTAAGC (SEQ ID NO: 1597) MAB 6 NF Sal- ACCGTCGACTTCGTAAGCTCAAAGATTTCG (SEQ ID NO: 1598) MAB 6-Ext R XbaI- CCTCTAGAACGACTTTTAATCCCTCCAAC (SEQ ID NO: 1599) MAB 6-NR XbaI- CCTCTAGACTCCAACAGCCACTACAACC (SEQ ID NO: 1600) |
| MAB6_GA (optimized for expression in Maize) | 1562 | | | Synthetic product (from pGA15_MAB6_GA) |
| MAB9 | 1564 | 211 | EcoRV | MAB9_F_EcoRV AAGATATCGGTTGCTGAGGAATCGAAGTAG (SEQ ID NO: 1601) MAB9_ER_EcoRV TTGATATCGAGCCAAGTCACAAGGAGTTTAC (SEQ ID NO: 1602) MAB9_NR_EcoRV TTGATATCCTCCGAGTGTCGCAGTAAGC (SEQ ID NO: 1603) |
| MAB9_GA (optimized for expression in Maize and G. Max) | 1565 | | | Synthetic product (from pGA15_MAB9_GA) |
| MAB100 | 1534 | 284 | SalI, XbaI | MAB100_EF_SalI- AATGTCGACCCAAGTTAAACTTCATATCATAAC (SEQ ID NO: 1604) MAB100_NF_SalI- |

TABLE 3-continued

Cloned ABST genes from cDNA libraries or genomic
DNA and the primers used for the cloning

| Gene Id | Polynucleotide SEQ ID NO. of the cloned gene | Polypeptide SEQ ID NO. of the encoded polypeptide | Restriction Enzymes used for cloning | Primers used for amplification (SEQ ID NO:) |
|---|---|---|---|---|
| | | | | AATGTCGACGAAGAGTTATTATGGCGAGCT (SEQ ID NO: 1605) MAB100_ER_XbaI- AATGTCGACCCAAGTTAAACTTCATATCATACAC (SEQ ID NO: 1606) MAB100_NR_XbaI- AATCTAGACAAACCCAACTTATTACATTACG (SEQ ID NO: 1607) |
| MAB13 | 1536 | 217 | SacI, SalI | MAB13_F_SalI-new AATGTCGACCTCGAAAATGGCCACCATTAG (SEQ ID NO: 1608) MAB 13 ExR Sc CGAGCTCCAAAAATGCAAGAATCAAGAG (SEQ ID NO: 1609) MAB 13 F Sal AAGGTCGACTTCTCTCCAAAATGGCCAC (SEQ ID NO: 1610) MAB 13 NR Sc TGAGCTCTGCAAGAATCAAGAGAAATTTG (SEQ ID NO: 1611) |
| MAB32 | 1552 | 247 | EcoRV | MAB32_F_EcoRV- AAGATATCCTCCACTTGTTGTTCAATTCCC (SEQ ID NO: 1612) MAB32_ER_EcoRV- ATGATATCGATCTGAACAGCAGTAAGTAAGCC (SEQ ID NO: 1613) MAB32_NR_EcoRV- ATGATATCTAAGAAGAACAAGACATGGATCG (SEQ ID NO: 1614) |
| MAB35 | 1553 | 252 | SmaI | MAB35_F- CGTGAGAACTAAGAAACACCC (SEQ ID NO: 1615) MAB35_ER_SmaI- TCCCGGGACATCTTTTCAACTAAACCAAGAC (SEQ ID NO: 1616) MAB35_NR_SmaI- TCCCGGGCTAAACCAAGACTTACACAAGACG (SEQ ID NO: 1617) |
| MAB146 | 1666 | 334 | SalI, XbaI | MAB146_F_Sal- ATTGTCGACAGAGTTATGGGAGATAATAGAGGA (SEQ ID NO: 1618) MAB146_ER_Xba- ATTCTAGACTCATTCTGAGCTTTACATGTTC (SEQ ID NO: 1619) MAB146_NR_Xba- TTTCTAGATTGGTTTACACCTCAACTCACTAC (SEQ ID NO: 1620) |
| MAB2 | 1547 | Non coding | SalI, XbaI | MAB2_F_SalI AATGTCGACAACAAATGATCCTTCAGGCAGTTAAAG (SEQ ID NO: 1621) MAB2_R_Xba TTTCTAGATATTAAAACTTAGATTCGGGATCAG (SEQ ID NO: 1622) |
| MAB20 | 1548 | 229 | PstI, SmaI | MAB20_EF_PstI- AACTGCAGGATCATCACTTCTCGAGATTTCG (SEQ ID NO: 1623) MAB20_NF_PstI- AACTGCAGAAAAATGAATTCAGAATCGCTAG (SEQ ID NO: 1624) MAB20_ER_SmaI- AACTGCAGGATCATCACTTCTAGATTTCG (SEQ ID NO: 1625) MAB20_NR_SmaI- TCCCGGGCAATCTGACCTCAAAACTCCC (SEQ ID NO: 1626) |

TABLE 3-continued

Cloned ABST genes from cDNA libraries or genomic DNA and the primers used for the cloning

| Gene Id | Polynucleotide SEQ ID NO. of the cloned gene | Polypeptide SEQ ID NO. of the encoded polypeptide | Restriction Enzymes used for cloning | Primers used for amplification (SEQ ID NO:) |
|---|---|---|---|---|
| MAB43 | 1556 | 265 | PstI, SmaI | MAB43_NF_PstI AACTGCAGGATCAATGAAGATTCGGAACAG (SEQ ID NO: 1627) MAB43_ER_SmaI TCCCGGGTACAACAAGAAACCTCTGATTC (SEQ ID NO: 1628) MAB43_NR_SmaI TCCCGGGCCTGTGCCACAGCTATACTTAC (SEQ ID NO: 1629) |
| MAB46 | 1559 | 271 | SalI, SacI | MAB 46 ExF Sal- GAAGTCGACATCCGTAGTTTCAGTTTCGTCC (SEQ ID NO: 1630) MAB 46 NF Sal- GAAGTCGACCTTGTCTGTTCCAGATGAAATTG (SEQ ID NO: 1631) MAB46 ExR Sc- TGAGCTCCTCTATCGACGTCCGGATTC (SEQ ID NO: 1632) MAB 46 NR Sc- TGAGCTCCGTCCGGATTCATAAACAAC (SEQ ID NO: 1633) |
| MAB50 | 1560 | 277 | SmaI | MAB 50 ExF Sal GGAGTCGACCATCGGGACACATCTTTAGG (SEQ ID NO: 1634) MAB50_NF CATCTTTAGGCTCAAGGATTC (SEQ ID NO: 1635) MAB50_ExR_Sac TGAGCTCGATCCTCGTTTATTACAAGTCTG (SEQ ID NO: 1636) MAB50_NR_Sma TCCCGGGCACACCAAGATTGATTACAAAGAG (SEQ ID NO: 1637) |
| MAB66 | 1654 | 1655 | SalI, XbaI | MAB66_F_Sal- AATGTCGACGATTGGAGATAGGCAGGCA (SEQ ID NO: 1638) MAB66_ER_Xba- TTTCTAGAGGTAGCCAAAGCTGACACTC (SEQ ID NO: 1639) MAB66_NR_Xba- AATCTAGAGAGGCATATGCACTTCTTATCG (SEQ ID NO: 1640) |
| MAB4 | 1555 | 205 | EcoRV | MAB4_EF_EcoRV- AAGATATCCAGGACGGGTTCTCGATCAG (SEQ ID NO: 1641) MAB4_NF_EcoRV- AAGATATCCAGCGAACACGTCTACGATG (SEQ ID NO: 1642) MAB4_ER_EcoRV- ATGATATCGCACGAGTTCAACTCAGCTG (SEQ ID NO: 1643) MAB4_NR_EcoRV- ATGATATCGAACTGCTTGAGATGTAACAGCT (SEQ ID NO: 1644) |
| MAB15_GA (optimized for expression in Arabidopsis and maize) | 1541 | 221 | XbaI, SacI | Synthetic product (from pGA4_MAB15) |
| MAB15a_GA (optimized for expression in Maize) | 1667 | | | Synthetic product (from pGA18_MAB15a_GA) |

TABLE 3-continued

Cloned ABST genes from cDNA libraries or genomic DNA and the primers used for the cloning

| Gene Id | Polynucleotide SEQ ID NO. of the cloned gene | Polypeptide SEQ ID NO. of the encoded polypeptide | Restriction Enzymes used for cloning | Primers used for amplification (SEQ ID NO:) |
|---|---|---|---|---|
| MAB15_GA_original (original sequence, not optimize) | 1540 | | | Synthetic product (from pGA14_MAB15_(EVO220)-original) |
| MAB17_GA (optimized for expression in *Arabidopsis* and maize) | 1542 | 224 | XbaI, SacI | Synthetic product (from pGA4_MAB17) |
| MAB17a_GA (optimized for expression in Maize) | 1544 | | | Synthetic product (from pCR4Blunt-TOPO_MAB17a_GA) |
| MAB17_GA_original (original sequence, not optimize) | 1543 | | | Synthetic product (from pGA14_MAB17_(EVO222)-original) |
| MAB137_GA (optimized for expression in Maize, *Arabidopsis* and tomato) | 1537 | 317 | XbaI, SacI | Synthetic product (from pGA15_MAB137) |
| MAB3_GA (optimized for expression in Maize, *Arabidopsis* and tomato) | 1551 | 293 | XbaI, SacI | Synthetic product (from pCR4Blunt-Topo_MAB3) |
| MAB3_GA_original (original sequence, not optimize) | 1668 | | | Synthetic product (from pGA14_MAB3_(EVO235)-original) |
| MAB18_GA (optimized for expression in *Arabidopsis* and maize) | 1545 | 225 | XbaI, SacI | Synthetic product (from pGA4_MAB18) |
| Control Gene: GUI | 1664 | | | |

Table 3.
Presented are the cloned ABST genes and control gene(s) by the Gene Id number and the polynucleotide SEQ ID NO. Also presented are the primers and the restriction enzymes used to clone the ABST genes.

PCR products were digested with the restriction endonucleases (Roche, Switzerland) according to the sites design in the primers (Table 3). Each digested PCR product was inserted into a high copy vector originated from pBlue-script KS plasmid vector (pBlue-script KS plasmid vector, Hypertext Transfer Protocol://World Wide Web (dot) stratagene (dot) com/manuals/212205 (dot) pdf). In case of the high copy vector originated from pBlue-script KS plasmid vector (pGN) PCR product was inserted in the high copy plasmid upstream to the NOS terminator (SEQ ID NO:1651) originated from pBI 101.3 binary vector (GenBank Accession No. U12640, nucleotides 4417 to 4693), Table 4 below. In other cases (pKSJ_6669a) the At6669 promoter (SEQ ID NO: 1652) is already cloned into the pBlue-script KS, so the gene is introduced downstream of the promoter (Table 4 below).

Sequencing of the inserted genes was performed, using the ABI 377 sequencer (Applied Biosystems). In some cases, after confirming the sequences of the cloned genes, the cloned cDNA accompanied with the NOS terminator was introduced into the binary vectors pGI containing the At6669 promoter via digestion with appropriate restriction endonucleases. In other cases the cloned cDNA accompanied with the At6669 promoter was introduced into the pGI vector (that hasn't already contained the At6669 promoter). In any case the insert was followed by single copy of the NOS terminator (SEQ ID NO:1651). The digested products and the linearized plasmid vector were ligated using T4 DNA ligase enzyme (Roche, Switzerland).

TABLE 4

Genes cloned from cDNA libraries or genomic DNA in a High copy plasmid

| Gene Name | High copy Plasmid | Amplified from |
|---|---|---|
| MAB1 | pKSJ_6669 | RNA |
| MAB1 | | Gene Art |
| MAB10 | | Gene Art |
| MAB10 | pGN | RNA |
| MAB14 | pKSJ_6669 | RNA |
| MAB14 | | Gene Art |
| MAB15 | pGN | Gene Art (3 plasmids) |
| MAB17 | pGN | Gene Art (3 plasmids) |
| MAB 137 | pGN | Gene Art |
| MAB25 | pKSJ_6669 | RNA |
| MAB25 | | Gene Art |
| MAB3 | pGN | Gene Art (2 plasmids) |
| MAB44 | pGN | RNA |
| MAB44 | | Gene Art |
| MAB6 | pGN | RNA |
| MAB6 | | Gene Art |
| MAB9 | pKSJ_6669 | RNA |
| MAB9 | | Gene Art |
| MAB100 | pGN | RNA |
| MAB13 | pGN | RNA |
| MAB134 | pGN | RNA |
| MAB18 | pGN | Gene Art |
| MAB2 | pGN | RNA |
| MAB20 | pKSJ_6669 | RNA |
| MAB146 | pGN | RNA |
| MAB32 | pKSJ_6669 | RNA |
| MAB35 | pKSJ_6669 | RNA |
| MAB36 | pGN | RNA |
| MAB43 | pKSJ_6669 | RNA |
| MAB46 | pGN | RNA |
| MAB50 | pKSJ_6669 | RNA |
| MAB7 | pGN | RNA |
| MAB99 | pGN | RNA |
| MAB66 | pGN | RNA |
| MAB4 | pKSJ_6669 | RNA |

The pPI plasmid vector was constructed by inserting a synthetic poly-(A) signal sequence, originating from pGL3 basic plasmid vector (Promega, GenBank Accession No. U47295; nucleotides 4658-4811) into the HindIII restriction site of the binary vector pBI101.3 (Clontech, GenBank Accession No. U12640). pGI (FIG. 1) is similar to pPI, but the original gene in the back bone is GUS-Intron, rather than GUS.

At6669, the *Arabidopsis thaliana* promoter sequence (set forth in SEQ ID NO: 1652) is inserted in the pPI binary vector, upstream to the cloned genes by using the restriction enzymes HindIII and SalI or BamHI (Roche), following by DNA ligation and binary plasmid extraction from positive *E. coli* colonies, as described above.

Positive colonies were identified by PCR using primers which were designed to span the introduced promoter (At6669) and the cloned gene in the binary vector. In all cases the forward PCR primer was the primer set forth in SEQ ID NO:1650 (from the At6669 promoter) and the reverse primer (derived from the specific cloned gene) was as follows: For MAB1, the reverse primer was SEQ ID NO:1570; for MAB14, the reverse primer was SEQ ID NO:1574; for MAB10, the reverse primer was SEQ ID NO:1577; for MAB25, the reverse primer was SEQ ID NO:1581; for MAB134, the reverse primer was SEQ ID NO:1585; for MAB99, the reverse primer was SEQ ID NO:1587; for MAB36, the reverse primer was SEQ ID NO:1590; for MAB7, the reverse primer was SEQ ID NO:1594; for MAB44, the reverse primer was SEQ ID NO:1596; for MAB4, the reverse primer was SEQ ID NO:1600; for MAB9, the reverse primer was SEQ ID NO:1603 (MAB9); for MAB100, the reverse primer was SEQ ID NO:1606; for MAB13, the reverse primer was SEQ ID NO:1611; for MAB32, the reverse primer was SEQ ID NO:1614; for MAB35, the reverse primer was SEQ ID NO:1617; for MAB146, the reverse primer was SEQ ID NO:1620; for MAB2, the reverse primer was SEQ ID NO:1622; for MAB20, the reverse primer was SEQ ID NO:1626; for MAB43, the reverse primer was SEQ ID NO:1629; for MAB46, the reverse primer was SEQ ID NO:1633; for MAB50, the reverse primer was SEQ ID NO:1637; for MAB66, the reverse primer was SEQ ID NO:1640; for MAB4, the reverse primer was SEQ ID NO:1644; for MAB15 synthetic gene, the reverse primer was SEQ ID NO:1645; for MAB17 synthetic gene, the reverse primer was SEQ ID NO:1646; for MAB18 synthetic gene, the reverse primer was SEQ ID NO:1647; for MAB137 synthetic gene, the reverse primer was SEQ ID NO: 1648; and for MAB3 synthetic gene, the reverse primer was SEQ ID NO:1649, which are designed to span the introduced promoter and gene, in the binary vector.

Synthetic sequences [such as of MAB14, nucleotide SEQ ID NO:23, which encodes protein SEQ ID NO:219) of some of the cloned polynucleotides were ordered from a commercial supplier (GeneArt, GmbH). To optimize the coding sequence, codon-usage Tables calculated from plant transcriptomes were used [example of such Tables can be found in the Codon Usage Database available online at Hypertext Transfer Protocol://World Wide Web (dot) kazusa (dot) or (dot) jp/codon/]. The optimized coding sequences were designed in a way that no changes were introduced in the encoded amino acid sequence while using codons preferred for expression in dicotyledonous plants mainly tomato and *Arabidopsis*; and monocotyledonous plants such as maize. Such optimized sequences promote better translation rate and therefore higher protein expression levels. Parts of the sequences were ordered as the original sequences. To the optimized/non-optimized sequences flanking additional unique restriction enzymes sites were added to facilitate cloning genes in binary vectors.

Promoters used: *Arabidopsis* At6669 promoter (SEQ ID NO:1652; which is SEQ ID NO:61 of WO04081173 to Evogene Ltd.).

The sequences of the cloned cDNAs are provided in SEQ ID NOs: 1530-1534, 1536-1545, 1547-1566, 1654, 1665, 1666, 1667 and 1668. The protein translation of the amplified cDNA sequence matched exactly that of the initial bioinformatics prediction of the protein sequences. The predicted polypeptide sequences of the cloned polynucleotides are provided in SEQ ID NOs:201, 212, 284, 213, 217, 317, 219, 221, 224, 225, 226, 227, 229, 237, 203, 247, 252, 205, 265, 267, 271, 277, 207, 208, 211, 283, 1655, 311, 334, and 254.

Example 4

Transforming *Agrobacterium Tumefaciens* Cells with Binary Vectors Harboring Putative ABST Genes Each of the binary vectors described in Example 3 above are used to transform *Agrobacterium* cells. Two additional binary constructs, having a GUS/Luciferase reporter gene replacing the ABST gene (positioned downstream of the At6669 promoter), are used as negative controls.

The binary vectors are introduced to *Agrobacterium tumefaciens* GV301, or LB4404 competent cells (about $10^9$ cells/mL) by electroporation. The electroporation is performed using a MicroPulser electroporator (Biorad), 0.2 cm cuvettes (Biorad) and EC-2 electroporation program (Biorad). The treated cells are cultured in LB liquid medium at 28° C. for 3 hours, then plated over LB agar supplemented with gentamycin (50 mg/L; for *Agrobacterium* strains GV301) or streptomycin (300 mg/L; for *Agrobacterium* strain LB4404) and kanamycin (50 mg/L) at 28° C. for 48 hours. *Abrobacterium* colonies which developed on the selective media were analyzed by PCR using the primers described above (Example 3) with respect to identification of positive binary vector colonies. The resulting PCR products are isolated and sequenced as described in Example 3 above, to verify that the correct ABST sequences are properly introduced to the *Agrobacterium* cells.

Example 5

Transformation of *Arabidopsis Thaliana* Plants with Putative ABST Genes

*Arabidopsis thaliana* Columbia plants (To plants) are transformed using the Floral Dip procedure described by Clough and Bent (10) and by Desfeux et al. (11), with minor modifications. Briefly, $T_0$ Plants are sown in 250 ml pots filled with wet peat-based growth mix. The pots are covered with aluminum foil and a plastic dome, kept at 4° C. for 3-4 days, then uncovered and incubated in a growth chamber at 18-24° C. under 16/8 hour light/dark cycles. The $T_0$ plants are ready for transformation six days before anthesis.

Single colonies of *Agrobacterium* carrying the binary constructs, are generated as described in Example 4 above. Colonies are cultured in LB medium supplemented with kanamycin (50 mg/L) and gentamycin (50 mg/L). The cultures are incubated at 28° C. for 48 hours under vigorous shaking and then centrifuged at 4000 rpm for 5 minutes. The pellets comprising the *Agrobacterium* cells are re-suspended in a transformation medium containing half-strength (2.15 g/L) Murashige-Skoog (Duchefa); 0.044 µM benzylamino purine (Sigma); 112 µg/L B5 Gambourg vitamins (Sigma); 5% sucrose; and 0.2 ml/L Silwet L-77 (OSI Specialists, CT) in double-distilled water, at pH of 5.7.

Transformation of $T_0$ plants is performed by inverting each plant into an *Agrobacterium* suspension, such that the above ground plant tissue is submerged for 3-5 seconds. Each inoculated $T_0$ plant is immediately placed in a plastic tray, then covered with clear plastic dome to maintain humidity and is kept in the dark at room temperature for 18 hours, to facilitate infection and transformation. Transformed (transgenic) plants are then uncovered and transferred to a greenhouse for recovery and maturation. The transgenic $T_0$ plants are grown in the greenhouse for 3-5 weeks until siliques are brown and dry. Seeds are harvested from plants and kept at room temperature until sowing.

For generating $T_1$ and $T_2$ transgenic plants harboring the genes, seeds collected from transgenic $T_0$ plants are surface-sterilized by soaking in 70% ethanol for 1 minute, followed by soaking in 5% sodium hypochloride and 0.05% triton for 5 minutes. The surface-sterilized seeds are thoroughly washed in sterile distilled water then placed on culture plates containing half-strength Murashige-Skoog (Duchefa); 2% sucrose; 0.8% plant agar; 50 mM kanamycin; and 200 mM carbenicylin (Duchefa). The culture plates are incubated at 4° C. for 48 hours then transferred to a growth room at 25° C. for an additional week of incubation. Vital $T_1$ *Arabidopsis* plants are transferred to a fresh culture plates for another week of incubation. Following incubation the $T_1$ plants are removed from culture plates and planted in growth mix contained in 250 ml pots. The transgenic plants are allowed to grow in a greenhouse to maturity. Seeds harvested from $T_1$ plants are cultured and grown to maturity as $T_2$ plants under the same conditions as used for culturing and growing the $T_1$ plants.

Example 6

Improved ABST in Tissue Culture Assay

Assay 1: Plant Growth Under Osmotic Stress (PEG) in Tissue Culture Conditions

Osmotic stress (PEG)—conditions resembling the high osmolarity found during drought (e.g., 25% PEG8000). One of the consequences of drought is the induction of osmotic stress in the area surrounding the roots; therefore, in many scientific studies, PEG serves to simulate drought.

Surface sterilized seeds are sown in basal media [50% Murashige-Skoog medium (MS) supplemented with 0.8% plant agar as solidifying agent] in the presence of Kanamycin (for selecting only transgenic plants). After sowing, plates are transferred for 2-3 days at 4° C. for stratification and then grown at 25° C. under 12-hour light 12-hour dark daily cycles for 7 to 10 days. At this time point, seedlings randomly chosen are carefully transferred to plates hold 25% PEG in 0.5 MS media or normal conditions (0.5 MS media). Each plate contains 5 seedlings of same event, and 3-4 different plates (replicates) for each event. For each polynucleotide of the invention at least four independent transformation events are analyzed from each construct. Plants expressing the polynucleotides of the invention are compared to the average measurement of the control plants Mock-transgenic plants expressing the uidA reporter gene (GUS Intron—GUI) under the same promoter were used as control.

Digital Imaging

A laboratory image acquisition system, which consists of a digital reflex camera (Canon EOS 300D) attached with a 55 mm focal length lens (Canon EF-S series), mounted on a reproduction device (Kaiser RS), which included 4 light units (4×150 Watts light bulb) and located in a darkroom, was used for capturing images of plantlets sawn in square agar plates.

The image capturing process was repeated every 7 days starting at day 0 till day 14. The same camera attached with a 24 mm focal length lens (Canon EF series), placed in a custom made iron mount was used for capturing images.

An image analysis system was used, which consists of a personal desktop computer (Intel P4 3.0 GHz processor) and a public domain program—ImageJ 1.37 (Java based image processing program which was developed at the U.S. National Institutes of Health and freely available on the internet at Hypertext Transfer Protocol://rsbweb (dot) nih (dot) gov/). Images were captured in resolution of 6 Mega Pixels (3072×2048 pixels) and stored in a low compression JPEG (Joint Photographic Experts Group standard) format. Next, analyzed data was saved to text files and processed using the JMP statistical analysis software (SAS institute).

Seedling Analysis

Using the digital analysis seedling data was calculated, including leaf area, root coverage and root length.

The Relative Growth Rate (RGR) was calculated according to the following formula I.

Relative growth area rate=(ΔArea/Δt)*(1/Area t0)   Formula I:

Δt is the current analyzed image day subtracted from the initial day (t–t0). Thus, the relative growth area rate is in units of 1/day and length growth rate is in units of 1/day.

At the end of the experiment, plantlets were removed from the media and weighed for the determination of plant fresh weight. Relative Growth Rate is determined by comparing the leaf area, root length and root coverage between each couple of sequential photographs, and results are used to resolve the effect of the gene introduced on plant vigor, under osmotic stress, as well as under optimal conditions. Similarly, the effect of the gene introduced on biomass accumulation, under osmotic stress as well as under optimal conditions, is determined by comparing the plants' fresh weight to control plants (GUI).

Statistical Analyses

To identify outperforming genes and constructs, results from the independent transformation events are evaluate for the overall influence of the gene (gene effect) and for each of the tested events (best event). Student's t test were applied, using significance of $p<0.05$ or $p<0.1$. The JMP statistics software package is used (Version 5.2.1, SAS Institute Inc., Cary, N.C., USA).

Experimental Results

The polynucleotide sequences of the invention were assayed for a number of desired traits.

Tables 5-6 depict analyses of Leaf Area in plants overexpressing the polynucleotides of the invention under the regulation of 6669 promoter under 25% PEG conditions. Each Table represents an independent experiment, using 4 independent events per gene. Genes not connected by same letter as the control (A, B,) are significantly different from the control, with A indicating a difference at a $P<0.05$ level of significance and, A* a difference at a $P<0.1$ level of significance.

TABLE 5

Genes showing improve Leaf Area under 25% PEG
Leaf Area [cm^2], 25% PEG

| | Day 7 from planting | | | | Day 14 from planting | | | |
|---|---|---|---|---|---|---|---|---|
| Gene Id | LSM | Signif-icance* | LSM best Event | Signif-icance* | % improvement of Best event | LSM | Signif-icance* | LSM best Event | Signif-icance* | % improvement of Best event |
| GUI | 0.38 | B | 0.38 | B | | 0.68 | B | 0.68 | B | |
| MAB1 | 0.49 | A | 0.63 | A | 67 | 0.72 | B | 6 | 0.80 | 18 |
| MAB25 | 0.33 | C | 0.49 | A | 28 | 0.61 | B | 0.88 | A | 30 |

Table 5:
LSM = Least square mean;
% improvement = compare to control (GUI);
A meaning significant difference at P < 0.05, A* meaning significant difference at P < 0.1.
The SEQ ID NOs. of the cloned genes (according to the Gene Id) which are exogenously expressed in the plants are provided in Table 3 above.

TABLE 6

Genes showing improve Leaf Area under 25% PEG
Leaf Area [cm^2], 25% PEG

| | Day 7 from planting | | | | Day 14 from planting | | | |
|---|---|---|---|---|---|---|---|---|
| Gene Id | LSM | Signif-icance* | LSM best Event | Signif-icance* | % improvement of Best event | LSM | Signif-icance* | LSM best Event | Signif-icance* | % improvement of Best event |
| GUI | 0.23 | B | 0.23 | B | | 0.44 | B | 0.44 | B | |
| MAB15 | 0.25 | B | 0.32 | A | 43 | 0.36 | B | 0.48 | B | 9 |
| MAB17 | 0.27 | A | 0.36 | A | 57 | 0.46 | B | 0.65 | A | 48 |
| MAB18 | 0.30 | A | 0.36 | A | 57 | 0.39 | B | 0.51 | B | 15 |
| MAB35 | 0.21 | B | 0.26 | B | 14 | 0.38 | B | 0.60 | A | 36 |

Table 6:
LSM = Least square mean;
% improvement = compare to control (GUI);
A meaning significant difference at P < 0.05, A* meaning significant difference at P < 0.1.
The SEQ ID NOs. of the cloned genes (according to the Gene Id) which are exogenously expressed in the plants are provided in Table 3 above.

Tables 7-9 depict analyses of Roots Coverage in plants overexpressing the polynucleotides of the invention under the regulation of 6669 promoter under 25% PEG conditions. Each Table represents an independent experiment, using 4 independent events per gene. Genes not connected by same letter as the control (A, B,) are significantly different from the control.

TABLE 7

Roots Coverage [cm^2], 25% PEG

| Gene Id | Day 7 from planting | | | | | Day 14 from planting | | | | |
|---|---|---|---|---|---|---|---|---|---|---|
| | LSM | Signif-icance* | LSM best Event | Signif-icance* | % improvement of Best event | LSM | Signif-icance* | LSM best Event | Signif-icance* | % improvement of Best event |
| GUI | 4.37 | B | 4.37 | B | | 6.69 | B | 6.69 | B | |
| MAB1 | 7.17 | A | 10.32 | A | 136 | 9.25 | A | 9.73 | A | 45 |

Table 7:
LSM = Least square mean;
% improvement = compare to control (GUI);
A meaning significant difference at P < 0.05, A* meaning significant difference at P < 0.1.
The SEQ ID NOs. of the cloned genes (according to the Gene Id) which are exogenously expressed in the plants are provided in Table 3 above.

TABLE 8

Roots Coverage [cm^2], 25% PEG

| Gene Id | Day 7 from planting | | | | | Day 14 from planting | | | | |
|---|---|---|---|---|---|---|---|---|---|---|
| | LSM | Signif-icance* | LSM best Event | Signif-icance* | % improvement of Best event | LSM | Signif-icance* | LSM best Event | Signif-icance* | % improvement of Best event |
| GUI | 4.04 | B | 4.04 | B | | 11.09 | B | 11.09 | B | |
| MAB15 | 4.53 | B | 5.60 | A | 39 | 10.10 | B | 11.74 | B | 6 |
| MAB18 | 5.23 | A | 6.79 | A | 68 | 9.92 | B | 10.29 | B | −7 |
| MAB146 | 5.10 | B | 7.01 | A | 73 | 8.67 | B | 10.04 | B | −9 |

Table 8:
LSM = Least square mean;
% improvement = compare to control (GUI);
A meaning significant difference at P < 0.05, A* meaning significant difference at P < 0.1.
The SEQ ID NOs. of the cloned genes (according to the Gene Id) which are exogenously expressed in the plants are provided in Table 3 above.

TABLE 9

Roots Coverage [cm^2], 25% PEG

| Gene Id | Day 7 from planting | | | | | Day 14 from planting | | | | |
|---|---|---|---|---|---|---|---|---|---|---|
| | LSM | Signif-icance* | LSM best Event | Signif-icance* | % improvement of Best event | LSM | Signif-icance* | LSM best Event | Signif-icance* | % improvement of Best event |
| GUI | 2.11 | B | 2.11 | B | | 5.67 | B | 5.67 | B | |
| MAB18 | 2.05 | B | 2.75 | B | 30 | 5.40 | B | 8.76 | A | 55 |
| MAB32 | 1.98 | B | 5.06 | A | 140 | 4.31 | B | 10.55 | A | 86 |
| MAB35 | 2.62 | B | 3.82 | A | 81 | 7.19 | A* | 10.04 | A | 77 |
| MAB4 | 3.03 | A | 5.64 | A | 168 | 7.38 | A* | 11.38 | A | 101 |
| MAB146 | 1.84 | B | 3.65 | A | 73 | 5.05 | B | 9.21 | A | 63 |

Table 9:
LSM = Least square mean;
% improvement = compare to control (GUI);
A meaning significant difference at P < 0.05, A* meaning significant difference at P < 0.1.
The SEQ ID NOs. of the cloned genes (according to the Gene Id) which are exogenously expressed in the plants are provided in Table 3 above.

Tables 10-11 depict analyses of Roots Length in plants overexpressing the polynucleotides of the invention under the regulation of 6669 promoter in 25% PEG. Each Table represents an independent experiment, using 4 independent events per gene. Genes not connected by same letter as the control (A, B,) are significantly different from the control.

TABLE 10

Roots Length [cm], PEG 25%

| Gene Id | Day 7 from planting | | | | | Day 14 from planting | | | | |
|---|---|---|---|---|---|---|---|---|---|---|
| | LSM | Significance* | LSM best Event | Significance* | % improvement of Best event | LSM | Significance* | LSM best Event | Significance* | % improvement of Best event |
| GUI | 4.71 | A | 4.71 | A | | 5.71 | B | 5.71 | B | |
| MAB1 | 5.37 | A | 5.91 | A | 25 | 6.09 | B | 6.40 | B | 12 |

Table 10:
LSM = Least square mean;
% improvement = compare to control (GUI);
A meaning significant difference at P < 0.05, A* meaning significant difference at P < 0.1.
The SEQ ID NOs. of the cloned genes (according to the Gene Id) which are exogenously expressed in the plants are provided in Table 3 above.

TABLE 11

Roots Length [cm], PEG 25%

| Gene Id | Day 7 from planting | | | | | Day 14 from planting | | | | |
|---|---|---|---|---|---|---|---|---|---|---|
| | LSM | Significance* | LSM best Event | Significance* | % improvement of Best event | LSM | Significance* | LSM best Event | Significance* | % improvement of Best event |
| GUI | 2.88 | B | 2.88 | B | | 5.11 | B | 5.11 | B | |
| MAB18 | 3.22 | B | 4.29 | A | 49 | 4.86 | B | 6.33 | B | 24 |
| MAB32 | 2.74 | B | 5.78 | A | 101 | 3.75 | B | 7.17 | A | 40 |
| MAB35 | 3.35 | A* | 4.79 | A | 66 | 5.30 | B | 6.76 | A | 32 |
| MAB4 | 3.25 | B | 4.80 | A | 67 | 5.24 | B | 7.32 | A | 43 |
| MAB146 | 2.43 | B | 4.00 | A | 39 | 4.04 | B | 6.39 | A | 25 |

Table 11:
LSM = Least square mean;
% improvement = compare to control (GUI);
A meaning significant difference at P < 0.05, A* meaning significant difference at P < 0.1.
The SEQ ID NOs. of the cloned genes (according to the Gene Id) which are exogenously expressed in the plants are provided in Table 3 above.

Tables 12-13 depict analyses of Leaf Area RGR in plants overexpressing the polynucleotides of the invention under the regulation of 6669 promoter in 25% PEG. Each Table represents an independent experiment, using 4 independent events per gene. Genes not connected by same letter as the control (A, B,) are significantly different from the control.

TABLE 12

Leaf Area RGR [cm^2/day], PEG 25%

| Gene Id | Day 7 from planting | | | | | Day 14 from planting | | | | |
|---|---|---|---|---|---|---|---|---|---|---|
| | LSM | Significance* | LSM best Event | Significance* | % improvement of Best event | LSM | Significance* | LSM best Event | Significance* | % improvement of Best event |
| GUI | 0.46 | B | 0.46 | B | | 0.12 | B | 0.12 | B | |
| MAB1 | 0.68 | A | 1.47 | A | 222 | 0.20 | A | 0.30 | A | 151 |
| MAB17 | 0.43 | B | 0.50 | B | 8 | 0.17 | B | 0.29 | A | 145 |
| MAB35 | 0.65 | A | 0.71 | A | 54 | 0.19 | A | 0.23 | A | 93 |
| MAB146 | 0.55 | B | 0.80 | A | 75 | 0.16 | B | 0.20 | B | 66 |

Table 12:
LSM = Least square mean;
% improvement = compare to control (GUI);
A meaning significant difference at P < 0.05, A* meaning significant difference at P < 0.1.
The SEQ ID NOs. of the cloned genes (according to the Gene Id) which are exogenously expressed in the plants are provided in Table 3 above.

TABLE 13

Leaf Area RGR [cm^2/day], PEG 25%

| | Day 7 from planting | | | | Day 10 from planting | | | | |
|---|---|---|---|---|---|---|---|---|---|
| Gene Id | LSM | Signif- icance* | LSM best Event | Signif- icance* | % improvement of Best event | LSM | Signif- icance* | LSM best Event | Signif- icance* | % improvement of Best event |
| GUI | 0.49 | B | 0.49 | B | | 0.24 | B | 0.24 | B | |
| MAB6 | 0.89 | A | 1.60 | A | 226 | 0.27 | B | 0.33 | B | 39 |

Table 13:
LSM = Least square mean;
% improvement = compare to control (GUI);
A meaning significant difference at P < 0.05, A* meaning significant difference at P < 0.1.
The SEQ ID NOs. of the cloned genes (according to the Gene Id) which are exogenously expressed in the plants are provided in Table 3 above.

Tables 14-18 depict analyses of Roots Coverage RGR in plants overexpressing the polynucleotides of the invention under the regulation of 6669 promoter in 25% PEG. Each Table represents an independent experiment, using 4 independent events per gene. Genes not connected by same letter as the control (A, B,) are significantly different from the control.

TABLE 14

Roots Coverage RGR [cm^2/day], PEG 25%

| | Day 7 from planting | | | | Day 14 from planting | | | | |
|---|---|---|---|---|---|---|---|---|---|
| Gene Id | LSM | Signif- icance* | LSM best Event | Signif- icance* | % improvement of Best event | LSM | Signif- icance* | LSM best Event | Signif- icance* | % improvement of Best event |
| GUI | 5.74 | B | 5.74 | B | | 0.11 | B | 0.11 | B | |
| MAB25 | 4.03 | B | 5.44 | B | −5 | 0.16 | B | 0.21 | A | 96 |
| MAB44 | 5.32 | B | 7.79 | B | 36 | 0.17 | B | 0.28 | A | 155 |

Table 14:
LSM = Least square mean;
% improvement = compare to control (GUI);
A meaning significant difference at P < 0.05, A* meaning significant difference at P < 0.1.
The SEQ ID NOs. of the cloned genes (according to the Gene Id) which are exogenously expressed in the plants are provided in Table 3 above.

TABLE 15

Roots Coverage RGR [cm^2/day], PEG 25%

| | Day 7 from planting | | | | Day 14 from planting | | | | |
|---|---|---|---|---|---|---|---|---|---|
| Gene Id | LSM | Signif- icance* | LSM best Event | Signif- icance* | % improvement of Best event | LSM | Signif- icance* | LSM best Event | Signif- icance* | % improvement of Best event |
| GUI | 0.43 | B | 0.43 | B | | 0.30 | B | 0.30 | B | |
| MAB1 | 2.16 | A | 3.09 | A | 621 | 0.36 | B | 0.43 | A | 44 |
| MAB15 | 1.55 | A | 2.81 | A | 555 | 0.30 | B | 0.33 | B | 9 |
| MAB17 | 1.99 | A | 4.08 | A | 852 | 0.35 | B | 0.53 | A | 78 |
| MAB18 | 1.44 | A | 1.90 | A | 343 | 0.29 | B | 0.36 | B | 19 |
| MAB35 | 1.10 | B | 1.71 | B | 298 | 0.37 | B | 0.48 | A | 59 |
| MAB146 | 2.16 | A | 4.03 | A | 841 | 0.30 | B | 0.41 | A | 38 |

Table 15:
LSM = Least square mean;
% improvement = compare to control (GUI);
A meaning significant difference at P < 0.05, A* meaning significant difference at P < 0.1.
The SEQ ID NOs. of the cloned genes (according to the Gene Id) which are exogenously expressed in the plants are provided in Table 3 above.

TABLE 16

Roots Coverage RGR [cm^2/day], PEG 25%

| | Day 7 from planting | | | | | Day 14 from planting | | | | |
|---|---|---|---|---|---|---|---|---|---|---|
| Gene Id | LSM | Significance* | LSM best Event | Significance* | % improvement of Best event | LSM | Significance* | LSM best Event | Significance* | % improvement of Best event |
| GUI | 1.27 | B | 1.27 | B | | 0.08 | B | 0.08 | B | |
| MAB100 | 1.26 | B | 1.52 | B | 19 | 0.12 | B | 0.19 | A | 131 |
| MAB134 | 1.64 | A* | 2.20 | A | 73 | 0.08 | B | 0.12 | B | 48 |
| MAB13 | 1.57 | B | 2.16 | A | 70 | 0.19 | A | 0.32 | A | 294 |
| MAB15 | 1.61 | A* | 2.71 | A | 113 | 0.10 | B | 0.13 | B | 56 |
| MAB17 | 2.15 | A | 2.24 | A | 76 | 0.13 | B | 0.15 | B | 88 |
| MAB3_GA | 1.52 | B | 2.02 | A | 58 | 0.09 | B | 0.12 | B | 45 |

Table 16:
LSM = Least square mean;
% improvement = compare to control (GUI);
A meaning significant different at $P < 0.05$, A* meaning significant different at $P < 0.1$.
The SEQ ID NOs. of the cloned genes (according to the Gene Id) which are exogenously expressed in the plants are provided in Table 3 above.

TABLE 17

Roots Coverage RGR [cm^2/day], PEG 25%

| | Day 7 from planting | | | | | Day 14 from planting | | | | |
|---|---|---|---|---|---|---|---|---|---|---|
| Gene Id | LSM | Significance* | LSM best Event | Significance* | % improvement of Best event | LSM | Significance* | LSM best Event | Significance* | % improvement of Best event |
| GUI | 0.95 | B | 0.95 | B | | 0.30 | B | 0.30 | B | |
| MAB18 | 0.75 | B | 2.04 | A | 116 | 0.29 | B | 0.47 | A | 60 |
| MAB35 | 1.44 | A* | 4.53 | A | 379 | 0.32 | B | 0.48 | A | 63 |
| MAB4 | 1.28 | B | 2.17 | A | 129 | 0.29 | B | 0.44 | A | 49 |
| MAB146 | 0.47 | B | 0.86 | B | −9 | 0.35 | B | 0.45 | A | 52 |

Table17:
LSM = Least square mean;
% improvement = compare to control (GUI);
A meaning significant different at $P < 0.05$, A* meaning significant different at $P < 0.1$.
The SEQ ID NOs. of the cloned genes (according to the Gene Id) which are exogenously expressed in the plants are provided in Table 3 above.

TABLE 18

Roots Coverage RGR [cm^2/day], PEG 25%

| | Day 7 from planting | | | | | Day 10 from planting | | | | |
|---|---|---|---|---|---|---|---|---|---|---|
| Gene Id | LSM | Significance* | LSM best Event | Significance* | % improvement of Best event | LSM | Significance* | LSM best Event | Significance* | % improvement of Best event |
| GUI | 1.66 | B | 1.66 | B | | 0.21 | B | 0.21 | B | |
| MAB43 | 1.43 | B | 2.24 | B | 35 | 0.29 | A | 0.39 | A | 86 |

Table 18:
LSM = Least square mean;
% improvement = compare to control (GUI);
A meaning significant different at $P < 0.05$, A* meaning significant different at $P < 0.1$.
The SEQ ID NOs. of the cloned genes (according to the Gene Id) which are exogenously expressed in the plants are provided in Table 3 above.

Tables 19-21 depict analyses of Roots Length RGR in plants overexpressing the polynucleotides of the invention under the regulation of 6669 promoter in 25% PEG. Each Table represents an independent experiment, using 4 independent events per gene. Genes not connected by same letter as the control (A, B,) are significantly different from the control.

TABLE 19

| | Roots Length RGR [cm/day], PEG 25% | | | | | | | | |
|---|---|---|---|---|---|---|---|---|---|
| | Day 7 from planting | | | | | Day 14 from planting | | | |
| Gene Id | LSM | Significance* | LSM best Event | Significance* | % improvement of Best event | LSM | Significance* | LSM best Event | Significance* | % improvement of Best event |
| GUI | 0.23 | B | 0.23 | B | | 0.09 | B | 0.09 | B | |
| MAB1 | 0.46 | A | 0.58 | A | 148 | 0.12 | A | 0.14 | A | 58 |
| MAB15 | 0.43 | A | 0.58 | A | 148 | 0.08 | B | 0.10 | B | 16 |
| MAB17 | 0.45 | A | 0.57 | A | 147 | 0.11 | A | 0.16 | A | 87 |
| MAB18 | 0.41 | A | 0.44 | A | 89 | 0.10 | B | 0.13 | A | 45 |
| MAB35 | 0.31 | B | 0.37 | A | 59 | 0.10 | B | 0.13 | A | 51 |
| MAB146 | 0.49 | A | 0.65 | A | 178 | 0.09 | B | 0.10 | B | 17 |

Table 19:
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 20

| | Roots Length RGR [cm/day], PEG 25% | | | | | | | | |
|---|---|---|---|---|---|---|---|---|---|
| | Day 7 from planting | | | | | Day 14 from planting | | | |
| Gene Id | LSM | Significance* | LSM best Event | Significance* | % improvement of Best event | LSM | Significance* | LSM best Event | Significance* | % improvement of Best event |
| GUI | 0.20 | B | 0.20 | B | | 0.07 | B | 0.07 | B | |
| MAB134 | 0.28 | A | 0.33 | A | 68 | 0.07 | B | 0.08 | B | 16 |
| MAB13 | 0.34 | A | 0.46 | A | 133 | 0.11 | A | 0.15 | A | 113 |
| MAB15 | 0.30 | A | 0.47 | A | 139 | 0.06 | B | 0.07 | B | 1 |
| MAB17 | 0.39 | A | 0.44 | A | 121 | 0.09 | B | 0.10 | B | 39 |
| MAB3_GA | 0.28 | A | 0.34 | A | 72 | 0.05 | B | 0.08 | B | 8 |

Table 20;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 21

| | Roots Length RGR [cm/day], PEG 25% | | | | | | | | |
|---|---|---|---|---|---|---|---|---|---|
| | Day 7 from planting | | | | | Day 10 from planting | | | |
| Gene Id | LSM | Significance* | LSM best Event | Significance* | % improvement of Best event | LSM | Significance* | LSM best Event | Significance* | % improvement of Best event |
| GUI | 0.29 | B | 0.29 | B | | 0.11 | B | 0.11 | B | |
| MAB137 | 0.27 | B | 0.39 | A | 32 | 0.11 | B | 0.12 | B | 11 |
| MAB43 | 0.33 | B | 0.49 | A | 66 | 0.14 | A | 0.17 | A | 60 |
| MAB50 | 0.37 | A | 0.53 | A | 82 | 0.13 | B | 0.15 | A | 45 |
| MAB6 | 0.33 | B | 0.43 | A | 47 | 0.12 | B | 0.15 | B | 38 |

Table 21;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

Tables 22-23 depict analyses of Plant Fresh Weight in plants overexpressing the polynucleotides of the invention under the regulation of 6669 promoter in 25% PEG. Each Table represents an independent experiment, using 4 independent events per gene. Genes not connected by same letter as the control (A, B,) are significantly different from the control.

TABLE 22

Plant Fresh Weight [gr], PEG 25%

| Gene Id | LSM | Significance* | LSM best Event | Significance* | % improvement of Best event |
|---|---|---|---|---|---|
| GUI | 0.20 | B | 0.20 | B | |
| MAB15 | 0.25 | B | 0.30 | A | 51 |
| MAB18 | 0.21 | B | 0.26 | A | 33 |

LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 23

Plant Fresh Weight [gr], PEG 25%

| Gene Id | LSM | Significance* | LSM best Event | Significance* | % improvement of Best event |
|---|---|---|---|---|---|
| GUI | 0.18 | B | 0.18 | B | |
| MAB17 | 0.22 | B | 0.29 | A | 66 |
| MAB3_GA | 0.18 | B | 0.27 | A | 53 |

LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

Tables 24-27 depict analyses of Leaf Area in plants overexpressing the polynucleotides of the invention under the regulation of 6669 promoter in normal conditions. Each Table represents an independent experiment, using 4 independent events per gene. Genes not connected by same letter as the control (A, B,) are significantly different from the control.

TABLE 24

Leaf Area [cm^2], Normal Conditions

| | Day 7 from planting | | | | | Day 14 from planting | | | | |
|---|---|---|---|---|---|---|---|---|---|---|
| Gene Id | LSM | Significance* | LSM best Event | Significance* | % improvement of Best event | LSM | Significance* | LSM best Event | Significance* | % improvement of Best event |
| GUI | 0.49 | B | 0.49 | B | | 0.82 | B | 0.82 | B | |
| MAB1 | 0.65 | A | 0.73 | A | 47 | 1.00 | A | 1.13 | A | 38 |

Table 24;
LSM = Least square mean;
% improvement = compare to control (GUI);
A meaning significantly different at P < 0.05.
The SEQ ID NOs. of the cloned genes (according to the Gene Id) which are exogenously expressed in the plants are provided in Table 3 above.

TABLE 25

Leaf Area [cm^2], Normal Conditions

| | Day 7 from planting | | | | | Day 14 from planting | | | | |
|---|---|---|---|---|---|---|---|---|---|---|
| Gene Id | LSM | Significance* | LSM best Event | Significance* | % improvement of Best event | LSM | Significance* | LSM best Event | Significance* | % improvement of Best event |
| GUI | 0.24 | B | 0.24 | B | | 0.56 | B | 0.56 | B | |
| MAB17 | 0.31 | A | 0.34 | A | 40 | 0.73 | A | 0.90 | A | 61 |
| MAB18 | 0.29 | A | 0.37 | A | 52 | 0.69 | A | 0.79 | A | 42 |

Table 25:
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 26

Leaf Area [cm^2], Normal Conditions

| | Day 7 from planting | | | | | Day 14 from planting | | | | |
|---|---|---|---|---|---|---|---|---|---|---|
| Gene Id | LSM | Significance* | LSM best Event | Significance* | % improvement of Best event | LSM | Significance* | LSM best Event | Significance* | % improvement of Best event |
| GUI | 0.39 | B | 0.39 | B | | 0.98 | B | 0.98 | B | |
| MAB15 | 0.46 | A* | 0.61 | A | 57 | 1.22 | A | 1.38 | A | 41 |
| MAB17 | 0.46 | A* | 0.57 | A | 47 | 1.13 | A* | 1.32 | A | 34 |
| MAB3_GA | 0.38 | B | 0.56 | A | 45 | 0.97 | B | 1.38 | A | 40 |

Table 26:
LSM = Least square mean;
% improvement = compare to control (GUI); );
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 27

Leaf Area [cm^2], Normal conditions

| | Day 7 from planting | | | | | Day 10 from planting | | | | |
|---|---|---|---|---|---|---|---|---|---|---|
| Gene Id | LSM | Significance* | LSM best Event | Significance* | % improvement of Best event | LSM | Significance* | LSM best Event | Significance* | % improvement of Best event |
| GUI | 0.34 | B | 0.34 | B | | 0.67 | B | 0.67 | B | |
| MAB6 | 0.32 | B | 0.41 | A | 19 | 0.60 | B | 0.74 | B | 0.60 |

Table 27:
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

Tables 28-31 depict analyses of Roots Coverage in plants overexpressing the polynucleotides of the invention under the regulation of 6669 promoter in normal conditions. Each Table represents an independent experiment, using 4 independent events per gene. Genes not connected by same letter as the control (A, B,) are significantly different from the control.

TABLE 28

Roots Coverage [cm^2], Normal conditions

| | Day 7 from planting | | | | | Day 14 from planting | | | | |
|---|---|---|---|---|---|---|---|---|---|---|
| Gene Id | LSM | Significance* | LSM best Event | Significance* | % improvement of Best event | LSM | Significance* | LSM best Event | Significance* | % improvement of Best event |
| GUI | 3.34 | B | 3.34 | B | | 11.61 | B | 11.61 | B | |
| MAB18 | 3.31 | B | 4.78 | A | 43 | 10.66 | B | 13.30 | B | 14 |

Table 28;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 29

Roots Coverage [cm^2], Normal conditions
Day 7 from planting

| Gene Id | LSM | Significance* | LSM best Event | Significance* | % improvement of Best event |
|---|---|---|---|---|---|
| GUI | 5.40 | B | 5.40 | B | |
| MAB100 | 5.05 | B | 7.06 | A | 31 |

LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 30

Roots Coverage [cm^2], Normal conditions

| | Day 7 from planting | | | | | Day 14 from planting | | | | |
|---|---|---|---|---|---|---|---|---|---|---|
| Gene Id | LSM | Significance* | LSM best Event | Significance* | % improvement of Best event | LSM | Significance* | LSM best Event | Significance* | % improvement of Best event |
| GUI | 3.53 | B | 3.53 | B | | 8.52 | B | 8.52 | B | |
| MAB18 | 4.17 | A* | 5.30 | A | 50 | 9.81 | A* | 12.89 | A | 51 |
| MAB32 | 2.55 | B | 4.71 | A | 33 | 6.40 | B | 12.37 | A | 45 |
| MAB35 | 3.73 | B | 4.59 | A | 30 | 8.55 | B | 11.12 | A | 30 |
| MAB46 | 2.46 | B | 3.42 | B | -3 | 6.55 | B | 10.98 | A | 29 |
| MAB146 | 2.33 | B | 3.95 | B | 12 | 7.05 | B | 10.86 | A | 28 |

Table 30:
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 31

Roots Coverage [cm^2], Normal conditions

| | Day 7 from planting | | | | | Day 10 from planting | | | | |
|---|---|---|---|---|---|---|---|---|---|---|
| Gene Id | LSM | Significance* | LSM best Event | Significance* | % improvement of Best event | LSM | Significance* | LSM best Event | Significance* | % improvement of Best event |
| GUI | 3.73 | B | 3.73 | B | | 7.11 | B | 7.11 | B | |
| MAB6 | 3.63 | B | 4.94 | A | 33 | 6.30 | B | 8.00 | B | 13 |

Table 31:
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

Tables 32-33 depict analyses of Roots Length in plants overexpressing the polynucleotides of the invention under the regulation of 6669 promoter in normal conditions. Each Table represents an independent experiment, using 4 independent events per gene. Genes not connected by same letter as the control (A, B,) are significantly different from the control.

TABLE 32

Roots Length [cm], Normal conditions

| | Day 7 from planting | | | | | Day 14 from planting | | | | |
|---|---|---|---|---|---|---|---|---|---|---|
| Gene Id | LSM | Significance* | LSM best Event | Significance* | % improvement of Best event | LSM | Significance* | LSM best Event | Significance* | % improvement of Best event |
| GUI | 5.89 | B | 5.89 | B | | 6.82 | B | 6.82 | B | |
| MAB1 | 6.73 | A | 7.39 | A | 26 | 7.02 | B | 7.63 | B | 12 |
| MAB10 | 5.45 | B | 8.07 | A | 37 | 5.83 | B | 8.18 | B | 20 |

Table 32:
LSM = Least square mean
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 33

Roots Length [cm], Normal conditions

| | Day 7 from planting | | | | | Day 14 from planting | | | | |
|---|---|---|---|---|---|---|---|---|---|---|
| Gene Id | LSM | Significance* | LSM best Event | Significance* | % improvement of Best event | LSM | Significance* | LSM best Event | Significance* | % improvement of Best event |
| GUI | 3.96 | B | 3.96 | B | | 6.51 | B | 6.51 | B | |
| MAB18 | 5.07 | A | 5.70 | A | 44 | 7.08 | A | 8.03 | A | 23 |
| MAB32 | 3.68 | B | 6.12 | A | 55 | 5.82 | B | 8.22 | A | 26 |
| MAB35 | 4.58 | A | 5.76 | A | 46 | 6.77 | B | 7.75 | A | 19 |
| MAB46 | 3.39 | B | 4.31 | B | 9 | 5.55 | B | 7.42 | A | 14 |
| MAB146 | 3.14 | B | 4.82 | A | 22 | 5.47 | B | 7.48 | A | 15 |

Table 33:
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

Tables 34-36 depict analyses of Leaf Area RGR in plants overexpressing the polynucleotides of the invention under the regulation of 6669 promoter in normal conditions. Each Table represents an independent experiment, using 4 independent events per gene. Genes not connected by same letter as the control (A, B,) are significantly different from the control.

TABLE 34

Leaf Area RGR [cm/day], Normal conditions

| | Day 7 from planting | | | | | Day 14 from planting | | | | |
|---|---|---|---|---|---|---|---|---|---|---|
| Gene Id | LSM | Significance* | LSM best Event | Significance* | % improvement of Best event | LSM | Significance* | LSM best Event | Significance* | % improvement of Best event |
| GUI | 0.43 | B | 0.43 | B | | 0.20 | B | 0.20 | B | |
| MAB15 | 0.79 | A | 1.25 | A | 189 | 0.21 | B | 0.27 | B | 36 |
| MAB146 | 0.62 | B | 0.97 | A | 124 | 0.15 | C | 0.18 | B | −13 |

Table 34:
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 35

Leaf Area RGR [cm/day], Normal conditions

| | Day 7 from planting | | | | | Day 14 from planting | | | | |
|---|---|---|---|---|---|---|---|---|---|---|
| Gene Id | LSM | Signif-icance* | LSM best Event | Signif-icance* | % improvement of Best event | LSM | Signif-icance* | LSM best Event | Signif-icance* | % improvement of Best event |
| GUI | 0.73 | B | 0.73 | B | | 0.21 | B | 0.21 | B | |
| MAB100 | 0.72 | B | 1.00 | A | 37 | 0.27 | B | 0.32 | A | 48 |
| MAB134 | 0.85 | B | 0.92 | B | 27 | 0.31 | A | 0.37 | A | 75 |
| MAB15 | 0.88 | A* | 1.24 | A | 70 | 0.28 | B | 0.33 | A | 56 |
| MAB17 | 0.91 | A | 1.18 | A | 62 | 0.26 | B | 0.33 | A | 55 |
| MAB3_GA | 0.88 | B | 1.16 | A | 59 | 0.27 | B | 0.31 | B | 46 |

Table 35:
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 36

Leaf Area RGR [cm/day], Normal conditions

| | Day 7 from planting | | | | | Day 14 from planting | | | | |
|---|---|---|---|---|---|---|---|---|---|---|
| Gene Id | LSM | Signif-icance* | LSM best Event | Signif-icance* | % improvement of Best event | LSM | Signif-icance* | LSM best Event | Signif-icance* | % improvement of Best event |
| GUI | 0.92 | B | | | | 0.29 | B | 0.29 | B | |
| MAB32 | 0.95 | B | 1.31 | A | 43 | 0.28 | B | 0.31 | B | 5 |

Table 36:
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

Tables 37-41 depict analyses of Roots Coverage RGR in plants overexpressing the polynucleotides of the invention under the regulation of 6669 promoter in normal conditions. Each Table represents an independent experiment, using 4 independent events per gene. Genes not connected by same letter as the control (A, B,) are significantly different from the control.

TABLE 37

Roots Coverage RGR [cm/day], Normal conditions

| | Day 7 from planting | | | | | Day 14 from planting | | | | |
|---|---|---|---|---|---|---|---|---|---|---|
| Gene Id | LSM | Signif-icance* | LSM best Event | Signif-icance* | % improvement of Best event | LSM | Signif-icance* | LSM best Event | Signif-icance* | % improvement of Best event |
| GUI | 5.62 | B | 5.62 | B | | 0.18 | B | 0.18 | B | |
| MAB10 | 7.69 | B | 15.10 | A | 168 | 0.08 | B | 0.14 | B | −20 |
| MAB44 | 5.28 | B | 11.69 | A | 108 | 0.13 | B | 0.17 | B | −5 |

Table 37:
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 38

Roots Coverage RGR [cm/day], Normal conditions

| | Day 7 from planting | | | | | Day 14 from planting | | | | |
|---|---|---|---|---|---|---|---|---|---|---|
| Gene Id | LSM | Signif-icance* | LSM best Event | Signif-icance* | % improvement of Best event | LSM | Signif-icance* | LSM best Event | Signif-icance* | % improvement of Best event |
| GUI | 0.23 | B | 0.23 | B | | 0.40 | B | 0.40 | B | |
| MAB1 | 0.90 | A | 1.23 | A | 444 | 0.33 | B | 0.42 | B | 7 |
| MAB15 | 1.06 | A | 1.65 | A | 628 | 0.34 | B | 0.42 | B | 6 |
| MAB18 | 0.94 | A | 1.76 | A | 677 | 0.37 | B | 0.52 | B | 32 |
| MAB35 | 0.56 | B | 1.00 | A | 342 | 0.38 | B | 0.41 | B | 3 |
| MAB146 | 0.80 | A | 1.09 | A | 381 | 0.35 | B | 0.50 | B | 26 |

Table 38;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 39

Roots Coverage RGR [cm/day], Normal conditions

| | Day 7 from planting | | | | | Day 14 from planting | | | | |
|---|---|---|---|---|---|---|---|---|---|---|
| Gene Id | LSM | Signif-icance* | LSM best Event | Signif-icance* | % improvement of Best event | LSM | Signif-icance* | LSM best Event | Signif-icance* | % improvement of Best event |
| GUI | 1.64 | B | 1.64 | B | | 0.12 | B | 0.12 | B | |
| MAB134 | 3.09 | A | 4.38 | A | 167 | 0.14 | B | 0.17 | B | 35 |
| MAB13 | 2.47 | A | 2.82 | A | 72 | 0.11 | B | 0.13 | B | 6 |
| MAB15 | 1.96 | B | 2.75 | A | 68 | 0.15 | B | 0.16 | B | 33 |
| MAB17 | 2.09 | B | 3.09 | A | 89 | 0.15 | B | 0.20 | A | 60 |

Table 39:
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 40

Roots Coverage RGR [cm/day], Normal conditions

| | Day 7 from planting | | | | | Day 14 from planting | | | | |
|---|---|---|---|---|---|---|---|---|---|---|
| Gene Id | LSM | Signif-icance* | LSM best Event | Signif-icance* | % improvement of Best event | LSM | Signif-icance* | LSM best Event | Signif-icance* | % improvement of Best event |
| GUI | 2.53 | B | 2.53 | B | | 0.24 | B | 0.24 | B | |
| MAB35 | 1.66 | B | 4.14 | A | 63 | 0.29 | B | 0.54 | A | 123 |
| MAB4 | 1.46 | B | 2.64 | B | 4 | 0.32 | B | 0.42 | A | 73 |
| MAB146 | 0.62 | B | 0.95 | B | −63 | 0.41 | A | 0.75 | A | 207 |

Table 40:
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 41

Roots Coverage RGR [cm/day], Normal conditions

| Gene Id | Day 7 from planting | | | | | Day 10 from planting | | | | |
|---------|-----|--------------|-------------------|--------------|----------------------------------|------|--------------|-------------------|--------------|----------------------------------|
|         | LSM | Significance* | LSM best Event | Significance* | % improvement of Best event | LSM | Significance* | LSM best Event | Significance* | % improvement of Best event |
| GUI     | 1.08 | B | 1.08 | B |     | 0.31 | B | 0.31 | B |     |
| MAB137  | 1.36 | B | 2.03 | A | 88  | 0.26 | B | 0.31 | B | 1   |
| MAB43   | 1.39 | B | 2.35 | A | 118 | 0.23 | B | 0.27 | B | -12 |
| MAB50   | 1.57 | A | 1.98 | A | 83  | 0.27 | B | 0.30 | B | -3  |
| MAB6    | 1.16 | B | 1.94 | A | 80  | 0.25 | B | 0.29 | B | -6  |
| MAB99   | 1.48 | A | 2.63 | A | 144 | 0.21 | B | 0.27 | B | -13 |

Table 41:
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

Tables 42-46 depict analyses of Roots Length RGR in plants overexpressing the polynucleotides of the invention under the regulation of 6669 promoter in normal conditions. Each Table represents an independent experiment, using 4 independent events per gene. Genes not connected by same letter as the control (A, B,) are significantly different from the control.

TABLE 42

Roots Length RGR [cm/day], Normal conditions
Day 7 from planting

| Gene Id | LSM | Significance* | LSM best Event | Significance* | % improvement of Best event |
|---------|------|---|------|---|----|
| GUI     | 1.07 | B | 1.07 | B |    |
| MAB10   | 1.29 | B | 2.01 | A | 88 |

LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 43

Roots Length RGR [cm/day], Normal conditions
Day 7 from planting

| Gene Id | LSM | Significance* | LSM best Event | Significance* | % improvement of Best event |
|---------|------|---|------|---|-----|
| GUI     | 0.17 | B | 0.17 | B |     |
| MAB1    | 0.26 | A | 0.34 | A | 93  |
| MAB15   | 0.32 | A | 0.45 | A | 156 |
| MAB17   | 0.24 | A | 0.28 | A | 61  |
| MAB18   | 0.30 | A | 0.41 | A | 136 |
| MAB146  | 0.26 | A | 0.34 | A | 93  |

LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 44

Roots Length RGR [cm/day], Normal conditions

| Gene Id | Day 7 from planting | | | | | Day 14 from planting | | | | |
|---------|------|---------------|----------------|--------------|----------------------------|------|--------------|----------------|--------------|----------------------------|
|         | LSM | Significance* | LSM best Event | Significance* | % improvement of Best event | LSM | Significance* | LSM best Event | Significance* | % improvement of Best event |
| GUI     | 0.29 | B  | 0.29 | B |     | 0.08 | B | 0.08 | B |    |
| MAB100  | 0.36 | B  | 0.39 | B | 31  | 0.08 | B | 0.13 | A | 67 |
| MAB134  | 0.51 | A  | 0.63 | A | 115 | 0.08 | B | 0.09 | B | 23 |
| MAB13   | 0.50 | A  | 0.61 | A | 107 | 0.08 | B | 0.09 | B | 19 |
| MAB15   | 0.40 | A  | 0.53 | A | 79  | 0.08 | B | 0.09 | B | 19 |
| MAB17   | 0.38 | A* | 0.44 | A | 49  | 0.10 | A | 0.13 | A | 70 |

Table 44:
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 45

Roots Length RGR [cm/day], Normal conditions
Day 14 from planting

| Gene Id | LSM | Significance* | LSM best Event | Significance* | % improvement of Best event |
|---|---|---|---|---|---|
| GUI | 0.11 | B | 0.11 | B | |
| MAB32 | 0.11 | B | 0.15 | A | 35 |
| MAB35 | 0.11 | B | 0.20 | A | 76 |
| MAB4 | 0.11 | B | 0.17 | A | 50 |
| MAB146 | 0.15 | A | 0.19 | A | 71 |

LSM = Least square mean;
% improvement = compare to control (GUI); );
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 46

Roots Length RGR [cm/day], Normal conditions

| | Day 7 from planting | | | | Day 10 from planting | | | |
|---|---|---|---|---|---|---|---|---|
| Gene Id | LSM | Signif-icance* | LSM best Event | Signif-icance* | % improvement of Best event | LSM | Signif-icance* | LSM best Event | Signif-icance* | % improvement of Best event |
| GUI | 0.31 | B | 0.31 | B | | 0.12 | B | 0.12 | B | |
| MAB137 | 0.33 | B | 0.40 | A | 31 | 0.11 | B | 0.12 | B | −1 |
| MAB43 | 0.33 | B | 0.44 | A | 41 | 0.11 | B | 0.12 | B | −2 |
| MAB50 | 0.39 | A | 0.42 | A | 35 | 0.13 | B | 0.17 | A | 34 |
| MAB6 | 0.30 | B | 0.41 | A | 33 | 0.12 | B | 0.18 | A | 41 |

Table 46:
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

Tables 47-48 depict analyses of Plant Fresh Weight in plants overexpressing the polynucleotides of the invention under the regulation of 6669 promoter in normal conditions. Each Table represents an independent experiment, using 4 independent events per gene. Genes not connected by same letter as the control (A, B,) are significantly different from the control.

TABLE 47

Plant Fresh Weight [gr], Normal conditions
Day 14 from planting

| Gene Id | LSM | Significance* | LSM best Event | Significance* | % improvement of Best event |
|---|---|---|---|---|---|
| GUI | 0.15 | B | 0.15 | B | |
| MAB15 | 0.24 | A | 0.28 | A | 93 |
| MAB17 | 0.21 | A | 0.25 | A | 73 |
| MAB18 | 0.22 | A | 0.29 | A | 101 |

LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 48

Plant Fresh Weight [gr], Normal conditions
Day 14 from planting

| Gene Id | LSM | Significance* | LSM best Event | Significance* | % improvement of Best event |
|---|---|---|---|---|---|
| GUI | 0.20 | B | 0.20 | B | |
| MAB100 | 0.28 | A* | 0.33 | A | 62 |
| MAB134 | 0.23 | B | 0.34 | A | 64 |
| MAB13 | 0.31 | A | 0.35 | A | 73 |
| MAB15 | 0.38 | A | 0.42 | A | 106 |
| MAB17 | 0.37 | A | 0.53 | A | 159 |
| MAB3_GA | 0.28 | A* | 0.40 | A | 94 |

LSM = Least square mean;
% improvement = compare to control (GUI); );
A meaning significant different at P < 0.05, A* meaning significant different at P < 0.1.
The SEQ ID NOs. of the cloned genes (according to the Gene Id) which are exogenously expressed in the plants are provided in Table 3 above.

Assay 2: Plant Growth at Nitrogen Deficiency Under Tissue Culture Conditions

The present inventors have found the NUE (Nitrogen Utilization Efficiency) assay to be relevant for the evaluation of the ABST candidate genes, since NUE deficiency encourages root elongation, increase of root coverage and allows detecting the potential of the plant to generate a better root system under drought conditions. In addition, there are indications in the literature (Wesley et al., 2002 Journal of Experiment Botany Vol. 53, No. 366, pp. 13-25) that biological mechanisms of NUE and drought tolerance are linked.

Surface sterilized seeds are sown in basal media [50% Murashige-Skoog medium (MS) supplemented with 0.8% plant agar as solidifying agent] in the presence of Kanamycin (for selecting only transgenic plants). After sowing, plates are transferred for 2-3 days at 4° C. for stratification and then grown at 25° C. under 12-hour light 12-hour dark daily cycles for 7 to 10 days. At this time point, seedlings randomly chosen are carefully transferred to plates holding nitrogen-limiting conditions: 0.5 MS media in which the combined nitrogen concentration ($NH_4NO_3$ and $KNO_3$) is 0.75 mM (nitrogen deficient conditions) or to plates holding normal nitrogen conditions: 0.5 MS media in which the combined nitrogen concentration ($NH_4NO_3$ and $KNO_3$) is 3 mM (normal nitrogen concentration). All tissue culture experiments were grown at the same time (NUE, PEG and Normal). Results for growth under normal conditions for NUE are the same as for PEG and are presented in assay 1. Each plate contains 5 seedlings of the same event, and 3-4 different plates (replicates) for each event. For each polynucleotide of the invention at least four independent transformation events are analyzed from each construct. Plants expressing the polynucleotides of the invention are compared to the average measurement of the control plants (GUI-harboring the GUS gene under the same promoter) used in the same experiment.

Digital Imaging and Statistical Analysis

Parameters were measured and analyzed as described in Assay 1 above.

Experimental Results

The polynucleotide sequences of the invention were assayed for a number of desired traits.

Tables 49-53 depict analyses of Leaf Area in plants overexpressing the polynucleotides of the invention under the regulation of 6669 promoter in nitrogen deficient conditions. Each Table represents an independent experiment, using 4 independent events per gene. Genes not connected by same letter as the control (A, B) are significantly different from the control.

TABLE 49

Leaf Area [cm^2], NUE 0.75 mM

| | Day 7 from planting | | | | Day 14 from planting | | | |
|---|---|---|---|---|---|---|---|---|
| Gene Id | LSM | Significance* | LSM best Event | Significance* | % improvement of Best event | LSM | Significance* | LSM best Event | Significance* | % improvement of Best event |
| GUI | 0.45 | B | 0.45 | B | | 0.41 | B | 0.41 | B | |
| MAB1 | 0.49 | B | 0.65 | A | 44 | 0.50 | A | 0.55 | A | 35 |
| MAB10 | 0.46 | B | 0.62 | A | 38 | 0.51 | A | 0.69 | A | 68 |
| MAB6 | 0.42 | B | 0.53 | B | 17 | 0.49 | B | 0.61 | A | 49 |

Table 49:
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 50

Leaf Area [cm^2], NUE 0.75 mM

| | Day 7 from planting | | | | Day 14 from planting | | | |
|---|---|---|---|---|---|---|---|---|
| Gene Id | LSM | Significance* | LSM best Event | Significance* | % improvement of Best event | LSM | Significance* | LSM best Event | Significance* | % improvement of Best event |
| GUI | 0.23 | B | 0.23 | B | | 0.41 | B | 0.41 | B | |
| MAB1 | 0.22 | B | 0.24 | B | 5 | 0.50 | A | 0.55 | A | 35 |
| MAB15 | 0.25 | B | 0.32 | A | 43 | 0.51 | A | 0.69 | A | 68 |
| MAB17 | 0.27 | A | 0.36 | A | 57 | 0.55 | A | 0.70 | A | 72 |
| MAB18 | 0.30 | A | 0.36 | A | 57 | 0.59 | A | 0.73 | A | 80 |
| MAB35 | 0.21 | B | 0.26 | B | 14 | 0.49 | B | 0.61 | A | 49 |
| MAB146 | 0.26 | B | 0.28 | B | 23 | 0.55 | A | 0.60 | A | 48 |

Table 50:
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 51

Leaf Area [cm^2], NUE 0.75 mM
Day 7 from planting

| Gene Id | LSM | Significance* | LSM best Event | Significance* | % improvement of Best event |
|---|---|---|---|---|---|
| GUI | 0.34 | B | 0.34 | B | |
| MAB17 | 0.32 | B | 0.44 | A | 31 |
| MAB3_GA | 0.32 | B | 0.44 | A | 31 |

LSM = Least square mean;
% improvement = compare to control (GUI);
A meaning significant different at $P < 0.05$, A* meaning significant different at $P < 0.1$.
The SEQ ID NOs. of the cloned genes (according to the Gene Id) which are exogenously expressed in the plants are provided in Table 3 above.

TABLE 52

Leaf Area [cm^2], NUE 0.75 mM

| | Day 7 from planting | | | | | Day 14 from planting | | | | |
|---|---|---|---|---|---|---|---|---|---|---|
| Gene Id | LSM | Signif-icance* | LSM best Event | Signif-icance* | % improvement of Best event | LSM | Signif-icance* | LSM best Event | Signif-icance* | % improvement of Best event |
| GUI | 0.21 | B | 0.21 | B | | 0.63 | B | 0.63 | B | |
| MAB18 | 0.23 | B | 0.31 | A | 50 | 0.58 | B | 0.77 | A | 22 |
| MAB4 | 0.20 | B | 0.31 | A | 48 | 0.54 | B | 0.82 | A | 30 |
| MAB146 | 0.21 | B | 0.29 | A | 41 | 0.48 | C | 0.59 | B | −6 |

Table 52:
LSM = Least square mean;
% improvement = compare to control (GUI);
A meaning significant different at $P < 0.05$, A* meaning significant different at $P < 0.1$.
The SEQ ID NOs. of the cloned genes (according to the Gene Id) which are exogenously expressed in the plants are provided in Table 3 above.

TABLE 53

Leaf Area [cm^2], NUE 0.75 mM

| | Day 7 from planting | | | | | Day 10 from planting | | | | |
|---|---|---|---|---|---|---|---|---|---|---|
| Gene Id | LSM | Signif-icance* | LSM best Event | Signif-icance* | % improvement of Best event | LSM | Signif-icance* | LSM best Event | Signif-icance* | % improvement of Best event |
| GUI | 0.27 | B | 0.27 | B | | 0.51 | B | 0.51 | B | |
| MAB43 | 0.25 | B | 0.35 | A | 29 | 0.47 | B | 0.60 | B | 18 |
| MAB50 | 0.28 | B | 0.32 | B | 19 | 0.54 | B | 0.66 | A | 31 |
| MAB6 | 0.28 | B | 0.35 | A | 28 | 0.54 | B | 0.69 | A | 35 |
| MAB66 | 0.28 | B | 0.34 | A | 25 | 0.51 | B | 0.59 | B | 17 |
| MAB99 | 0.27 | B | 0.35 | A | 28 | 0.51 | B | 0.59 | B | 16 |

Table 53:
LSM = Least square mean;
% improvement = compare to control (GUI);
A meaning significant different at $P < 0.05$, A* meaning significant different at $P < 0.1$.
The SEQ ID NOs. of the cloned genes (according to the Gene Id) which are exogenously expressed in the plants are provided in Table 3 above.

Tables 54-57 depict analyses of Roots Coverage in plants overexpressing the polynucleotides of the invention under the regulation of 6669 promoter in nitrogen deficient conditions. Each Table represents an independent experiment, using 4 independent events per gene. Genes not connected by same letter as the control (A, B,) are significantly different from the control.

TABLE 54

Roots Coverage [cm^2], NUE 0.75 mM

| | Day 7 from planting | | | | | Day 14 from planting | | | | |
|---|---|---|---|---|---|---|---|---|---|---|
| Gene Id | LSM | Signif- icance* | LSM best Event | Signif- icance* | % improvement of Best event | LSM | Signif- icance* | LSM best Event | Signif- icance* | % improvement of Best event |
| GUI | 6.18 | B | 6.18 | B | | 14.36 | B | 14.36 | B | |
| MAB1 | 7.33 | B | 8.56 | A | 39 | 13.18 | B | 16.22 | B | 13 |
| MAB10 | 7.93 | A | 10.38 | A | 68 | 13.32 | B | 14.67 | B | 2 |
| MAB25 | 5.83 | B | 6.93 | B | 12 | 11.12 | B | 13.90 | B | −3 |
| MAB44 | 5.37 | B | 9.93 | A | 61 | 11.14 | A | 17.59 | B | 22 |
| MAB6 | 6.88 | B | 9.31 | A | 51 | 12.79 | B | 15.66 | B | 9 |

Table 54:
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 55

Roots Coverage [cm^2], NUE 0.75 mM

| | Day 7 from planting | | | | | Day 14 from planting | | | | |
|---|---|---|---|---|---|---|---|---|---|---|
| Gene Id | LSM | Significance* | LSM best Event | Significance* | % improvement of Best event | LSM | Significance* | LSM best Event | Significance* | % improvement of Best event |
| GUI | 4.04 | B | 4.04 | B | | 12.24 | B | 12.24 | B | |
| MAB15 | 4.53 | B | 5.60 | A | 39 | 13.70 | B | 16.40 | A | 34 |
| MAB17 | 4.15 | B | 4.85 | B | 20 | 13.16 | B | 15.06 | A | 23 |
| MAB18 | 5.23 | A | 6.79 | A | 68 | 14.47 | A | 15.52 | A | 27 |
| MAB35 | 4.03 | B | 4.90 | B | 21 | 13.95 | B | 15.62 | A | 28 |
| MAB146 | 5.10 | B | 7.01 | A | 73 | 14.65 | A | 15.70 | A | 28 |

Table 55;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 56

Roots Coverage [cm^2], NUE 0.75 mM

| | Day 7 from planting | | | | | Day 14 from planting | | | | |
|---|---|---|---|---|---|---|---|---|---|---|
| Gene Id | LSM | Significance* | LSM best Event | Significance* | % improvement of Best event | LSM | Significance* | LSM best Event | Significance* | % improvement of Best event |
| GUI | 3.14 | B | 3.14 | B | | 10.88 | B | 10.88 | B | |
| MAB18 | 5.39 | A | 7.64 | A | 144 | 12.76 | B | 16.64 | A | 53 |
| MAB32 | 3.58 | B | 7.13 | A | 127 | 9.79 | B | 16.22 | A | 49 |
| MAB35 | 5.00 | A | 6.49 | A | 107 | 13.31 | A | 15.36 | A | 41 |
| MAB4 | 4.16 | B | 7.34 | A | 134 | 12.00 | B | 16.52 | A | 52 |
| MAB46 | 3.01 | B | 3.78 | B | 21 | 8.35 | C | 12.09 | B | 11 |
| MAB146 | 4.22 | B | 7.34 | A | 134 | 11.48 | B | 14.98 | A | 38 |

Table 56;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 57

Roots Coverage [cm^2], NUE 0.75 mM

| | Day 7 from planting | | | | | Day 10 from planting | | | | |
|---|---|---|---|---|---|---|---|---|---|---|
| Gene Id | LSM | Significance* | LSM best Event | Significance* | % improvement of Best event | LSM | Significance* | LSM best Event | Significance* | % improvement of Best event |
| GUI | 4.56 | B | 4.56 | B | | 9.81 | B | 9.81 | B | |
| MAB6 | 5.66 | A | 7.98 | A | 75 | 10.61 | B | 14.87 | A | 52 |
| MAB66 | 5.83 | A | 6.58 | A | 44 | 10.31 | B | 11.49 | B | 17 |

Table 57;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

Tables 58-61 depict analyses of Roots Length in plants overexpressing the polynucleotides of the invention under the regulation of 6669 promoter in nitrogen deficient conditions. Each Table represents an independent experiment, using 4 independent events per gene. Genes not connected by same letter as the control (A, B,) are significantly different from the control.

TABLE 58

Roots Length [cm], NUE 0.75 mM
Day 7 from planting

| Gene Id | LSM | Significance* | LSM best Event | Significance* | % improvement of Best event |
|---|---|---|---|---|---|
| GUI | 6.31 | B | 6.31 | B | |
| MAB44 | 5.34 | B | 7.07 | A | 12 |

LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 59

Roots Length [cm], NUE 0.75 mM

| | Day 7 from planting | | | | | Day 14 from planting | | | | |
|---|---|---|---|---|---|---|---|---|---|---|
| Gene Id | LSM | Significance* | LSM best Event | Significance* | % improvement of Best event | LSM | Significance* | LSM best Event | Significance* | % improvement of Best event |
| GUI | 4.55 | B | 4.55 | B | | 7.23 | B | 7.23 | B | |
| MAB15 | 4.48 | B | 5.40 | A | 19 | 6.93 | B | 7.49 | B | 4 |
| MAB18 | 4.61 | B | 5.48 | A | 20 | 7.59 | B | 7.86 | B | 9 |
| MAB146 | 4.70 | B | 5.20 | B | 14 | 7.66 | B | 7.95 | A | 10 |

Table 59;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 60

Roots Length [cm], NUE 0.75 mM

| | Day 7 from planting | | | | | Day 14 from planting | | | | |
|---|---|---|---|---|---|---|---|---|---|---|
| Gene Id | LSM | Significance* | LSM best Event | Significance* | % improvement of Best event | LSM | Significance* | LSM best Event | Significance* | % improvement of Best event |
| GUI | 3.61 | B | 3.61 | B | | 6.15 | B | 6.15 | B | |
| MAB18 | 4.93 | A | 6.44 | A | 79 | 7.30 | A | 8.11 | A | 32 |
| MAB32 | 4.02 | B | 6.48 | A | 80 | 6.53 | B | 8.51 | A | 38 |
| MAB35 | 4.70 | A | 5.47 | A | 52 | 7.20 | A | 7.46 | A | 21 |
| MAB4 | 4.06 | A* | 5.54 | A | 54 | 6.60 | B | 8.02 | A | 30 |
| MAB146 | 3.77 | B | 5.54 | A | 54 | 6.09 | B | 7.19 | A | 17 |

Table 60;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 61

Roots Length [cm], NUE 0.75 mM
Day 7 from planting

| Gene Id | LSM | Significance* | LSM best Event | Significance* | % improvement of Best event |
|---|---|---|---|---|---|
| GUI | 4.87 | B | 4.87 | B | |
| MAB66 | 5.27 | B | 5.74 | A | 18 |

LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

Tables 62-64 depict analyses of Leaf Area RGR in plants overexpressing the polynucleotides of the invention under the regulation of 6669 promoter in nitrogen deficient conditions. Each Table represents an independent experiment, using 4 independent events per gene. Genes not connected by same letter as the control (A, B,) are significantly different from the control.

TABLE 63

Leaf area RGR [cm/day], NUE 0.75 mM
Day 7 from planting

| Gene Id | LSM | Significance* | LSM best Event | Significance* | % improvement of Best event |
|---|---|---|---|---|---|
| GUI | 0.80 | B | 0.80 | B | |
| MAB18 | 0.87 | B | 1.24 | A | 56 |
| MAB32 | 0.94 | B | 1.53 | A | 91 |
| MAB35 | 0.96 | B | 1.21 | A | 51 |
| MAB4 | 0.71 | B | 0.81 | B | 1 |
| MAB46 | 0.64 | B | 0.75 | B | −7 |
| MAB146 | 0.82 | B | 1.04 | B | 30 |

LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 62

Leaf area RGR [cm/day], NUE 0.75 mM

| | Day 7 from planting | | | | | Day 14 from planting | | | | |
|---|---|---|---|---|---|---|---|---|---|---|
| Gene Id | LSM | Significance* | LSM best Event | Significance* | % improvement of Best event | LSM | Significance* | LSM best Event | Significance* | % improvement of Best event |
| GUI | 0.46 | B | 0.46 | B | | 0.12 | B | 0.12 | B | |
| MAB1 | 0.68 | A | 1.47 | A | 222 | 0.20 | A | 0.30 | A | 151 |
| MAB17 | 0.43 | B | 0.50 | B | 8 | 0.17 | B | 0.29 | A | 145 |
| MAB35 | 0.65 | A | 0.71 | A | 54 | 0.19 | A | 0.23 | A | 93 |
| MAB146 | 0.55 | B | 0.80 | A | 75 | 0.16 | B | 0.20 | B | 66 |

Table 62; LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 64

Leaf area RGR [cm/day], NUE 0.75 mM

| | Day 7 from planting | | | | | Day 10 from planting | | | | |
|---|---|---|---|---|---|---|---|---|---|---|
| Gene Id | LSM | Significance* | LSM best Event | Significance* | % improvement of Best event | LSM | Significance* | LSM best Event | Significance* | % improvement of Best event |
| GUI | 1.22 | B | 1.22 | B | | 0.28 | B | 0.28 | B | |
| MAB137 | 2.12 | B | 5.12 | A | 319 | 0.29 | B | 0.35 | B | 25 |
| MAB43 | 1.94 | B | 5.18 | A | 323 | 0.29 | B | 0.35 | B | 28 |
| MAB50 | 1.15 | B | 1.76 | B | 44 | 0.32 | B | 0.41 | A | 50 |

Table 64;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

Tables 65-69 depict analyses of Roots Coverage RGR in plants overexpressing the polynucleotides of the invention under the regulation of 6669 promoter in nitrogen deficient conditions. Each Table represents an independent experiment, using 4 independent events per gene. Genes not connected by same letter as the control (A, B, C) are significantly different from the control.

TABLE 65

Roots Coverage RGR [cm/day], NUE 0.75 mM

| | Day 7 from planting | | | | | Day 14 from planting | | | | |
|---|---|---|---|---|---|---|---|---|---|---|
| Gene Id | LSM | Significance* | LSM best Event | Significance* | % improvement of Best event | LSM | Significance* | LSM best Event | Significance* | % improvement of Best event |
| GUI | 5.35 | B | 5.35 | B | | 0.28 | B | 0.28 | B | |
| MAB25 | 7.38 | B | 11.62 | A | 117 | 0.19 | C | 0.26 | B | −6 |
| MAB44 | 7.19 | B | 11.52 | A | 115 | 0.26 | B | 0.35 | B | 23 |

Table 65;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 66

Roots Coverage RGR [cm/day], NUE 0.75 mM

| | Day 7 from planting | | | | | Day 14 from planting | | | | |
|---|---|---|---|---|---|---|---|---|---|---|
| Gene Id | LSM | Significance* | LSM best Event | Significance* | % improvement of Best event | LSM | Significance* | LSM best Event | Significance* | % improvement of Best event |
| GUI | 0.43 | B | 0.43 | B | | 0.30 | B | 0.30 | B | |
| MAB1 | 2.16 | A | 3.09 | A | 621 | 0.36 | B | 0.43 | A | 44 |
| MAB15 | 1.55 | A | 2.81 | A | 555 | 0.30 | B | 0.33 | B | 9 |
| MAB17 | 1.99 | A | 4.08 | A | 852 | 0.35 | B | 0.53 | A | 78 |
| MAB18 | 1.44 | A | 1.90 | A | 343 | 0.29 | B | 0.36 | B | 19 |
| MAB35 | 1.10 | B | 1.71 | B | 298 | 0.37 | B | 0.48 | A | 59 |
| MAB146 | 2.16 | A | 4.03 | A | 841 | 0.30 | B | 0.41 | A | 38 |

Table 66;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 67

Roots Coverage RGR [cm/day], NUE 0.75 mM
Day 7 from planting

| Gene Id | LSM | Significance* | LSM best Event | Significance* | % improvement of Best event |
|---|---|---|---|---|---|
| GUI | 2.30 | B | 2.30 | B | |
| MAB100 | 2.85 | B | 4.02 | A | 74 |
| MAB134 | 4.27 | A | 5.99 | A | 160 |
| MAB13 | 3.95 | A | 4.84 | A | 110 |
| MAB15 | 3.05 | A* | 3.97 | A | 73 |
| MAB17 | 2.96 | B | 3.76 | A | 63 |

LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 68

Roots Coverage RGR [cm/day], NUE 0.75 mM

| | Day 7 from planting | | | | Day 14 from planting | | | |
|---|---|---|---|---|---|---|---|---|
| Gene Id | LSM | Significance* | LSM best Event | Significance* | % improvement of Best event | LSM | Significance* | LSM best Event | Significance* | % improvement of Best event |
| GUI | 2.28 | B | 2.28 | B | | 0.44 | B | 0.44 | B | |
| MAB35 | 2.02 | B | 4.82 | A | 111 | 0.33 | B | 0.53 | B | 20 |
| MAB4 | 1.80 | B | 2.90 | B | 27 | 0.40 | B | 0.63 | A | 42 |

Table 68;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 69

Roots Coverage RGR [cm/day], NUE 0.75 mM
Day 7 from planting

| Gene Id | LSM | Significance* | LSM best Event | Significance* | % improvement of Best event |
|---|---|---|---|---|---|
| GUI | 1.60 | B | 1.60 | B | |
| MAB137 | 2.19 | A | 2.55 | B | 60 |
| MAB43 | 2.00 | B | 2.75 | A | 72 |
| MAB50 | 2.26 | A | 3.28 | A | 105 |
| MAB6 | 2.45 | A | 2.96 | A | 85 |
| MAB66 | 1.81 | B | 2.87 | A | 80 |
| MAB99 | 2.25 | A | 3.73 | A | 133 |

LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

Tables 70-74 depict analyses of Roots Length RGR in plants overexpressing the polynucleotides of the invention under the regulation of 6669 promoter in nitrogen deficient conditions. Each Table represents an independent experiment, using 4 independent events per gene. Genes not connected by same letter as the control (A, B,) are significantly different from the control.

TABLE 70

Roots Length RGR [cm/day], NUE 0.75 mM

| Gene Id | Day 7 from planting | | | | | Day 14 from planting | | | | |
|---|---|---|---|---|---|---|---|---|---|---|
| | LSM | Significance* | LSM best Event | Significance* | % improvement of Best event | LSM | Significance* | LSM best Event | Significance* | % improvement of Best event |
| GUI | 0.99 | B | 0.99 | B | | 0.04 | B | 0.04 | B | |
| MAB44 | 1.10 | B | 1.64 | A | 65 | 0.06 | B | 0.09 | A | 108 |

Table 70;
LSM = Least square mean;
% improvement = compare to control (GUI);
A meaning significant different at $P < 0.05$, A* meaning significant different at $P < 0.1$.
The SEQ ID NOs. of the cloned genes (according to the Gene Id) which are exogenously expressed in the plants are provided in Table 3 above.

TABLE 71

Roots Length RGR [cm/day], NUE 0.75 mM

| Gene Id | Day 7 from planting | | | | | Day 14 from planting | | | | |
|---|---|---|---|---|---|---|---|---|---|---|
| | LSM | Significance* | LSM best Event | Significance* | % improvement of Best event | LSM | Significance* | LSM best Event | Significance* | % improvement of Best event |
| GUI | 0.23 | B | 0.23 | B | | 0.09 | B | 0.09 | B | |
| MAB1 | 0.46 | A | 0.58 | A | 148 | 0.12 | A | 0.14 | A | 58 |
| MAB15 | 0.43 | A | 0.58 | A | 148 | 0.08 | B | 0.10 | B | 16 |
| MAB17 | 0.45 | A | 0.57 | A | 147 | 0.11 | A | 0.16 | A | 87 |
| MAB18 | 0.41 | A | 0.44 | A | 89 | 0.10 | B | 0.13 | A | 45 |
| MAB35 | 0.31 | B | 0.37 | A | 59 | 0.10 | B | 0.13 | A | 51 |

Table 71;
LSM = Least square mean;
% improvement = compare to control (GUI);
A meaning significant different at $P < 0.05$, A* meaning significant different at $P < 0.1$.
The SEQ ID NOs. of the cloned genes (according to the Gene Id) which are exogenously expressed in the plants are provided in Table 3 above.

TABLE 72

Roots Length RGR [cm/day], NUE 0.75 mM

| Gene Id | Day 7 from planting | | | | | Day 14 from planting | | | | |
|---|---|---|---|---|---|---|---|---|---|---|
| | LSM | Significance* | LSM best Event | Significance* | % improvement of Best event | LSM | Significance* | LSM best Event | Significance* | % improvement of Best event |
| GUI | 0.35 | B | 0.35 | B | | 0.06 | B | 0.06 | B | |
| MAB100 | 0.46 | A | 0.61 | A | 73 | 0.08 | B | 0.11 | A | 80 |
| MAB134 | 0.62 | A | 0.73 | A | 107 | 0.09 | A | 0.10 | A | 60 |
| MAB13 | 0.69 | A | 0.84 | A | 140 | 0.08 | B | 0.11 | A | 66 |
| MAB15 | 0.52 | A | 0.58 | A | 66 | 0.07 | B | 0.09 | B | 44 |
| MAB17 | 0.52 | A | 0.64 | A | 81 | 0.08 | B | 0.09 | A | 44 |
| MAB3_GA | 0.44 | B | 0.51 | A | 46 | 0.07 | B | 0.09 | B | 38 |

Table 72;
LSM = Least square mean;
% improvement = compare to control (GUI);
A meaning significant different at $P < 0.05$, A* meaning significant different at $P < 0.1$.
The SEQ ID NOs. of the cloned genes (according to the Gene Id) which are exogenously expressed in the plants are provided in Table 3 above.

TABLE 73

Roots Length RGR [cm/day], NUE 0.75 mM

| | Day 7 from planting | | | | | Day 14 from planting | | | | |
|---|---|---|---|---|---|---|---|---|---|---|
| Gene Id | LSM | Significance* | LSM best Event | Significance* | % improvement of Best event | LSM | Significance* | LSM best Event | Significance* | % improvement of Best event |
| GUI | 0.61 | B | 0.61 | B | | 0.12 | B | 0.12 | B | |
| MAB35 | 0.52 | B | 0.91 | A | 48 | 0.10 | B | 0.16 | B | 29 |
| MAB4 | 0.53 | B | 0.65 | B | 6 | 0.12 | B | 0.19 | A | 52 |
| MAB146 | 0.37 | C | 0.42 | B | −31 | 0.12 | B | 0.17 | A | 39 |

Table 73;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 74

Roots Length RGR [cm/day], NUE 0.75 mM

| | Day 7 from planting | | | | | Day 10 from planting | | | | |
|---|---|---|---|---|---|---|---|---|---|---|
| Gene Id | LSM | Significance* | LSM best Event | Significance* | % improvement of Best event | LSM | Significance* | LSM best Event | Significance* | % improvement of Best event |
| GUI | 0.36 | B | 0.36 | B | | 0.11 | B | 0.11 | B | |
| MAB137 | 0.46 | A | 0.55 | A | 52 | 0.13 | B | 0.18 | A | 72 |
| MAB43 | 0.41 | B | 0.53 | A | 47 | 0.12 | B | 0.14 | B | 30 |
| MAB50 | 0.48 | A | 0.57 | A | 59 | 0.12 | B | 0.16 | A | 46 |
| MAB6 | 0.53 | A | 0.64 | A | 79 | 0.10 | B | 0.12 | B | 9 |
| MAB66 | 0.41 | B | 0.55 | A | 54 | 0.10 | B | 0.12 | B | 9 |
| MAB99 | 0.47 | A | 0.62 | A | 74 | 0.10 | B | 0.13 | B | 19 |

Table 74;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

Tables 75-76 depict analyses of Plant Fresh Weight in plants overexpressing the polynucleotides of the invention under the regulation of 6669 promoter in nitrogen deficient conditions. Each Table represents an independent experiment, using 4 independent events per gene. Genes not connected by same letter as the control (A, B,) are significantly different from the control.

TABLE 75

Plant Fresh Weight [gr], NUE 0.75 mM
Day 14 from planting

| Gene Id | LSM | Significance* | LSM best Event | Significance* | % improvement of Best event |
|---|---|---|---|---|---|
| GUI | 0.15 | B | | | |
| MAB1 | 0.25 | A | 0.46 | A | 208 |
| MAB6 | 0.20 | B | 0.29 | A | 95 |

LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 76

Plant Fresh Weight [gr], NUE 0.75 mM
Day 10 from planting

| Gene Id | LSM | Significance* | LSM best Event | Significance* | % improvement of Best event |
|---|---|---|---|---|---|
| GUI | 0.15 | B | | | |
| MAB137 | 0.18 | A | 0.19 | A | 31 |
| MAB50 | 0.16 | B | 0.22 | A | 49 |
| MAB6 | 0.16 | B | 0.22 | A | 52 |
| MAB66 | 0.15 | B | 0.19 | A | 32 |

LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

Example 7

Improved ABST in Greenhouse Assay

ABS Tolerance: Yield and Plant Growth Rate at High Salinity Concentration Under Greenhouse Conditions This assay follows the rosette area growth of plants grown in the greenhouse as well as seed yield at high salinity irrigation. Seeds were sown in agar media supplemented only with a selection agent (Kanamycin) and Hoagland solution under nursery conditions. The $T_2$ transgenic seedlings are then transplanted to 1.7 trays filled with peat and perlite. The trails were irrigated with tap water (provided from the pots' bottom). Half of the plants are irrigated with a salt solution (40-80 mM NaCl and 5 mM $CaCl_2$) to induce salinity stress (stress conditions). The other half of the plants are continued to be irrigated with tap water (normal conditions). All plants are grown in the greenhouse until plants reach the mature seeds stage, then harvested (the above ground tissue) and weighted (immediately or following drying in oven at 50° C. for 24 hour). High salinity conditions are achieved by irrigation with a solution containing 40-80 mM NaCl ("ABS" growth conditions) and are compared to regular growth conditions.

The plants were analyzed for their overall size, growth rate, seed yield, and weight of 1,000 seeds, dry matter and harvest index (HI— seed yield/dry matter). Transgenic plants performance was compared to control plants grown in parallel under the same conditions. Mock-transgenic plants expressing the uidA reporter gene (GUS Intron—GUI) under the same promoter were used as control.

The experiment is planned in nested randomized plot distribution. High salinity conditions are achieved by irrigation with a solution containing 40-80 mM NaCl ("ABS" growth conditions).

Digital Imaging

A laboratory image acquisition system, which consists of a digital reflex camera (Canon EOS 300D) attached with a 55 mm focal length lens (Canon EF-S series), mounted on a reproduction device (Kaiser RS), which included 4 light units (4×150 Watts light bulb) was used for capturing images of plantlets.

Figure 2B:
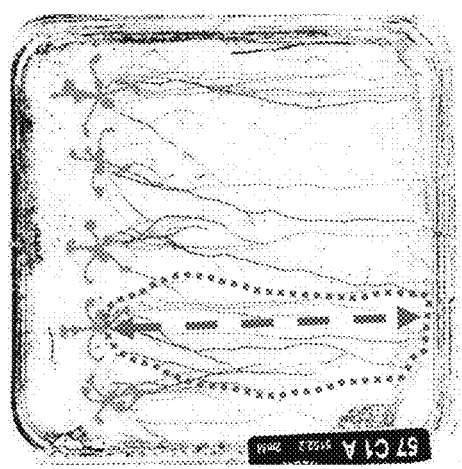
FIGS. 2a-2b are images depicting visualization of root development of plants grown in transparent agar plates. The different transgenes were grown in transparent agar plates for 17 days and the plates were photographed every 2 days starting at day 7.
Figure 2A:
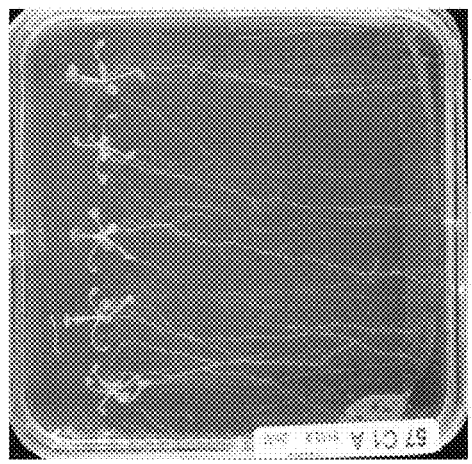

The image capturing process was repeated every 2-3 days starting at day 1 after sowing till day 10. The same camera attached with a 24 mm focal length lens (Canon EF series), placed in a custom made iron mount, was used for capturing images of larger plants sawn in white tubs in an environmental controlled greenhouse (as seen on FIGS. 2a-b). The tubs were square shape include 1.7 liter trays. During the capture process, the trays were placed beneath the iron mount, while avoiding direct sun light and casting of shadows. This process was repeated every 2-3 days for up to 10 days.

An image analysis system was used, which consists of a personal desktop computer (Intel P4 3.0 GHz processor) and a public domain program—ImageJ 1.37 (Java based image processing program which was developed at the U.S. National Institutes of Health and freely available on the internet at Hypertext Transfer Protocol://rsbweb (dot) nih (dot) gov/). Images were captured in resolution of 6 Mega Pixels (3072×2048 pixels) and stored in a low compression JPEG (Joint Photographic Experts Group standard) format. Next, analyzed data was saved to text files and processed using the JMP statistical analysis software (SAS institute).

Vegetative Parameters Analysis

Using the digital analysis leaves data was calculated, including leaf Average area, Rosette diameter and rosette area. The Relative Growth Rate (RGR) for the rosette parameters was calculated according to Formula I as described in Example 6. On day 80 from sowing, the plants were harvested and left to dry at 30° C. in a drying chamber. The biomass and seed weight of each plot was separated, measured and divided by the number of plants. Dry weight=total weight of the vegetative portion above ground (excluding roots) after drying at 30° C. in a drying chamber; Seed yield per plant=total seed weight per plant (gr).

The weight of 1000 seeds was determine as follows: seeds were scattered on a glass tray and a picture was taken. Each sample was weighted and then using the digital analysis, the number of seeds in each sample was calculated. 1000 seeds weight was calculated using formula II:

1000 Seed Weight=number of seed in sample/sample weight×1000  Formula II

Harvest Index—The harvest index was calculated using Formula III

Harvest Index=Average seed yield per plant/Average dry weight  Formula III:

Each construct is validated in its T2 generation. Transgenic plants expressing the uidA reporter gene (GUI) under the same promoter are used as control.

Statistical Analyses

To identify genes conferring significantly improved tolerance to abiotic stresses or enlarged root architecture, the results obtained from the transgenic plants are compared to those obtained from control plants. To identify outperforming genes and constructs, results from the independent transformation events tested are analyzed separately. In addition, genes and constructs are also analyzed taking into consideration the results obtained from all the independent transformation events tested the specific construct. For gene versus control analysis Student's t test were applied, using significance of P<0.05 or P<0.1. The JMP statistics software package is used (Version 5.2.1, SAS Institute Inc., Cary, N.C., USA).

Experimental Results

The polynucleotide sequences of the invention were assayed for a number of desired traits.

Tables 77-86 depict analyses of Rosette Area in plants overexpressing the polynucleotides of the invention under the regulation of 6669 promoter. Each Table represents an independent experiment, using 4 independent events per gene. Genes not connected by same letter as the control (A, B,) are significantly different from the control.

TABLE 77

| | Rosette Area [cm^2] 80 mM NaCl, Day 3 from planting | | | | |
|---|---|---|---|---|---|
| Gene Id | LSM | Significance* | LSM best Event | Significance* | % improvement of Best event |
| GUI | 0.58 | B | 0.58 | B | |
| MAB20 | 0.59 | B | 0.84 | A | 43 |
| MAB50 | 0.57 | B | 0.88 | A | 51 |

LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 78

Rosette Area [cm^2]
80 mM NaCl, Day 5 from planting

| Gene Id | LSM | Significance* | LSM best Event | Significance* | % improvement of Best event |
|---|---|---|---|---|---|
| GUI | 1.27 | B | 1.27 | B | |
| MAB20 | 1.20 | B | 1.73 | a | 36 |
| MAB50 | 1.2] | B | 2.04 | a | 61 |

LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 79

Rosette Area [cm^2]
80 mM NaCl, Day 8 from planting

| Gene Id | LSM | Significance* | LSM best Event | Significance* | % improvement of Best event |
|---|---|---|---|---|---|
| GUI | 3.62 | B | 3.62 | B | |
| MAB20 | 3.97 | B | 5.18 | A | 43 |
| MAB50 | 3.88 | B | 6.11 | A | 69 |

LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 80

Rosette Area [cm^2]
80 mM NaCl, Day 10 from planting

| Gene Id | LSM | Significance* | LSM best Event | Significance* | % improvement of Best event |
|---|---|---|---|---|---|
| GUI | 7.22 | B | 7.22 | B | |
| MAB50 | 6.75 | B | 10.18 | A | 41 |

LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 81

Rosette Area [cm^2]
80 mM NaCl, Day 3 from planting

| Gene Id | LSM | Significance* | LSM best Event | Significance* | % improvement of Best event |
|---|---|---|---|---|---|
| GUI | 1.63 | B | 1.63 | B | |
| MAB1 | 2.03 | A | 2.29 | A | 40 |
| MAB6 | 1.34 | B | 2.40 | A | 47 |

LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 82

Rosette Area [cm^2]
80 mM NaCl, Day 5 from planting

| Gene Id | LSM | Significance* | LSM best Event | Significance* | % improvement of Best event |
|---|---|---|---|---|---|
| GUI | 2.88 | B | 2.88 | B | |
| MAB1 | 3.41 | A* | 3.76 | A | 31 |

LSM = Least square mean;
% improvement = compare to control (GUI);
A meaning significant different at P < 0.05, A* meaning significant different at P < 0.1; .
The SEQ ID NOs. of the cloned genes (according to the Gene Id) which are exogenously expressed in the plants are provided in Table 3 above.

TABLE 83

Rosette Area [cm^2]
80 mM NaCl, Day 3 from planting

| Gene Id | LSM | Significance* | LSM best Event | Significance* | % improvement of Best event |
|---|---|---|---|---|---|
| GUI | 0.73 | B | 0.73 | B | |
| MAB1 | 0.77 | B | 0.91 | A | 25 |

LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 84

Rosette Area [cm^2]
80 mM NaCl, Day 5 from planting

| Gene Id | LSM | Significance | LSM of Best event | Significance | % improvement of best event |
|---|---|---|---|---|---|
| GUI | 1.41 | B | 1.41 | B | |
| MAB1 | 1.62 | A* | 2.02 | A | 44 |
| MAB17 | 1.14 | B | 1.80 | A | 28 |

Table 84;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 85

Rosette Area [cm^2]
80 mM NaCl, Day 8 from planting

| Gene Id | LSM | Significance | LSM of Best event | Significance | % improvement of best event |
|---|---|---|---|---|---|
| GUI | 2.37 | B | 2.37 | B | |
| MAB1 | 2.59 | B | 3.56 | A | 50 |
| MAB13 | 2.45 | B | 3.44 | A | 45 |
| MAB17 | 1.96 | C | 3.10 | A | 31 |

Table 85;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 86

Rosette Area [cm^2]
80 mM NaCl, Day 10 from planting

| Gene Id | LSM | Significance | LSM of Best event | Significance | % improvement of best event |
|---|---|---|---|---|---|
| GUI | 4.67 | B | 4.67 | B | |
| MAB1 | 5.37 | A* | 7.93 | A | 70 |
| MAB15 | 4.78 | B | 6.08 | A | 30 |
| MAB17 | 4.02 | B | 6.19 | A | 32 |
| MAB3_GA | 4.39 | B | 6.07 | A | 30 |

Table 86;
LSM = Least square mean;
% improvement = compare to control (GUI);
A meaning significant different at $P < 0.05$, A* meaning significant different at $P < 0.1$.
The SEQ ID NOs. of the cloned genes (according to the Gene Id) which are exogenously expressed in the plants are provided in Table 3 above.

Tables 87-96 depict analyses of Rosette Diameter in plants overexpressing the polynucleotides of the invention under the regulation of 6669 promoter. Each Table represents an independent experiment, using 4 independent events per gene. Genes not connected by same letter as the control (A, B,) are significantly different from the control.

TABLE 87

Rosette Diameter [cm]
80 mM NaCl, Day 3 from planting

| Gene Id | LSM | Significance | LSM of Best event | Significance | % improvement of best event |
|---|---|---|---|---|---|
| GUI | 1.50 | B | 1.50 | B | |
| MAB50 | 1.35 | B | 1.80 | A | 20 |

Table 87;
LSM = Least square mean;
% improvement = compare to control (GUI);
A meaning significant different at $P < 0.05$, A* meaning significant different at $P < 0.1$.
The SEQ ID NOs. of the cloned genes (according to the Gene Id) which are exogenously expressed in the plants are provided in Table 3 above.

TABLE 88

Rosette Diameter [cm]
80 mM NaCl Day 5 from planting

| Gene Id | LSM | Significance | LSM of Best event | Significance | % improvement of best event |
|---|---|---|---|---|---|
| GUI | 2.05 | B | 2.05 | B | |
| MAB50 | 1.82 | C | 2.44 | A | 19 |

Table 88;
LSM = Least square mean;
% improvement = compare to control (GUI);
A meaning significant different at $P < 0.05$, A* meaning significant different at $P < 0.1$.
The SEQ ID NOs. of the cloned genes (according to the Gene Id) which are exogenously expressed in the plants are provided in Table 3 above.

TABLE 89

Rosette Diameter [cm]
80 mM NaCl Day 8 from planting

| Gene Id | LSM | Significance | LSM of Best event | Significance | % improvement of best event |
|---|---|---|---|---|---|
| GUI | 3.23 | B | 3.23 | B | |
| MAB50 | 3.16 | B | 4.12 | A | 27 |

Table 89;
LSM = Least square mean;
% improvement = compare to control (GUI);
A meaning significant different at $P < 0.05$, A* meaning significant different at $P < 0.1$.
The SEQ ID NOs. of the cloned genes (according to the Gene Id) which are exogenously expressed in the plants are provided in Table 3 above.

TABLE 90

Rosette Diameter [cm]
80 mM NaCl Day 10 from planting

| Gene Id | LSM | Significance | LSM of Best event | Significance | % improvement of best event |
|---|---|---|---|---|---|
| GUI | 4.47 | B | 4.47 | B | |
| MAB50 | 4.20 | B | 5.31 | A | 19 |

Table 90;
LSM = Least square mean;
% improvement = compare to control (GUI);
A meaning significant different at $P < 0.05$, A* meaning significant different at $P < 0.1$.
The SEQ ID NOs. of the cloned genes (according to the Gene Id) which are exogenously expressed in the plants are provided in Table 3 above.

TABLE 91

Rosette Diameter [cm]
80 mM NaCl Day 3 from planting

| Gene Id | LSM | Significance | LSM of Best event | Significance | % improvement of best event |
|---|---|---|---|---|---|
| GUI | 2.25 | B | 2.25 | B | |
| MAB1 | 2.60 | A | 2.78 | A | 23 |

Table 91;
LSM = Least square mean;
% improvement = compare to control (GUI);
A meaning significant different at $P < 0.05$, A* meaning significant different at $P < 0.1$.
The SEQ ID NOs. of the cloned genes (according to the Gene Id) which are exogenously expressed in the plants are provided in Table 3 above.

TABLE 92

Rosette Diameter [cm]
80 mM NaCl Day 5 from planting

| Gene Id | LSM | Significance | LSM of Best event | Significance | % improvement of best event |
|---|---|---|---|---|---|
| GUI | 2.87 | B | 2.87 | B | |
| MAB1 | 3.27 | A* | 9.25 | A | 223 |

TABLE 92-continued

Rosette Diameter [cm]
80 mM NaCl Day 5 from planting

| Gene Id | LSM | Significance | LSM of Best event | Significance | % improvement of best event |
|---|---|---|---|---|---|
| MAB20 | 2.63 | B | 9.69 | A | 238 |
| MAB6 | 2.51 | B | 10.00 | A | 249 |

Table 92;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 93

Rosette Diameter [cm]
80 mM NaCl Day 8 from planting

| Gene Id | LSM | Significance | LSM of Best event | Significance | % improvement of best event |
|---|---|---|---|---|---|
| GUI | 4.90 | B | 4.90 | B | |
| MAB6 | 4.35 | B | 6.26 | A | 28 |

Table 93;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 94

Rosette Diameter [cm]
80 mM NaCl Day 5 from planting

| Gene Id | LSM | Significance | LSM of Best event | Significance | % improvement of best event |
|---|---|---|---|---|---|
| GUI | 2.05 | B | 2.05 | B | |
| MAB1 | 2.22 | B | 2.55 | A | 25 |

Table 94;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 95

Rosette Diameter [cm]
80 mM NaCl Day 8 from planting

| Gene Id | LSM | Significance | LSM of Best event | Significance | % improvement of best event |
|---|---|---|---|---|---|
| GUI | 2.56 | B | 2.56 | B | |
| MAB1 | 2.78 | B | 3.29 | A | 29 |
| MAB3_GA | 2.56 | B | 3.04 | A | 19 |

Table 95;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 96

Rosette Diameter [cm]
80 mM NaCl Day 10 from planting

| Gene Id | LSM | Significance | LSM of Best event | Significance | % improvement of best event |
|---|---|---|---|---|---|
| GUI | 3.52 | B | 3.52 | B | |
| MAB1 | 3.79 | B | 4.76 | A | 35 |
| MAB17 | 3.24 | B | 4.14 | A | 17 |
| MAB3_GA | 3.44 | B | 4.12 | A | 17 |

Table 96;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

Tables 97-105 depict analyses of Leaf Average Area in plants overexpressing the polynucleotides of the invention under the regulation of 6669 promoter. Each Table represents an independent experiment, using 4 independent events per gene. Genes not connected by same letter as the control (A, B,) are significantly different from the control.

TABLE 97

Leaf Average Area [cm^2]
80 mM NaCl Day 3 from planting

| Gene Id | LSM | Significance | LSM of Best event | Significance | % improvement of best event |
|---|---|---|---|---|---|
| GUI | 0.10 | B | 0.10 | B | |
| MAB25 | 0.10 | B | 0.13 | A | 30 |

Table 97;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 98

Leaf Average Area [cm^2]
80 mM NaCl Day 5 from planting

| Gene Id | LSM | Significance | LSM of Best event | Significance | % improvement of best event |
|---|---|---|---|---|---|
| GUI | 0.16 | B | 0.16 | B | |
| MAB50 | 0.15 | B | 0.23 | A | 45 |

Table 98;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 99

Leaf Average Area [cm^2]
80 mM NaCl, Day 8 from planting

| Gene Id | LSM | Significance | LSM of Best event | Significance | % improvement of best event |
|---|---|---|---|---|---|
| GUI | 0.45 | B | 0.45 | B | |
| MAB50 | 0.41 | B | 0.61 | A | 34 |

Table 99;
LSM = Least square mean;
% improvement = compare to control (GUI);
A meaning significant different at P < 0.05, A* meaning significant different at P < 0.1. The SEQ ID NOs. of the cloned genes (according to the Gene Id) which are exogenously expressed in the plants are provided in Table 3 above.

TABLE 100

Leaf Average Area [cm^2]
80 mM NaCl, Day 10 from planting

| Gene Id | LSM | Significance | LSM of Best event | Significance | % improvement of best event |
|---|---|---|---|---|---|
| GUI | 0.74 | B | 0.74 | B | |
| MAB50 | 0.66 | B | 0.92 | A | 25 |

Table 100;
LSM = Least square mean;
% improvement = compare to control (GUI);
A meaning significant different at P < 0.05, A* meaning significant different at P < 0.1. The SEQ ID NOs. of the cloned genes (according to the Gene Id) which are exogenously expressed in the plants are provided in Table 3 above.

TABLE 101

Leaf Average Area [cm^2]
80 mM NaCl, Day 3 from planting

| Gene Id | LSM | Significance | LSM of Best event | Significance | % improvement of best event |
|---|---|---|---|---|---|
| GUI | 0.20 | B | 0.20 | B | |
| MAB1 | 0.25 | A | 0.28 | A | 43 |
| MAB6 | 0.18 | B | 0.30 | A | 51 |
| MAB7 | 0.23 | B | 0.27 | A | 36 |

Table 101;
LSM = Least square mean;
% improvement = compare to control (GUI);
A meaning significant different at P < 0.05, A* meaning significant different at P < 0.1. The SEQ ID NOs. of the cloned genes (according to the Gene Id) which are exogenously expressed in the plants are provided in Table 3 above.

TABLE 102

Leaf Average Area [cm^2]
80 mM NaCl, Day 8 from planting

| Gene Id | LSM | Significance | LSM of Best event | Significance | % improvement of best event |
|---|---|---|---|---|---|
| GUI | 0.69 | B | 0.69 | B | |
| MAB1 | 0.80 | A* | 0.86 | A* | 24 |
| MAB20 | 0.62 | B | 0.87 | A | 25 |
| MAB6 | 0.59 | B | 0.99 | A | 44 |

Table 102;
LSM = Least square mean;
% improvement = compare to control (GUI);
A meaning significant different at P < 0.05, A* meaning significant different at P < 0.1. The SEQ ID NOs. of the cloned genes (according to the Gene Id) which are exogenously expressed in the plants are provided in Table 3 above.

TABLE 103

Leaf Average Area [cm^2]
80 mM NaCl, Day 5 from planting

| Gene Id | LSM | Significance | LSM of Best event | Significance | % improvement of best event |
|---|---|---|---|---|---|
| GUI | 0.20 | B | 0.20 | B | |
| MAB1 | 0.22 | B | 0.27 | A | 30 |
| MAB17 | — | — | 0.25 | A | 21 |

Table 103;
LSM = Least square mean;
% improvement = compare to control (GUI);
A meaning significant different at P < 0.05, A* meaning significant different at P < 0.1. The SEQ ID NOs. of the cloned genes (according to the Gene Id) which are exogenously expressed in the plants are provided in Table 3 above.

TABLE 104

Leaf Average Area [cm^2]
80 mM NaCl, Day 8 from planting

| Gene Id | LSM | Significance | LSM of Best event | Significance | % improvement of best event |
|---|---|---|---|---|---|
| GUI | 0.28 | B | 0.28 | B | |
| MAB1 | 0.30 | B | 0.37 | A | 33 |
| MAB17 | 0.24 | B | 0.34 | A | 22 |

Table 104;
LSM = Least square mean;
% improvement = compare to control (GUI);
A meaning significant different at P < 0.05, A* meaning significant different at P < 0.1. The SEQ ID NOs. of the cloned genes (according to the Gene Id) which are exogenously expressed in the plants are provided in Table 3 above.

TABLE 105

Leaf Average Area [cm^2]
80 mM NaCl, Day 10 from planting

| Gene Id | LSM | Significance | LSM of Best event | Significance | % improvement of best event |
|---|---|---|---|---|---|
| GUI | 0.49 | B | 0.49 | B | |
| MAB1 | 0.55 | B | 0.76 | A | 53 |
| MAB15 | 0.52 | B | 0.63 | A | 26 |
| MAB17 | 0.45 | B | 0.64 | A | 28 |

Table 105;
LSM = Least square mean;
% improvement = compare to control (GUI);
A meaning significant different at P < 0.05, A* meaning significant different at P < 0.1. The SEQ ID NOs. of the cloned genes (according to the Gene Id) which are exogenously expressed in the plants are provided in Table 3 above.

Tables 106-111 depict analyses of RGR Rosette Area [cm^2] of plants overexpressing the polynucleotides of the invention under the regulation of 6669 promoter. Each Table represents an independent experiment, using 4 independent events per gene. Genes not connected by same letter as the control (A, B,) are significantly different from the control.

TABLE 106

RGR of Rosette Area [cm^2]
80 mM NaCl, Day 3 from planting

| Gene Id | LSM | Significance | LSM of Best event | Significance | % improvement of best event |
|---|---|---|---|---|---|
| GUI | 0.73 | B | 0.73 | B | |
| MAB10 | 1.21 | B | 1.86 | A | 156 |
| MAB14 | 1.31 | B | 1.80 | A | 149 |

TABLE 106-continued

RGR of Rosette Area [cm^2]
80 mM NaCl, Day 3 from planting

| Gene Id | LSM | Significance | LSM of Best event | Significance | % improvement of best event |
|---|---|---|---|---|---|
| MAB2 | 1.59 | A | 2.24 | A | 208 |
| MAB20 | 1.87 | A | 2.33 | A | 221 |
| MAB25 | 1.44 | A | 1.63 | A* | 125 |
| MAB36 | 1.49 | A | 1.89 | A | 161 |
| MAB43 | 1.73 | A | 3.85 | A | 430 |
| MAB44 | 1.76 | A | 2.51 | A | 246 |
| MAB50 | 1.37 | A* | 1.57 | A* | 117 |
| MAB9 | 1.47 | A | 1.75 | A | 141 |

Table 106;

LSM = Least square mean;

% improvement = compare to control (GUI);

A meaning significant different at P < 0.05, A* meaning significant different at P < 0.1. The SEQ ID NOs. of the cloned genes (according to the Gene Id) which are exogenously expressed in the plants are provided in Table 3 above.

TABLE 107

RGR of Rosette Area [cm^2]
80 mM NaCl, Day 8 from planting

| Gene Id | LSM | Significance | LSM of Best event | Significance | % improvement of best event |
|---|---|---|---|---|---|
| GUI | 0.61 | B | 0.61 | B | |
| MAB10 | 0.75 | A* | 0.91 | A | 50 |
| MAB14 | 0.79 | A | 0.86 | B | 42 |
| MAB19 | 0.78 | A | 0.85 | A | 41 |
| MAB2 | 0.80 | A | 0.93 | A | 54 |
| MAB20 | 0.79 | A | 0.98 | A | 61 |
| MAB36 | 0.83 | A | 0.95 | A | 56 |
| MAB44 | 0.75 | A* | 0.84 | A | 38 |
| MAB50 | 0.76 | A* | 0.83 | B | 38 |
| MAB6 | 0.82 | A | 0.99 | A | 64 |
| MAB7 | 0.78 | A | 0.87 | A | 44 |
| MAB9 | 0.77 | A | 0.84 | A | 38 |

Table 107;

LSM = Least square mean;

% improvement = compare to control (GUI);

A meaning significant different at P < 0.05, A* meaning significant different at P < 0.1. The SEQ ID NOs. of the cloned genes (according to the Gene Id) which are exogenously expressed in the plants are provided in Table 3 above.

TABLE 108

RGR of Rosette Area [cm^2]
80 mM NaCl, Day 5 from planting

| Gene Id | LSM | Significance | LSM of Best event | Significance | % improvement of best event |
|---|---|---|---|---|---|
| GUI | 0.38 | B | 0.38 | B | |
| MAB6 | 0.37 | B | 0.51 | A | 33 |

Table 108;

LSM = Least square mean;

% improvement = compare to control (GUI);

A meaning significant different at P < 0.05, A* meaning significant different at P < 0.1. The SEQ ID NOs. of the cloned genes (according to the Gene Id) which are exogenously expressed in the plants are provided in Table 3 above.

TABLE 109

RGR of Rosette Area [cm^2]
80 mM NaCl, Day 3 from planting

| Gene Id | LSM | Significance | LSM of Best event | Significance | % improvement of best event |
|---|---|---|---|---|---|
| GUI | 0.88 | B | 0.88 | B | |
| MAB18 | 0.99 | A* | 1.24 | A | 41 |

Table 109;

LSM = Least square mean;

% improvement = compare to control (GUI);

A meaning significant different at P < 0.05, A* meaning significant different at P < 0.1. The SEQ ID NOs. of the cloned genes (according to the Gene Id) which are exogenously expressed in the plants are provided in Table 3 above.

TABLE 110

RGR of Rosette Area [cm^2]
80 mM NaCl, Day 5 from planting

| Gene Id | LSM | Significance | LSM of Best event | Significance | % improvement of best event |
|---|---|---|---|---|---|
| GUI | 0.47 | B | 0.47 | B | |
| MAB1 | 0.55 | A | 0.64 | A | 38 |
| MAB13 | 0.52 | A | 0.54 | A* | 16 |
| MAB17 | 0.52 | A | 0.54 | A* | 17 |
| MAB18 | 0.53 | A | 0.58 | A | 24 |
| MAB3_GA | 0.53 | A | 0.62 | A | 33 |
| MAB32 | 0.52 | A* | 0.54 | A* | 17 |
| MAB35 | 0.54 | A | 0.57 | A | 22 |
| MAB4 | 0.51 | A* | 0.51 | A* | 10 |
| MAB46 | 0.52 | A* | 0.55 | A | 19 |
| MAB146 | 0.54 | A | 0.55 | A | 19 |
| MAB99 | 0.53 | A | 0.57 | A | 23 |

Table 110;

LSM = Least square mean;

% improvement = compare to control (GUI);

A meaning significant different at P < 0.05, A* meaning significant different at P < 0.1. The SEQ ID NOs. of the cloned genes (according to the Gene Id) which are exogenously expressed in the plants are provided in Table 3 above.

TABLE 111

RGR of Rosette Area [cm^2]
80 mM NaCl, Day 3 from planting

| Gene Id | LSM | Significance | LSM of Best event | Significance | % improvement of best event |
|---|---|---|---|---|---|
| GUI | 0.49 | B | 0.49 | B | |
| MAB1 | 0.53 | B | 0.62 | A | 27 |
| MAB35 | 0.57 | A* | 0.59 | A* | 22 |
| MAB46 | 0.55 | B | 0.63 | A | 30 |

Table 111;

LSM = Least square mean;

% improvement = compare to control (GUI);

A meaning significant different at P < 0.05, A* meaning significant different at P < 0.1. The SEQ ID NOs. of the cloned genes (according to the Gene Id) which are exogenously expressed in the plants are provided in Table 3 above.

Tables 112-118 depict analyses of RGR of Rosette Diameter in plants overexpressing the polynucleotides of the invention under the regulation of 6669 promoter. Each Table represents an independent experiment, using 4 independent events per gene. Genes not connected by same letter as the control (A, B,) are significantly different from the control.

TABLE 112

RGR of Rosette Diameter [cm])
80 mM NaCl, Day 3 from planting

| Gene Id | LSM | Significance | LSM of Best event | Significance | % improvement of best event |
|---|---|---|---|---|---|
| GUI | 0.28 | B | | | |
| MAB2 | 0.41 | B | 0.80 | A | 184 |
| MAB43 | 0.46 | B | 0.83 | A | 195 |
| MAB44 | 0.40 | B | 0.73 | A | 160 |

Table 112;
LSM = Least square mean;
% improvement = compare to control (GUI);
A meaning significant different at P < 0.05, A* meaning significant different at P < 0.1. The SEQ ID NOs. of the cloned genes (according to the Gene Id) which are exogenously expressed in the plants are provided in Table 3 above.

TABLE 113

RGR of Rosette Diameter [cm])
80 mM NaCl, Day 8 from planting

| Gene Id | LSM | Significance | LSM of Best event | Significance | % improvement of best event |
|---|---|---|---|---|---|
| GUI | 0.19 | B | 0.19 | B | |
| MAB1 | 0.22 | B | 0.24 | B | 25 |
| MAB10 | 0.25 | A | 0.29 | A | 49 |
| MAB14 | 0.23 | A | 0.25 | A | 31 |
| MAB19 | 0.24 | A | 0.26 | A | 37 |
| MAB2 | 0.24 | A | 0.26 | A | 34 |
| MAB20 | 0.25 | A | 0.29 | A | 52 |
| MAB25 | 0.24 | A | 0.27 | A | 42 |
| MAB36 | 0.25 | A | 0.28 | A | 45 |
| MAB43 | 0.22 | B | 0.25 | B | 28 |
| MAB50 | 0.25 | A | 0.28 | A | 46 |
| MAB6 | 0.24 | A | 0.27 | A | 41 |
| MAB7 | 0.22 | B | 0.27 | A | 38 |
| MAB9 | 0.23 | A | 0.26 | A | 34 |

Table 113;
LSM = Least square mean;
% improvement = compare to control (GUI);
A meaning significant different at P < 0.05, A* meaning significant different at P < 0.1. The SEQ ID NOs. of the cloned genes (according to the Gene Id) which are exogenously expressed in the plants are provided in Table 3 above.

TABLE 114

RGR of Rosette Diameter [cm])
80 mM NaCl, Day 5 from planting

| Gene Id | LSM | Significance | LSM of Best event | Significance | % improvement of best event |
|---|---|---|---|---|---|
| GUI | 0.14 | B | 0.14 | B | |
| MAB10 | 0.14 | B | 0.31 | A | 122 |
| MAB20 | 0.13 | B | 0.21 | A | 49 |
| MAB25 | 0.15 | B | 0.33 | A | 138 |
| MAB9 | 0.15 | B | 0.20 | A | 45 |

Table 114;
LSM = Least square mean;
% improvement = compare to control (GUI);
A meaning significant different at P < 0.05, A* meaning significant different at P < 0.1. The SEQ ID NOs. of the cloned genes (according to the Gene Id) which are exogenously expressed in the plants are provided in Table 3 above.

TABLE 115

RGR of Rosette Diameter [cm])
80 mM NaCl, Day 8 from planting

| Gene Id | LSM | Significance | LSM of Best event | Significance | % improvement of best event |
|---|---|---|---|---|---|
| GUI | 0.21 | B | 0.21 | B | |
| MAB20 | 0.23 | B | 0.34 | A | 67 |
| MAB9 | 0.22 | B | 0.44 | A | 114 |

Table 115;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 116

RGR of Rosette Diameter [cm])
80 mM NaCl, Day 3 from planting

| Gene Id | LSM | Significance | LSM of Best event | Significance | % improvement of best event |
|---|---|---|---|---|---|
| GUI | 0.34 | B | 0.34 | B | |
| MAB18 | 0.37 | B | 0.46 | A | 35 |
| MAB3_GA | 0.34 | B | 0.43 | A | 26 |
| MAB35 | 0.43 | A | 0.55 | A | 62 |
| MAB46 | 0.39 | B | 0.49 | A | 42 |
| MAB99 | 0.34 | B | 0.43 | A | 26 |

Table 116;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 117

RGR of Rosette Diameter [cm])
80 mM NaCl, Day 5 from planting

| Gene Id | LSM | Significance | LSM of Best event | Significance | % improvement of best event |
|---|---|---|---|---|---|
| GUI | 0.16 | B | 0.16 | B | |
| MAB1 | 0.22 | A | 0.26 | A | 66 |
| MAB18 | 0.20 | A* | 0.23 | A* | 44 |
| MAB46 | 0.25 | A | 0.45 | A | 185 |
| MAB146 | 0.20 | A* | 0.22 | A* | 42 |

Table 117;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 118

RGR of Rosette Diameter [cm])
80 mM NaCl, Day 8 from planting

| Gene Id | LSM | Significance | LSM of Best event | Significance | % improvement of best event |
|---|---|---|---|---|---|
| GUI | 0.08 | B | 0.08 | B | |
| MAB35 | 0.10 | B | 0.13 | A | 57 |
| MAB46 | 0.10 | B | 0.14 | A | 64 |

TABLE 118-continued

RGR of Rosette Diameter [cm])
80 mM NaCl, Day 8 from planting

| Gene Id | LSM | Significance | LSM of Best event | Significance | % improvement of best event |
|---|---|---|---|---|---|
| MAB146 | 0.10 | B | 0.14 | A | 66 |
| MAB99 | 0.10 | B | 0.13 | A | 56 |

Table 118;
LSM = Least square mean;
% improvement = compare to control (GUI);
A meaning significant different at $P < 0.05$, A* meaning significant different at $P < 0.1$.
The SEQ ID NOs. of the cloned genes (according to the Gene Id) which are exogenously expressed in the plants are provided in Table 3 above.

Tables 119-121 depict analyses of RGR of Leaf Average Area [cm^2] in plants overexpressing the polynucleotides of the invention under the regulation of 6669 promoter. Each Table represents an independent experiment, using 4 independent events per gene. Genes not connected by same letter as the control (A, B,) are significantly different from the control.

TABLE 119

RGR of Mean(Leaf Average Area [cm^2]
80 mM NaCl, Day 3 from planting

| Gene Id | LSM | Significance | LSM of Best event | Significance | % improvement of best event |
|---|---|---|---|---|---|
| GUI | 0.35 | B | 0.35 | B | |
| MAB14 | 0.34 | B | 0.63 | A | 82 |
| MAB25 | 0.44 | B | 0.83 | A | 137 |
| MAB36 | 0.43 | B | 0.77 | A | 120 |
| MAB6 | 0.24 | B | 0.70 | A | 102 |

Table 119;
LSM = Least square mean;
% improvement = compare to control (GUI);
A meaning significant different at $P < 0.05$, A* meaning significant different at $P < 0.1$.
The SEQ ID NOs. of the cloned genes (according to the Gene Id) which are exogenously expressed in the plants are provided in Table 3 above.

TABLE 120

RGR of Mean(Leaf Average Area [cm^2]
80 mM NaCl, Day 5 from planting

| Gene Id | LSM | Significance | LSM of Best event | Significance | % improvement of best event |
|---|---|---|---|---|---|
| GUI | 0.32 | B | 0.32 | B | |
| MAB10 | 0.32 | B | 0.56 | A | 74 |

Table 120;
LSM = Least square mean;
% improvement = compare to control (GUI);
A meaning significant different at $P < 0.05$, A* meaning significant different at $P < 0.1$.
The SEQ ID NOs. of the cloned genes (according to the Gene Id) which are exogenously expressed in the plants are provided in Table 3 above.

TABLE 121

RGR of Mean(Leaf Average Area [cm^2]
80 mM NaCl, Day 3 from planting

| Gene Id | LSM | Significance | LSM of Best event | Significance | % improvement of best event |
|---|---|---|---|---|---|
| GUI | 0.39 | B | 0.39 | B | |
| MAB13 | 0.41 | B | 0.57 | A | 49 |

TABLE 121-continued

RGR of Mean(Leaf Average Area [cm^2]
80 mM NaCl, Day 3 from planting

| Gene Id | LSM | Significance | LSM of Best event | Significance | % improvement of best event |
|---|---|---|---|---|---|
| MAB15 | 0.46 | A* | 0.54 | A | 40 |
| MAB17 | 0.46 | A* | 0.50 | A* | 30 |

Table 121;
LSM = Least square mean;
% improvement = compare to control (GUI);
A meaning significant different at $P < 0.05$, A* meaning significant different at $P < 0.1$.
The SEQ ID NOs. of the cloned genes (according to the Gene Id) which are exogenously expressed in the plants are provided in Table 3 above.

Table 122 depicts analyses of RGR of Leaf Average Area [cm^2] in plants overexpressing the polynucleotides of the invention under the regulation of 6669 promoter. Each Table represents an independent experiment, using 4 independent events per gene. Genes not connected by same letter as the control (A, B,) are significantly different from the control.

TABLE 122

RGR of Mean(Leaf Average Area [cm^2]
80 mM NaCl, Day 3 from planting

| Gene Id | LSM | Significance | LSM of Best event | Significance | % improvement of best event |
|---|---|---|---|---|---|
| GUI | 0.28 | B | 0.28 | B | |
| MAB2 | 0.41 | B | 0.80 | A | 184 |
| MAB43 | 0.46 | B | 0.83 | A | 195 |
| MAB44 | 0.40 | B | 0.73 | A | 160 |

Table 122;
LSM = Least square mean;
% improvement = compare to control (GUI);
A meaning significant different at $P < 0.05$, A* meaning significant different at $P < 0.1$.
The SEQ ID NOs. of the cloned genes (according to the Gene Id) which are exogenously expressed in the plants are provided in Table 3 above.

Table 123 depicts analyses of Plot Dry weight (DW) in plants overexpressing the polynucleotides of the invention under the regulation of 6669 promoter. Each Table represents an independent experiment, using 4 independent events per gene. Genes not connected by same letter as the control (A, B,) are significantly different from the control.

TABLE 123

Dry Weight [g]
80 mM NaCl

| Gene Id | LSM | Significance | LSM of Best event | Significance | % improvement of best event |
|---|---|---|---|---|---|
| GUI | 4.00 | B | 4.00 | B | |
| MAB1 | 4.92 | A | 6.40 | A | 60 |
| MAB134 | 4.35 | B | 5.35 | A | 34 |
| MAB15 | 4.42 | B | 5.57 | A | 39 |
| MAB18 | 4.52 | B | 5.35 | A | 34 |
| MAB3_GA | 4.53 | B | 5.47 | A | 37 |

Table 123;
LSM = Least square mean;
% improvement = compare to control (GUI);
A meaning significant different at $P < 0.05$, A* meaning significant different at $P < 0.1$.
The SEQ ID NOs. of the cloned genes (according to the Gene Id) which are exogenously expressed in the plants are provided in Table 3 above.

Tables 124-126 depict analyses of 1000 Seeds Weight in plants overexpressing the polynucleotides of the invention under the regulation of 6669 promoter. Each Table represents an independent experiment, using 4 independent events per gene. Genes not connected by same letter as the control (A, B,) are significantly different from the control.

TABLE 124

1000 Seeds Weight [g]
80 mM NaCl

| Gene Id | LSM | Significance | LSM of Best event | Significance | % improvement of best event |
|---|---|---|---|---|---|
| GUI | 0.02 | B | 0.02 | B | |
| MAB14 | 0.02 | B | 0.03 | A | 32 |
| MAB19 | 0.02 | B | 0.03 | A | 27 |
| MAB2 | 0.02 | B | 0.03 | A | 24 |
| MAB6 | 0.03 | A | 0.03 | A | 53 |

Table 124;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 125

1000 Seeds Weight [g]
80 mM NaCl

| Gene Id | LSM | Significance | LSM of Best event | Significance | % improvement of best event |
|---|---|---|---|---|---|
| GUI | 0.02 | B | 0.02 | B | |
| MAB20 | 0.02 | A* | 0.02 | A | 17 |
| MAB25 | 0.02 | B | 0.02 | A | 20 |
| MAB6 | 0.02 | A* | 0.02 | A | 21 |
| MAB7 | 0.02 | B | 0.02 | A | 21 |
| MAB9 | 0.02 | B | 0.02 | A | 19 |

Table 125;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 126

1000 Seeds Weight [g]
80 mM NaCl

| Gene Id | LSM | % improvement of best event | LSM of Best event | Significance | % improvement of best event |
|---|---|---|---|---|---|
| GUI | 0.02 | B | 0.02 | B | |
| MAB100 | 0.02 | B | 0.02 | A | 28 |
| MAB134 | 0.02 | B | 0.02 | A | 26 |
| MAB17 | 0.02 | B | 0.02 | A | 23 |
| MAB18 | 0.02 | B | 0.02 | A | 17 |
| MAB32 | 0.02 | B | 0.02 | A | 13 |
| MAB4 | 0.02 | B | 0.02 | A | 19 |
| MAB46 | 0.02 | B | 0.02 | A | 18 |
| MAB99 | 0.02 | B | 0.02 | A | 15 |

Table 126;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

Tables 127-129 depict analyses of Seed Yield per Plant in plants overexpressing the polynucleotides of the invention under the regulation of 6669 promoter. Each Table represents an independent experiment, using 4 independent events per gene. Genes not connected by same letter as the control (A, B,) are significantly different from the control.

TABLE 127

Seed Yield per Plant [g]
80 mM NaCl

| Gene Id | LSM | Significance | LSM of Best event | Significance | % improvement of best event |
|---|---|---|---|---|---|
| GUI | 0.07 | B | 0.07 | B | |
| MAB44 | 0.11 | B | 0.22 | A | 210 |
| MAB50 | 0.11 | B | 0.19 | A | 170 |

Table 127;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 128

Seed Yield per Plant [g]
80 mM NaCl

| Gene Id | LSM | Significance | LSM of Best event | Significance | % improvement of best event |
|---|---|---|---|---|---|
| GUI | 0.09 | B | 0.09 | B | |
| MAB6 | 0.11 | A* | 0.21 | A | 142 |
| MAB9 | 0.09 | B | 0.14 | A | 59 |

Table 128;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 129

Seed Yield per Plant [g]
80 mM NaCl

| Gene ID | LSM | Significance | LSM of Best event | Significance | % improvement of best event |
|---|---|---|---|---|---|
| GUI | 0.14 | B | 0.14 | B | |
| MAB1 | 0.19 | A | 0.33 | A | 139 |
| MAB100 | 0.17 | B | 0.24 | A | 79 |

Table 129;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

Table 130 depicts analyses of Harvest Index in plants overexpressing the polynucleotides of the invention under the regulation of 6669 promoter. Each Table represents an independent experiment, using 4 independent events per gene. Genes not connected by same letter as the control (A, B,) are significantly different from the control.

TABLE 130

Harvest Index
80 mM NaCl

| Gene Id | LSM | Significance | LSM of Best event | Significance | % improvement of best event |
|---|---|---|---|---|---|
| GUI | 0.11 | B | 0.11 | B | |
| MAB25 | 0.16 | B | 0.26 | A | 139 |

TABLE 130-continued

Harvest Index
80 mM NaCl

| Gene Id | LSM | Significance | LSM of Best event | Significance | % improvement of best event |
|---|---|---|---|---|---|
| MAB44 | 0.20 | A* | 0.30 | A | 174 |
| MAB7 | 0.12 | B | 0.29 | A | 172 |

Table 130;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

Tables 131-140 depict analyses of Rosette Area in plants overexpressing the polynucleotides of the invention under the regulation of 6669 promoter. Each Table represents an independent experiment, using 4 independent events per gene. Genes not connected by same letter as the control (A, B,) are significantly different from the control.

TABLE 131

Rosette Area [cm^2]
Normal conditions, Day 5 from planting

| Gene Id | LSM | Significance | LSM of Best event | Significance | % improvement of best event |
|---|---|---|---|---|---|
| GUI | 1.37 | B | 1.37 | B | |
| MAB1 | 1.43 | B | 1.80 | A | 31 |
| MAB9 | 1.32 | B | 1.74 | A | 27 |

Table 131;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 132

Rosette Area [cm^2]
Normal conditions, Day 8 from planting

| Gene Id | LSM | Significance | LSM of Best event | Significance | % improvement of best event |
|---|---|---|---|---|---|
| GUI | 4.73 | B | 4.73 | B | |
| MAB1 | 4.95 | B | 6.45 | A | 36 |

Table 132;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 133

Rosette Area [cm^2]
Normal conditions, Day 10 from planting

| Gene Id | LSM | Significance | LSM of Best event | Significance | % improvement of best event |
|---|---|---|---|---|---|
| GUI | 8.45 | B | 8.45 | B | |
| MAB1 | 8.87 | B | 11.11 | A | 31 |

Table 133;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 134

Rosette Area [cm^2]
Normal conditions, Day 3 from planting

| Gene Id | LSM | Significance | LSM of Best event | Significance | % improvement of best event |
|---|---|---|---|---|---|
| GUI | 1.65 | B | 1.65 | B | |
| MAB1 | 2.09 | A | 2.27 | A | 37 |
| MAB36 | 1.65 | B | 2.58 | A | 56 |
| MAB7 | 1.83 | B | 2.81 | A | 70 |

Table 134;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 135

Rosette Area [cm^2]
Normal conditions, Day 5 from planting

| Gene Id | LSM | Significance | LSM of Best event | Significance | % improvement of best event |
|---|---|---|---|---|---|
| GUI | 2.93 | B | 2.93 | B | |
| MAB1 | 3.60 | A* | 3.78 | A* | 29 |
| MAB36 | 2.91 | B | 4.55 | A | 55 |
| MAB7 | 3.14 | B | 4.69 | A | 60 |

Table 135;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 136

Rosette Area [cm^2]
Normal conditions, Day 8 from planting

| Gene Id | LSM | Significance | LSM of Best event | Significance | % improvement of best event |
|---|---|---|---|---|---|
| GUI | 7.73 | B | 7.73 | B | |
| MAB1 | 9.77 | A | 10.58 | A | 37 |
| MAB36 | 8.05 | B | 12.12 | A | 57 |
| MAB7 | 8.69 | B | 12.82 | A | 66 |

Table 136;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 137

Rosette Area [cm^2]
Normal conditions, Day 3 from planting

| Gene Id | LSM | Significance | LSM of Best event | Significance | % improvement of best event |
|---|---|---|---|---|---|
| GUI | 0.55 | B | 0.55 | B | |
| MAB1 | 0.58 | B | 0.81 | A | 47 |
| MAB100 | 0.60 | B | 0.74 | A | 34 |

TABLE 137-continued

Rosette Area [cm^2]
Normal conditions, Day 3 from planting

| Gene Id | LSM | Significance | LSM of Best event | Significance | % improvement of best event |
|---|---|---|---|---|---|
| MAB15 | 0.65 | A* | 0.90 | A | 64 |
| MAB17 | 0.55 | B | 0.85 | A | 55 |

Table 137;
LSM = Least square mean;
% improvement = compare to control (GUI);
A meaning significant different at $P < 0.05$, A* meaning significant different at $P < 0.1$.
The SEQ ID NOs. of the cloned genes (according to the Gene Id) which are exogenously expressed in the plants are provided in Table 3 above.

TABLE 138

Rosette Area [cm^2]
Normal conditions, Day 5 from planting

| Gene Id | LSM | Significance | LSM of Best event | Significance | % improvement of best event |
|---|---|---|---|---|---|
| GUI | 1.03 | B | 1.03 | B | |
| MAB1 | 1.17 | B | 1.54 | A | 49 |
| MAB100 | 1.18 | B | 1.46 | A | 42 |
| MAB15 | 1.23 | A | 1.67 | A | 62 |
| MAB17 | 1.01 | B | 1.59 | A | 54 |

Table 138;
LSM = Least square mean;
% improvement = compare to control (GUI);
A meaning significant different at $P < 0.05$, A* meaning significant different at $P < 0.1$.
The SEQ ID NOs. of the cloned genes (according to the Gene Id) which are exogenously expressed in the plants are provided in Table 3 above.

TABLE 139

Rosette Area [cm^2]
Normal conditions, Day 8 from planting

| Gene Id | LSM | Significance | LSM of Best event | Significance | % improvement of best event |
|---|---|---|---|---|---|
| GUI | 2.09 | B | 2.09 | B | |
| MAB1 | 2.46 | B | 3.43 | A | 64 |
| MAB100 | 2.29 | B | 2.81 | A | 34 |
| MAB15 | 2.60 | A | 3.63 | A | 73 |
| MAB17 | 2.06 | B | 3.35 | A | 60 |

Table 139;
LSM = Least square mean;
% improvement = compare to control (GUI);
A meaning significant different at $P < 0.05$, A* meaning significant different at $P < 0.1$.
The SEQ ID NOs. of the cloned genes (according to the Gene Id) which are exogenously expressed in the plants are provided in Table 3 above.

TABLE 140

Rosette Area [cm^2]
Normal conditions, Day 10 from planting

| Gene Id | LSM | Significance | LSM of Best event | Significance | % improvement of best event |
|---|---|---|---|---|---|
| GUI | 4.81 | B | 4.81 | B | |
| MAB1 | 5.57 | A* | 8.29 | A | 72 |
| MAB15 | 5.72 | A | 8.05 | A | 67 |
| MAB17 | 4.78 | B | 7.50 | A | 56 |

Table 140;
LSM = Least square mean;
% improvement = compare to control (GUI);
A meaning significant different at $P < 0.05$, A* meaning significant different at $P < 0.1$.
The SEQ ID NOs. of the cloned genes (according to the Gene Id) which are exogenously expressed in the plants are provided in Table 3 above.

Tables 141-148 depict analyses of Rosette Diameter in plants overexpressing the polynucleotides of the invention under the regulation of 6669 promoter. Each Table represents an independent experiment, using 4 independent events per gene. Genes not connected by same letter as the control (A, B,) are significantly different from the control.

TABLE 141

Rosette Area [cm]
Normal conditions, Day 8 from planting

| Gene Id | LSM | Significance | LSM of Best event | Significance | % improvement of best event |
|---|---|---|---|---|---|
| GUI | 3.52 | B | 3.52 | B | |
| MAB1 | 3.58 | B | 4.17 | A | 18 |

Table 141;
LSM = Least square mean;
% improvement = compare to control (GUI);
A meaning significant different at $P < 0.05$, A* meaning significant different at $P < 0.1$.
The SEQ ID NOs. of the cloned genes (according to the Gene Id) which are exogenously expressed in the plants are provided in Table 3 above.

TABLE 142

Rosette Area [cm]
Normal conditions, Day 3 from planting

| Gene Id | LSM | Significance | LSM of Best event | Significance | % improvement of best event |
|---|---|---|---|---|---|
| GUI | 2.28 | B | 2.28 | B | |
| MAB36 | 2.23 | B | 2.91 | A | 28 |
| MAB7 | 2.47 | B | 3.11 | A | 36 |

Table 142;
LSM = Least square mean;
% improvement = compare to control (GUI);
A meaning significant different at $P < 0.05$, A* meaning significant different at $P < 0.1$.
The SEQ ID NOs. of the cloned genes (according to the Gene Id) which are exogenously expressed in the plants are provided in Table 3 above.

TABLE 143

Rosette Area [cm]
Normal conditions, Day 5 from planting

| Gene Id | LSM | Significance | LSM of Best event | Significance | % improvement of best event |
|---|---|---|---|---|---|
| GUI | 2.99 | B | 2.99 | B | |
| MAB7 | 3.24 | B | 4.08 | A | 36 |

Table 143;
LSM = Least square mean;
% improvement = compare to control (GUI);
A meaning significant different at $P < 0.05$, A* meaning significant different at $P < 0.1$.
The SEQ ID NOs. of the cloned genes (according to the Gene Id) which are exogenously expressed in the plants are provided in Table 3 above.

TABLE 144

Rosette Diameter [cm]
Normal conditions, Day 8 from planting

| Gene Id | LSM | Significance | LSM of Best event | Significance | % improvement of best event |
|---|---|---|---|---|---|
| GUI | 5.00 | B | 5.00 | B | |
| MAB1 | 5.65 | A* | 5.87 | A* | 17 |
| MAB7 | 5.06 | B | 6.32 | A | 26 |

Table 144;
LSM = Least square mean;
% improvement = compare to control (GUI);
A meaning significant different at $P < 0.05$, A* meaning significant different at $P < 0.1$.
The SEQ ID NOs. of the cloned genes (according to the Gene Id) which are exogenously expressed in the plants are provided in Table 3 above.

TABLE 145

Rosette Diameter [cm]
Normal conditions, Day 3 from planting

| Gene Id | LSM | Significance | LSM of Best event | Significance | % improvement of best event |
|---|---|---|---|---|---|
| GUI | 1.30 | B | 1.30 | B | |
| MAB15 | 1.48 | A | 1.69 | A | 30 |
| MAB17 | 1.33 | B | 1.60 | A | 23 |

Table 145;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 146

Rosette Diameter [cm]
Normal conditions, Day 5 from planting

| Gene Id | LSM | Significance | LSM of Best event | Significance | % improvement of best event |
|---|---|---|---|---|---|
| GUI | 1.87 | B | 1.87 | B | |
| MAB1 | 1.86 | B | 2.21 | A | 18 |
| MAB15 | 1.96 | B | 2.29 | A | 22 |
| MAB17 | 1.78 | B | 2.26 | A | 21 |

Table 146;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 147

Rosette Diameter [cm]
Normal conditions, Day 8 from planting

| Gene Id | LSM | Significance | LSM of Best event | Significance | % improvement of best event |
|---|---|---|---|---|---|
| GUI | 2.49 | B | | | |
| MAB1 | 2.60 | B | 3.14 | A | 26 |
| MAB15 | 2.64 | B | 3.17 | A | 27 |
| MAB17 | 2.39 | B | 3.09 | A | 24 |

Table 147;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 148

Rosette Diameter [cm]
Normal conditions, Day 10 from planting

| Gene Id | LSM | Significance | LSM of Best event | Significance | % improvement of best event |
|---|---|---|---|---|---|
| GUI | 3.49 | B | 3.49 | B | |
| MAB1 | 3.88 | A* | 4.81 | A | 38 |
| MAB15 | 3.78 | B | 4.52 | A | 29 |
| MAB17 | 3.53 | B | 4.45 | A | 27 |

Table 148;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

Tables 149-157 depict analyses of Leaf Average Area in plants overexpressing the polynucleotides of the invention under the regulation of 6669 promoter. Each Table represents an independent experiment, using 4 independent events per gene. Genes not connected by same letter as the control (A, B,) are significantly different from the control.

TABLE 149

Leaf Average [cm^2]
Normal conditions, Day 5 from planting

| Gene Id | LSM | Significance | LSM of Best event | Significance | % improvement of best event |
|---|---|---|---|---|---|
| GUI | 0.17 | B | 0.17 | B | |
| MAB1 | 0.17 | B | 0.21 | A | 27 |

Table 149;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 150

Leaf Average [cm^2]
Normal conditions, Day 8 from planting

| Gene Id | LSM | Significance | LSM of Best event | Significance | % improvement of best event |
|---|---|---|---|---|---|
| GUI | 0.51 | B | 0.51 | B | |
| MAB1 | 0.52 | B | 0.69 | A | 35 |

Table 150;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 151

Leaf Average [cm^2]
Normal conditions, Day 3 from planting

| Gene Id | LSM | Significance | LSM of Best event | Significance | % improvement of best event |
|---|---|---|---|---|---|
| GUI | 0.19 | B | 0.19 | B | |
| MAB1 | 0.25 | A | 0.27 | A | 38 |
| MAB36 | 0.20 | B | 0.31 | A | 58 |
| MAB7 | 0.23 | A* | 0.33 | A | 67 |

Table 151;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 152

Leaf Average [cm^2]
Normal conditions, Day 5 from planting

| Gene Id | LSM | Significance | LSM of Best event | Significance | % improvement of best event |
|---|---|---|---|---|---|
| GUI | 0.32 | B | 0.32 | B | |
| MAB1 | 0.38 | B | 0.43 | A | 34 |
| MAB36 | 0.32 | B | 0.46 | A | 43 |
| MAB7 | 0.33 | B | 0.47 | A | 45 |

Table 152;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 153

Leaf Average [cm^2]
Normal conditions, Day 8 from planting

| Gene Id | LSM | Significance | LSM of Best event | Significance | % improvement of best event |
|---|---|---|---|---|---|
| GUI | 0.69 | B | 0.69 | B | |
| MAB36 | 0.69 | B | 0.93 | A | 36 |
| MAB7 | 0.79 | B | 1.17 | A | 71 |

Table 153;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 154

Leaf Average [cm^2]
Normal conditions, Day 3 from planting

| Gene Id | LSM | Significance | LSM of Best event | Significance | % improvement of best event |
|---|---|---|---|---|---|
| GUI | 0.11 | B | 0.11 | B | |
| MAB1 | 0.12 | B | 0.15 | A | 28 |
| MAB15 | 0.13 | B | 0.17 | A | 53 |
| MAB17 | 0.11 | B | 0.15 | A | 34 |

Table 154;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 155

Leaf Average [cm^2]
Normal conditions, Day 5 from planting

| Gene Id | LSM | Significance | LSM of Best event | Significance | % improvement of best event |
|---|---|---|---|---|---|
| GUI | 0.16 | B | 0.16 | B | |
| MAB1 | 0.17 | B | 0.21 | A | 26 |
| MAB100 | 0.18 | B | 0.21 | A | 30 |
| MAB15 | 0.18 | A* | 0.23 | A | 39 |
| MAB17 | 0.16 | B | 0.22 | A | 35 |

Table 155;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 156

Leaf Average [cm^2]
Normal conditions, Day 8 from planting

| Gene Id | LSM | Significance | LSM of Best event | Significance | % improvement of best event |
|---|---|---|---|---|---|
| GUI | 0.24 | B | 0.24 | B | |
| MAB1 | 0.28 | A* | 0.37 | A | 50 |
| MAB15 | 0.29 | A* | 0.37 | A | 53 |
| MAB17 | 0.25 | B | 0.34 | A | 40 |

Table 156;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 157

Leaf Average [cm^2]
Normal conditions, Day 10 from planting

| Gene Id | LSM | Significance | LSM of Best event | Significance | % improvement of best event |
|---|---|---|---|---|---|
| GUI | 0.54 | B | 0.54 | B | |
| MAB1 | 0.57 | B | 0.80 | A | 49 |
| MAB15 | 0.59 | B | 0.78 | A | 45 |
| MAB17 | 0.51 | B | 0.74 | A | 37 |

Table 157;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

Tables 158-166 depict analyses of RGR Rosette Area [cm^2] of plants overexpressing the polynucleotides of the invention under the regulation of 6669 promoter. Each Table represents an independent experiment, using 4 independent events per gene. Genes not connected by same letter as the control (A, B,) are significantly different from the control.

TABLE 158

RGR of Rosette Area [cm^2]
Normal conditions, Day 3 from planting

| Gene Id | LSM | Significance | LSM of Best event | Significance | % improvement of best event |
|---|---|---|---|---|---|
| GUI | 1.73 | B | 1.73 | B | |
| MAB20 | 2.18 | B | 3.62 | A | 109 |
| MAB43 | 2.04 | B | 3.80 | A | 119 |
| MAB50 | 2.25 | B | 3.81 | A | 120 |

Table 158;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 159

RGR of Rosette Area [cm^2]
Normal conditions, Day 5 from planting

| Gene Id | LSM | Significance | LSM of Best event | Significance | % improvement of best event |
|---|---|---|---|---|---|
| GUI | 0.48 | B | 0.48 | B | |
| MAB2 | 0.58 | A* | 0.70 | A | 45 |
| MAB43 | 0.62 | A | 0.75 | A | 56 |
| MAB6 | 0.52 | B | 0.72 | A | 50 |

Table 159;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 160

RGR of Rosette Area [cm^2]
Normal conditions, Day 8 from planting

| Gene Id | LSM | Significance | LSM of Best event | Significance | % improvement of best event |
|---|---|---|---|---|---|
| GUI | 0.84 | B | 0.84 | B | |
| MAB50 | 0.87 | B | 0.99 | A | 18 |
| MAB6 | 0.87 | B | 1.06 | A | 26 |

Table 160;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 161

RGR of Rosette Area [cm^2]
Normal conditions, Day 10 from planting

| Gene Id | LSM | Significance | LSM of Best event | Significance | % improvement of best event |
|---|---|---|---|---|---|
| GUI | 0.39 | B | 0.39 | B | |
| MAB10 | 0.44 | B | 0.54 | A | 37 |
| MAB36 | 0.45 | B | 0.51 | A | 30 |
| MAB50 | 0.45 | A* | 0.53 | A | 35 |
| MAB6 | 0.44 | B | 0.60 | A | 51 |
| MAB7 | 0.43 | B | 0.50 | A | 27 |

Table 161;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 162

RGR of Rosette Area [cm^2]
Normal conditions, Day 5 from planting

| Gene Id | LSM | Significance | LSM of Best event | Significance | % improvement of best event |
|---|---|---|---|---|---|
| GUI | 0.39 | B | 0.39 | B | |
| MAB20 | 0.38 | B | 0.50 | A | 28 |
| MAB25 | 0.39 | B | 0.53 | A | 38 |

Table 162;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 163

RGR of Rosette Area [cm^2]
Normal conditions, Day 8 from planting

| Gene Id | LSM | Significance | LSM of Best event | Significance | % improvement of best event |
|---|---|---|---|---|---|
| GUI | 0.55 | B | 0.55 | B | |
| MAB10 | 0.64 | A* | 0.71 | A* | 30 |
| MAB2 | 0.63 | A* | 0.70 | A | 28 |
| MAB20 | 0.63 | A* | 0.67 | A* | 21 |
| MAB25 | 0.64 | A | 0.73 | A | 32 |
| MAB44 | 0.65 | A | 0.77 | A | 41 |
| MAB50 | 0.70 | A | 0.83 | A | 51 |
| MAB6 | 0.63 | A* | 0.81 | A | 48 |
| MAB7 | 0.61 | B | 0.73 | A | 34 |
| MAB9 | 0.60 | B | 0.69 | A | 26 |

Table 163;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 164

RGR of Rosette Area [cm^2]
Normal conditions, Day 5 from planting

| Gene Id | LSM | Significance | LSM of Best event | Significance | % improvement of best event |
|---|---|---|---|---|---|
| GUI | 0.45 | B | 0.45 | B | |
| MAB13 | 0.63 | A | 0.68 | A* | 49 |
| MAB32 | 0.50 | B | 0.74 | A | 64 |
| MAB46 | 0.52 | B | 0.75 | A | 65 |
| MAB146 | 0.64 | A | 0.88 | A | 94 |
| MAB99 | 0.52 | B | 0.73 | A | 61 |

Table 164;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 165

RGR of Rosette Area [cm^2]
Normal conditions, Day 8 from planting

| Gene Id | LSM | Significance | LSM of Best event | Significance | % improvement of best event |
|---|---|---|---|---|---|
| GUI | 0.34 | B | 0.34 | B | |
| MAB1 | 0.36 | B | 0.45 | A | 31 |
| MAB99 | 0.33 | B | 0.43 | A | 28 |

Table 165;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 166

RGR of Rosette Area [cm^2]
Normal conditions, Day 10 from planting

| Gene Id | LSM | Significance | LSM of Best event | Significance | % improvement of best event |
|---|---|---|---|---|---|
| GUI | 0.66 | B | 0.66 | B | |
| MAB13 | 0.73 | B | 0.81 | A | 23 |
| MAB3_GA | 0.70 | B | 0.85 | A | 29 |

TABLE 166-continued

RGR of Rosette Area [cm^2]
Normal conditions, Day 10 from planting

| Gene Id | LSM | Signifi-cance | LSM of Best event | Signifi-cance | % improvement of best event |
|---|---|---|---|---|---|
| MAB32 | 0.70 | B | 0.86 | A | 31 |
| MAB99 | 0.68 | B | 0.82 | A | 25 |

Table 166;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

Tables 167-175 depict analyses of RGR of Rosette Diameter in plants overexpressing the polynucleotides of the invention under the regulation of 6669 promoter. Each Table represents an independent experiment, using 4 independent events per gene. Genes not connected by same letter as the control (A, B,) are significantly different from the control.

TABLE 167

RGR of Rosette Diameter [cm])
Normal conditions, Day 3 from planting

| Gene Id | LSM | Signifi-cance | LSM of Best event | Signifi-cance | % improvement of best event |
|---|---|---|---|---|---|
| GUI | 0.43 | B | 0.43 | B | |
| MAB50 | 0.70 | A* | 1.50 | A | 251 |
| MAB6 | 0.45 | B | 1.21 | A | 183 |

Table 167;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 168

RGR of Rosette Diameter [cm])
Normal conditions, Day 5 from planting

| Gene Id | LSM | Signifi-cance | LSM of Best event | Signifi-cance | % improvement of best event |
|---|---|---|---|---|---|
| GUI | 0.16 | B | 0.16 | B | |
| MAB10 | 0.19 | A* | 0.21 | A* | 28 |
| MAB19 | 0.20 | A | 0.23 | A | 45 |
| MAB36 | 0.18 | B | 0.21 | A | 32 |
| MAB50 | 0.17 | B | 0.23 | A | 42 |
| MAB6 | 0.18 | B | 0.25 | A | 57 |
| MAB7 | 0.18 | B | 0.24 | A | 52 |

Table 168;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 169

RGR of Rosette Diameter [cm])
Normal conditions, Day 8 from planting

| Gene Id | LSM | Signifi-cance | LSM of Best event | Signifi-cance | % improvement of best event |
|---|---|---|---|---|---|
| GUI | 0.25 | B | 0.25 | B | |
| MAB10 | 0.28 | A | 0.30 | A | 19 |
| MAB14 | 0.27 | B | 0.31 | A | 23 |
| MAB19 | 0.28 | A | 0.32 | A | 29 |
| MAB2 | 0.27 | B | 0.30 | A | 21 |
| MAB20 | 0.27 | B | 0.29 | A | 18 |
| MAB36 | 0.27 | A* | 0.32 | A | 28 |
| MAB43 | 0.25 | B | 0.26 | B | 5 |
| MAB44 | 0.26 | B | 0.30 | A | 21 |
| MAB50 | 0.27 | B | 0.30 | A | 21 |
| MAB7 | 0.28 | A* | 0.29 | A | 17 |
| MAB9 | 0.27 | A* | 0.30 | A | 20 |

Table 169;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 170

RGR of Rosette Diameter [cm])
Normal conditions, Day 10 from planting

| Gene Id | LSM | Signifi-cance | LSM of Best event | Signifi-cance | % improvement of best event |
|---|---|---|---|---|---|
| GUI | 0.17 | B | 0.17 | B | |
| MAB19 | 0.19 | A* | 0.23 | A | 31 |
| MAB2 | 0.20 | A | 0.23 | A | 32 |
| MAB20 | 0.19 | A | 0.23 | A | 33 |
| MAB43 | 0.19 | B | 0.21 | A | 24 |
| MAB44 | 0.18 | B | 0.22 | A | 25 |
| MAB50 | 0.20 | A | 0.23 | A | 32 |
| MAB6 | 0.19 | A* | 0.24 | A | 42 |
| MAB9 | 0.18 | B | 0.21 | A | 25 |

Table 170;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 171

RGR of Rosette Diameter [cm])
Normal conditions, Day 5 from planting

| Gene Id | LSM | Signifi-cance | LSM of Best event | Signifi-cance | % improvement of best event |
|---|---|---|---|---|---|
| GUI | 0.16 | B | 0.16 | B | |
| MAB50 | 0.19 | B | 0.22 | A | 42 |
| MAB6 | 0.15 | B | 0.24 | A | 49 |

Table 171;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 172

RGR of Rosette Diameter [cm])
Normal conditions, Day 10 from planting

| Gene Id | LSM | Significance | LSM of Best event | Significance | % improvement of best event |
|---|---|---|---|---|---|
| GUI | 0.22 | B | 0.22 | B | |
| MAB2 | 0.26 | A* | 0.28 | A | 27 |
| MAB20 | 0.26 | B | 0.30 | A | 33 |
| MAB25 | 0.26 | A* | 0.29 | A* | 31 |
| MAB43 | 0.24 | B | 0.29 | A | 29 |
| MAB44 | 0.25 | B | 0.29 | A | 31 |

Table 172;
LSM = Least square mean;
% improvement = compare to control (GUI);
A meaning significant different at $P < 0.05$, A* meaning significant different at $P < 0.1$.
The SEQ ID NOs. of the cloned genes (according to the Gene Id) which are exogenously expressed in the plants are provided in Table 3 above.

TABLE 173

RGR of Rosette Diameter [cm])
Normal conditions, Day 3 from planting

| Gene Id | LSM | Significance | LSM of Best event | Significance | % improvement of best event |
|---|---|---|---|---|---|
| GUI | 0.29 | B | 0.29 | B | |
| MAB100 | 0.37 | A* | 0.51 | a | 74 |
| MAB13 | 0.38 | A | 0.58 | A | 95 |
| MAB15 | 0.36 | A | 0.45 | A | 54 |
| MAB18 | 0.36 | A* | 0.38 | A* | 28 |
| MAB3_GA | 0.43 | A | 0.60 | A | 105 |
| MAB35 | 0.39 | A | 0.44 | A | 50 |
| MAB46 | 0.31 | B | 0.49 | A | 65 |
| MAB146 | 0.35 | A | 0.44 | A | 50 |

Table 173;
LSM = Least square mean;
% improvement = compare to control (GUI);
A meaning significant different at $P < 0.05$, A* meaning significant different at $P < 0.1$.
The SEQ ID NOs. of the cloned genes (according to the Gene Id) which are exogenously expressed in the plants are provided in Table 3 above.

TABLE 174

RGR of Rosette Diameter [cm])
Normal conditions, Day 8 from planting

| Gene Id | LSM | Significance | LSM of Best event | Significance | % improvement of best event |
|---|---|---|---|---|---|
| GUI | 0.11 | B | 0.11 | B | |
| MAB1 | 0.13 | A* | 0.16 | A | 49 |
| MAB13 | 0.13 | A* | 0.16 | A | 41 |
| MAB18 | 0.14 | A | 0.16 | A | 45 |
| MAB32 | 0.13 | B | 0.15 | A | 39 |
| MAB146 | 0.16 | A | 0.19 | A | 72 |
| MAB99 | 0.12 | B | 0.15 | A | 40 |

Table 174;
LSM = Least square mean;
% improvement = compare to control (GUI);
A meaning significant different at $P < 0.05$, A* meaning significant different at $P < 0.1$.
The SEQ ID NOs. of the cloned genes (according to the Gene Id) which are exogenously expressed in the plants are provided in Table 3 above.

TABLE 175

RGR of Rosette Diameter [cm])
Normal conditions, Day 10 from planting

| Gene Id | LSM | Significance | LSM of Best event | Significance | % improvement of best event |
|---|---|---|---|---|---|
| GUI | 0.20 | B | 0.20 | B | |
| MAB1 | 0.25 | A | 0.27 | A | 30 |
| MAB17 | 0.24 | A | 0.26 | A* | 25 |
| MAB18 | 0.25 | A | 0.31 | A | 51 |
| MAB35 | 0.25 | A | 0.28 | A | 36 |
| MAB146 | 0.25 | A | 0.28 | A | 36 |
| MAB99 | 0.24 | A | 0.29 | A | 44 |

Table 175;
LSM = Least square mean;
% improvement = compare to control (GUI);
A meaning significant different at $P < 0.05$, A* meaning significant different at $P < 0.1$.
The SEQ ID NOs. of the cloned genes (according to the Gene Id) which are exogenously expressed in the plants are provided in Table 3 above.

Tables 176-178 depict analyses of RGR of Leaf Average Area [cm^2] in plants overexpressing the polynucleotides of the invention under the regulation of 6669 promoter. Each Table represents an independent experiment, using 4 independent events per gene. Genes not connected by same letter as the control (A, B,) are significantly different from the control.

TABLE 176

RGR of Mean(Leaf Average Area [cm^2]
Normal conditions, Day 10 from planting

| Gene Id | LSM | Significance | LSM of Best event | Significance | % improvement of best event |
|---|---|---|---|---|---|
| GUI | 0.34 | B | 0.34 | B | |
| MAB10 | 0.35 | B | 0.52 | A | 56 |
| MAB36 | 0.40 | B | 0.52 | A | 55 |
| MAB7 | 0.37 | B | 0.50 | A | 49 |

Table 176;
LSM = Least square mean;
% improvement = compare to control (GUI).
The SEQ ID NOs. of the cloned genes (according to the Gene Id) which are exogenously expressed in the plants are provided in Table 3 above.

TABLE 177

RGR of Mean(Leaf Average Area [cm^2]
Normal conditions, Day 10 from planting

| Gene Id | LSM | Significance | LSM of Best event | Significance | % improvement of best event |
|---|---|---|---|---|---|
| GUI | 0.38 | B | 0.38 | B | |
| MAB10 | 0.47 | A | 0.51 | A* | 35 |
| MAB2 | 0.41 | B | 0.49 | A | 29 |
| MAB25 | 0.43 | B | 0.55 | A | 44 |
| MAB50 | 0.47 | A | 0.53 | A | 41 |
| MAB7 | 0.45 | A* | 0.50 | A* | 31 |
| MAB9 | 0.43 | B | 0.54 | A | 41 |

Table 177;
LSM = Least square mean;
% improvement = compare to control (GUI).
The SEQ ID NOs. of the cloned genes (according to the Gene Id) which are exogenously expressed in the plants are provided in Table 3 above.

TABLE 178

RGR of Mean(Leaf Average Area [cm^2]
Normal conditions, Day 5 from planting

| Gene Id | LSM | Significance | LSM of Best event | Significance | % improvement of best event |
|---|---|---|---|---|---|
| GUI | 0.23 | B | 0.23 | B | |
| MAB13 | 0.34 | A* | 0.39 | A* | 70 |
| MAB146 | 0.35 | A* | 0.50 | A | 117 |
| MAB99 | 0.26 | B | 0.44 | A | 89 |

Table 178;
LSM = Least square mean;
% improvement = compare to control (GUI).
The SEQ ID NOs. of the cloned genes (according to the Gene Id) which are exogenously expressed in the plants are provided in Table 3 above.

Tables 179-180 depict analyses of RGR of Leaf Average Area [cm^2] in plants overexpressing the polynucleotides of the invention under the regulation of 6669 promoter. Each Table represents an independent experiment, using 4 independent events per gene. Genes not connected by same letter as the control (A, B,) are significantly different from the control.

TABLE 179

RGR of Mean(Leaf Average Area [cm^2]
Normal conditions, Day 5 from planting

| Gene Id | LSM | Significance | LSM of Best event | Significance | % improvement of best event |
|---|---|---|---|---|---|
| GUI | 0.31 | B | 0.31 | B | |
| MAB19 | 0.35 | B | 0.48 | A | 56 |
| MAB43 | 0.39 | B | 0.52 | A | 70 |
| MAB6 | 0.28 | B | 0.50 | A | 62 |

Table 179;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 180

RGR of Mean(Leaf Average Area [cm^2]
Normal conditions, Day 8 from planting

| Gene Id | LSM | Significance | LSM of Best event | Significance | % improvement of best event |
|---|---|---|---|---|---|
| GUI | 0.69 | B | 0.69 | B | |
| MAB14 | 0.72 | B | 0.92 | A | 32 |
| MAB6 | 0.69 | B | 0.96 | A | 38 |

Table 180;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

Tables 181-182 depict analyses of Plot Dry weight (DW) in plants overexpressing the polynucleotides of the invention under the regulation of 6669 promoter. Each Table represents an independent experiment, using 4 independent events per gene. Genes not connected by same letter as the control (A, B,) are significantly different from the control.

TABLE 181

Dry Weight [g]
Normal conditions

| Gene Id | LSM | Significance | LSM of Best event | Significance | % improvement of best event |
|---|---|---|---|---|---|
| GUI | 7.75 | B | 7.75 | B | |
| MAB36 | 10.37 | A* | 13.21 | A | 71 |

Table 181;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 182

Dry Weight [g]
Normal conditions

| Gene Id | LSM | Significance | LSM of Best event | Significance | % improvement of best event |
|---|---|---|---|---|---|
| GUI | 5.23 | B | 5.23 | B | |
| MAB1 | 6.81 | A | 8.09 | A | 55 |
| MAB13 | 6.08 | B | 7.61 | A | 45 |
| MAB18 | 6.10 | B | 8.18 | A | 56 |
| MAB99 | 6.51 | A* | 8.42 | A | 61 |

Table 182;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

Tables 183-185 depict analyses of 1000 Seeds Weight in plants overexpressing the polynucleotides of the invention under the regulation of 6669 promoter. Each Table represents an independent experiment, using 4 independent events per gene. Genes not connected by same letter as the control (A, B,) are significantly different from the control.

TABLE 183

1000 Seeds Weight [g]
Normal conditions

| Gene Id | LSM | Significance | LSM of Best event | Significance | % improvement of best event |
|---|---|---|---|---|---|
| GUI | 0.02 | B | 0.02 | B | |
| MAB19 | 0.02 | B | 0.03 | A | 23 |
| MAB2 | 0.02 | B | 0.03 | A | 44 |
| MAB20 | 0.02 | A | 0.04 | A | 71 |
| MAB36 | 0.02 | B | 0.03 | A | 24 |
| MAB50 | 0.02 | B | 0.03 | A | 32 |
| MAB6 | 0.02 | B | 0.03 | A | 22 |
| MAB9 | 0.02 | A | 0.02 | A | 19 |

Table 183;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 184

1000 Seeds Weight [g]
Normal conditions

| Gene Id | LSM | Significance | LSM of Best event | Significance | % improvement of best event |
|---|---|---|---|---|---|
| GUI | 0.02 | B | 0.02 | B | |
| MAB20 | 0.02 | A* | 0.02 | A | 17 |
| MAB6 | 0.02 | A* | 0.02 | A | 21 |

Table 184;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 185

1000 Seeds Weight [g]
Normal conditions

| Gene Id | LSM | Significance | LSM of Best event | Significance | % improvement of best event |
|---|---|---|---|---|---|
| GUI | 0.02 | B | 0.02 | B | |
| MAB100 | 0.02 | B | 0.02 | A | 23 |
| MAB17 | 0.02 | A | 0.03 | A | 33 |
| MAB18 | 0.02 | B | 0.02 | A | 18 |
| MAB35 | 0.02 | B | 0.02 | A | 28 |
| MAB46 | 0.02 | A | 0.02 | A | 21 |
| MAB99 | 0.02 | A | 0.03 | A | 37 |

Table 185;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

Tables 186-187 depict analyses of Seed Yield per Plant in plants overexpressing the polynucleotides of the invention under the regulation of 6669 promoter. Each Table represents an independent experiment, using 4 independent events per gene. Genes not connected by same letter as the control (A, B,) are significantly different from the control.

TABLE 186

Seed Yield per Plant [g]
Normal conditions

| Gene Id | LSM | Significance | LSM of Best event | Significance | % improvement of best event |
|---|---|---|---|---|---|
| GUI | 0.38 | B | 0.38 | B | |
| MAB1 | 0.50 | B | 0.61 | A | 61 |
| MAB10 | 0.46 | B | 0.59 | A | 53 |
| MAB14 | 0.50 | A* | 0.60 | A | 57 |
| MAB36 | 0.52 | A | 0.68 | A | 77 |
| MAB50 | 0.46 | B | 0.60 | A | 56 |

Table 186;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

TABLE 187

Seed Yield per Plant [g]
Normal conditions

| Gene Id | LSM | Significance | LSM of Best event | Significance | % improvement of best event |
|---|---|---|---|---|---|
| GUI | 0.32 | B | 0.32 | B | |
| MAB1 | 0.41 | A* | 0.49 | A | 53 |
| MAB13 | 0.43 | A | 0.55 | A | 69 |
| MAB18 | 0.39 | B | 0.49 | A | 53 |
| MAB32 | 0.41 | B | 0.50 | A | 56 |
| MAB35 | 0.41 | A* | 0.50 | A | 57 |
| MAB99 | 0.41 | A* | 0.51 | A | 57 |

Table 187;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants is provided in Table 3 above.

Table 188 depicts analyses of Harvest Index in plants overexpressing the polynucleotides of the invention under the regulation of 6669 promoter. Each Table represents an independent experiment, using 4 independent events per gene. Genes not connected by same letter as the control (A, B,) are significantly different from the control.

TABLE 188

Harvest Index
Normal conditions

| Gene Id | LSM | Significance | LSM of Best event | Significance | % improvement of best event |
|---|---|---|---|---|---|
| GUI | 0.48 | B | 0.48 | B | |
| MAB17 | 0.46 | B | 0.62 | A | 28 |

Table 188;
LSM = Least square mean;
% improvement = compare to control (GUI);
A meaning significant different at P < 0.05, A* meaning significant different at P < 0.1.
The SEQ ID NOs. of the cloned genes (according to the Gene Id) which are exogenously expressed in the plants are provided in Table 3 above.

Example 8

Transformation of Tomato M82 Plants with Putative ABST Genes

For the tomato transformation, tomato M82 seeds were previously sterilized with Na-hipochloride 3%+2-3 drops of Tween 20 (Polysorbate 20). Seeds were washed 3 times with distilled sterile water. Seeds were then germinated in full strength Nitsch medium and germinated for 8 days 8 days in growth room at 25° C. in the dark. Plantlets were then cut with 2-4 cm stem and insert it into a10-cm Petri dishes that were filled with 30-40 ml of MS liquid medium. Cotyledons were then cut and used as explants and later transferred onto KCMS solidified medium with 100 μM acetosyringone in a 10-cm Petri dish. Explants were inoculated with *A. tumefascience* for 30-50 minutes. Explants were co-cultivated for 24 hours and transferred to regeneration media including Kanamycin as selection medium. The resistant regenerated plantlets were then transferred into a rooting medium for 10-14 days until the appearance of the roots.

Example 9

Growth of M82 Tomato Transformed Plants and Phenotype Characterizations

Experimental Procedures

Producing Transgenic Tomato Plants

Plants were transformed as described in Example 8, above. Following transformation, $T_1$ M82 tomato plants were grown until fruit set. $T_2$ seeds have entered experiments to assess abiotic stress resistance.

Experimental Results

Assay 1—Tomato Field Trial Under Regular and Water Deficient Regimes

The tomato field trial was planned as a one source dripping irrigation (OSDI) system similar to a standard farmer field. Since water deficiency is applied in a relatively uniform manner, it allows measuring the effect of drought on small size populations of plants. The OSDI method was developed on the basis of the line source sprinklers irrigation system (Hanks et al. 1976 Soil Sci. Soc Am. J. 40 p. 426-429) with some significant modifications. Instead of sprinkler irrigation, dripping irrigation was used. In order to create a uniform and deep wet layer (at least 60 cm depth), and not the onion shape layer that is typically created by dripping irrigation, a low pressure compensating dripping irrigation system was used. This system enables to supply small amounts of water in a relatively long time frame. The drought stress field trial was performed in light soil, in an open field (net-house) near Rehovot, Israel. Between 4 to 5 events are been evaluated for each gene and the null segregating populations are used as negative controls. During the first three weeks all plants were grown in a nursery under normal irrigation conditions. After this period, plants were transplanted according to commercial growth protocol, maintaining a 30 cm distance between plants reaching a total density of 2,600 plants per 1000 sq. m (the recommended density in commercial growth). Each plant was transplanted near a water dripper and further subjected to two different treatments:

Optimal (100%): optimal irrigation conditions (100%). Irrigation was applied every 2 days as a standard recommended water supply. Standard recommended water supply is the amount applied by local commercial growers according to standard protocols.

Severe Stress (50%): 50% of the optimal amount of water irrigation was applied once a day (at same time as regular irrigation is applied)

All fertilizers were applied according to local standard protocols. Nitrogen was equally applied, as recommended, to all the treatments through the irrigation system. Each row, 193 cm wide, contained two dripping irrigation lines creating coverage of six drippers per 1 sq. m. The irrigation control was performed separately for each treatment. The experiment was structured in a four randomized block design, eight plants per plot. The different water regimes were initiated only four weeks three transplantation, when plants initiated the flowering stage. Water availability in the soil was recorded using tensiometers (used to determine matric water potential $\Psi m$ which allows to evaluate the stress severeness).

Assay 2—Tomato Salt Bath Experiment

Transgenic tomato seeds are sown in trays containing growth denitrified media. Seedlings are germinated under nursery conditions. The experimental model used was 3 blocks random distributed, where 10 plants per events were sown in each block. At the stage of first true leaf, trays are transferred to different "tanks" containing growth solution of 300 mM NaCl. For normal treatment, a full Hoagland solution was applied. 5 events for each gene are evaluated while null segregating populations are used as negative controls. The experiment is performed for a period of 8 weeks, where parameters such as chlorophyll content (measured as SPAD units), plant biomass (FW and DW) are measured.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES CITED

Additional References are Cited Hereinabove

1. World Wide Web (dot) fao (dot) org/ag/agl/agll/spush/degrad (dot) htm.
2. World Wide Web (dot) fao (dot) org/ag/agl/aglw/water-management/introduc (dot) stm.
3. McCue K F, Hanson A D (1990). Drought and salt tolerance: towards understanding and application. Trends Biotechnol 8: 358-362.
4. Flowers T J, Yeo Ar (1995). Breeding for salinity resistance in crop plants: where next? Aust J Plant Physiol 22:875-884.
5. Nguyen B D, Brar D S, Bui B C, Nguyen T V, Pham L N, Nguyen H T (2003). Identification and mapping of the QTL for aluminum tolerance introgressed from the new source, ORYZA RUFIPOGON Griff., into indica rice (Oryza sativa L.). Theor Appl Genet. 106:583-93.
6. Sanchez A C, Subudhi P K, Rosenow D T, Nguyen H T (2002). Mapping QTLs associated with drought resistance in sorghum (Sorghum bicolor L. Moench). Plant Mol Biol. 48:713-26.
7. Quesada V, Garcia-Martinez S, Piqueras P, Ponce M R, Micol J L (2002). Genetic architecture of NaCl tolerance in Arabidopsis. Plant Physiol. 130:951-963.
8. Apse M P, Blumwald E (2002). Engineering salt tolerance in plants. Curr Opin Biotechnol. 13:146-150.
9. Rontein D, Basset G, Hanson A D (2002). Metabolic engineering of osmoprotectant accumulation in plants. Metab Eng 4:49-56
10. Clough S J, Bent A F (1998). Floral dip: a simplified method for Agrobacterium-mediated transformation of Arabidopsis thaliana. Plant J 16:735-43.
11. Desfeux C, Clough S J, Bent A F (2000). Female reproductive tissues are the primary target of Agrobacterium-mediated transformation by the Arabidopsis floral-dip method. Plant Physiol 123:895-904.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US10995341B2). An electronic copy of the "Sequence Listing" will also be available from the USPTO upon request and payment of the fee set forth in 37 CFR 1.19(b)(3).

What is claimed is:

1. A method of increasing abiotic stress tolerance, seed yield, biomass, growth rate and/or nitrogen use efficiency of a plant as compared to the abiotic stress tolerance, seed yield, biomass, growth rate and/or nitrogen use efficiency of a control plant of the same species which is grown under the same growth conditions, comprising:
    (a) over-expressing within the plant a polypeptide comprising the amino acid sequence set forth by SEQ ID NO: 271, and
    (b) selecting said plants resultant of step (a) for:
    (i) an increased biomass, growth rate, seed yield, and/or nitrogen use efficiency under normal conditions as compared to a control plant of the same species which is grown under the same growth conditions,
    (ii) an increased tolerance to nitrogen deficiency as compared to a control plant of the same species which is grown under the same growth conditions, and/or
    (iii) an increased seed yield and/or rosette growth rate under salinity stress as compared to a control plant of the same species which is grown under the same growth conditions,
    thereby increasing the abiotic stress tolerance, seed yield, biomass, growth rate and/or nitrogen use efficiency of the plant as compared to the abiotic stress tolerance, seed yield, biomass, growth rate and/or nitrogen use efficiency of the control plant of the same species which is grown under the same growth conditions.

2. A method of producing a crop, comprising growing a crop plant over-expressing a polypeptide comprising the amino acid sequence set forth by SEQ ID NO: 271, wherein said crop plant is derived from parent plants selected for increased tolerance to nitrogen deficiency, increased seed yield under salinity stress, increased rosette growth rate under salinity stress, increased seed yield under normal conditions, increased biomass under normal conditions, increased growth rate under normal conditions and/or increased nitrogen use efficiency as compared to a control plant of the same species which is grown under the same growth conditions, wherein said crop plant has said increased tolerance to nitrogen deficiency, said increased seed yield under salinity stress, said increased rosette growth rate under salinity stress, said increased seed yield under normal conditions, said increased biomass under normal conditions, said increased growth rate under normal conditions and/or said increased nitrogen use efficiency, thereby producing the crop.

3. A method of selecting a plant having increased abiotic stress tolerance, seed yield, biomass, growth rate and/or nitrogen use efficiency as compared to a control plant of the same species which is grown under the same growth conditions, the method comprising:
    (a) providing plants transformed with a nucleic acid construct comprising a polynucleotide comprising a nucleic acid sequence encoding a polypeptide, wherein said polypeptide comprises the amino acid sequence set forth by SEQ ID NO: 271, and a heterologous promoter for directing transcription of said nucleic acid sequence in a plant cell, and;
    (b) selecting said plants of step (a) for:
    (i) an increased biomass, growth rate, seed yield, and/or nitrogen use efficiency under normal conditions as compared to a control plant of the same species which is grown under the same growth conditions,
    (ii) an increased tolerance to nitrogen deficiency as compared to a control plant of the same species which is grown under the same growth conditions, and/or
    (iii) an increased seed yield and/or rosette growth rate under salinity stress as compared to a control plant of the same species which is grown under the same growth conditions,
    thereby selecting the plant having increased abiotic stress tolerance, seed yield, biomass, growth rate and/or nitrogen use efficiency as compared to the control plant of the same species which is grown under the same growth conditions.

4. The method of claim 3, further comprising:
    (c) growing a crop of said plant transformed with the nucleic acid construct.

5. The method of claim 3, wherein said growing comprises seeding seeds and/or planting plantlets of said plant transformed with the nucleic acid construct.

6. The method of claim 3, wherein said nucleic acid sequence is set forth by SEQ ID NO: 1559 or 81.

7. A method of increasing root length, root coverage, growth rate of rosette area, growth rate of rosette diameter, and/or increased seed yield of a plant as compared to the root length, root coverage, growth rate of rosette area, growth rate of rosette diameter, and/or seed yield of a control plant of the same species which is grown under the same growth conditions, comprising:
    (a) over-expressing within the plant a polypeptide comprising the amino acid sequence set forth by SEQ ID NO: 271, and
    (b) selecting said plants resultant of step (a) for:
    (i) an increased root length, root coverage, growth rate of rosette area, and/or seed yield under normal conditions as compared to a control plant of the same species which is grown under the same growth conditions,
    (ii) an increased growth rate of rosette diameter, growth rate of rosette area and/or seed yield under salinity stress as compared to a control plant of the same species which is grown under the same growth conditions, and/or (iii) an increased root coverage under nitrogen deficiency as compared to a control plant of the same species which is grown under the same growth conditions, thereby increasing the root length, root coverage, growth rate of rosette area, growth rate of rosette diameter, and/or seed yield of the plant as compared to the root length, root coverage, growth rate of rosette area, growth rate of rosette diameter, and/or seed yield of the control plant of the same species which is grown under the same growth conditions.

* * * * *